(12) United States Patent
Williams

(10) Patent No.: US 11,179,245 B2
(45) Date of Patent: Nov. 23, 2021

(54) LATERAL BLOCK PLATE

(71) Applicant: Seth Kevin Williams, Madison, WI (US)

(72) Inventor: Seth Kevin Williams, Madison, WI (US)

(73) Assignee: Seth K. Williams, Madison, WI (US)

( * ) Notice: Subject to any disclaimer, the term of this patent is extended or adjusted under 35 U.S.C. 154(b) by 0 days.

(21) Appl. No.: 16/549,117

(22) Filed: Aug. 23, 2019

(65) Prior Publication Data

US 2020/0008952 A1 Jan. 9, 2020

Related U.S. Application Data

(63) Continuation of application No. 15/994,139, filed on May 31, 2018, now Pat. No. 10,398,568, which is a continuation-in-part of application No. 15/280,684, filed on Sep. 29, 2016, now Pat. No. 9,987,145.

(60) Provisional application No. 62/235,643, filed on Oct. 1, 2015.

(51) Int. Cl.
*A61F 2/44* (2006.01)
*A61F 2/46* (2006.01)
*A61F 2/30* (2006.01)

(52) U.S. Cl.
CPC .......... *A61F 2/447* (2013.01); *A61F 2/30771* (2013.01); *A61F 2/4611* (2013.01); *A61F 2/30749* (2013.01); *A61F 2002/30153* (2013.01); *A61F 2002/30331* (2013.01); *A61F 2002/30405* (2013.01); *A61F 2002/30433* (2013.01); *A61F 2002/30484* (2013.01); *A61F 2002/30507* (2013.01); *A61F 2002/30578* (2013.01); *A61F 2002/30593* (2013.01); *A61F 2002/30604* (2013.01); *A61F 2002/30784* (2013.01); *A61F 2002/30787* (2013.01); *A61F 2002/4629* (2013.01); *A61F 2002/4687* (2013.01)

(58) Field of Classification Search
CPC ...... A61F 2/4455; A61F 2/446; A61F 2/4465; A61F 2/447; A61F 2/46; A61F 2/4611
See application file for complete search history.

(56) References Cited

U.S. PATENT DOCUMENTS

| 9,474,622 | B2 * | 10/2016 | McLaughlin | ......... A61F 2/4425 |
| 2014/0228958 | A1 * | 8/2014 | Niemiec | ............. A61F 2/30767 |
| | | | | 623/17.16 |
| 2014/0243985 | A1 * | 8/2014 | Lechmann | ............. A61B 17/86 |
| | | | | 623/17.16 |

* cited by examiner

*Primary Examiner* — Eduardo C Robert
*Assistant Examiner* — Christina Negrellirodriguez
(74) *Attorney, Agent, or Firm* — Bell & Manning, LLC

(57) ABSTRACT

A spine stabilization and fusion system includes a lateral cage configured for placement between an upper vertebra and a lower vertebra. A face of the lateral cage includes an opening. The system also includes a lateral plate that includes one or more holes extending from a lateral face of the lateral plate to a medial face of the lateral plate. The one or more holes are configured to receive one or more fasteners. The lateral plate also includes a protrusion formed on the medial face of the lateral plate, where the protrusion is configured to mate with the opening in the face of the lateral cage.

18 Claims, 35 Drawing Sheets

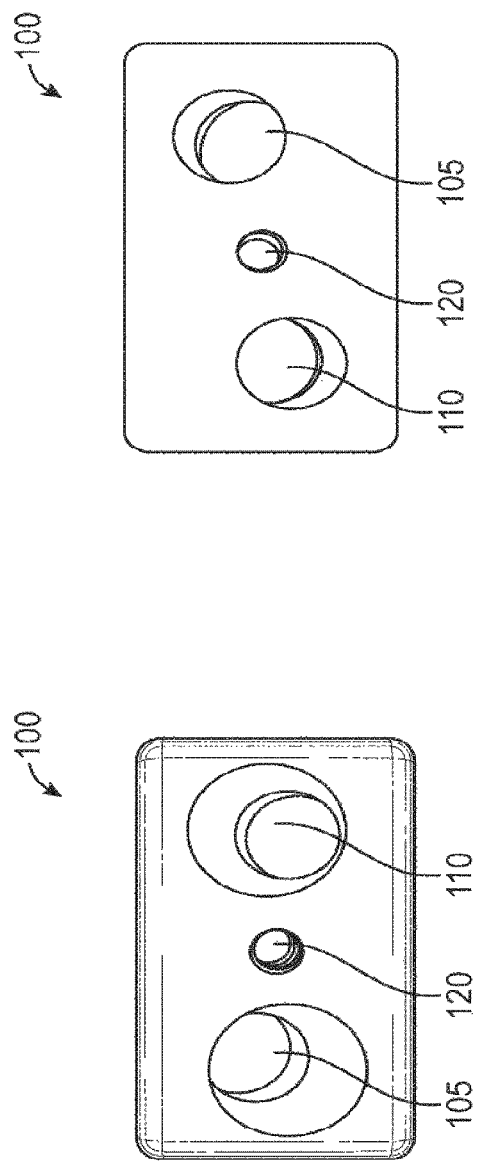
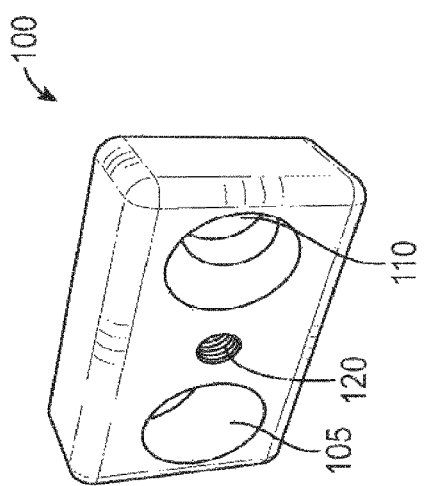

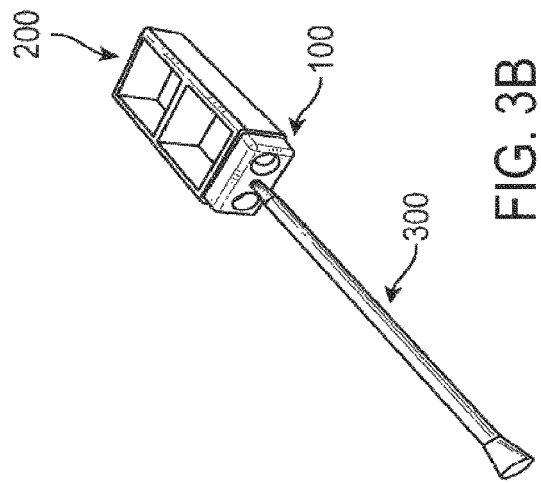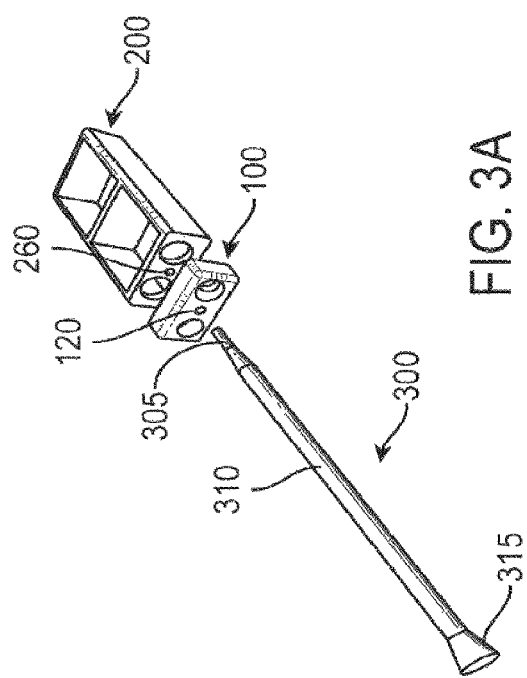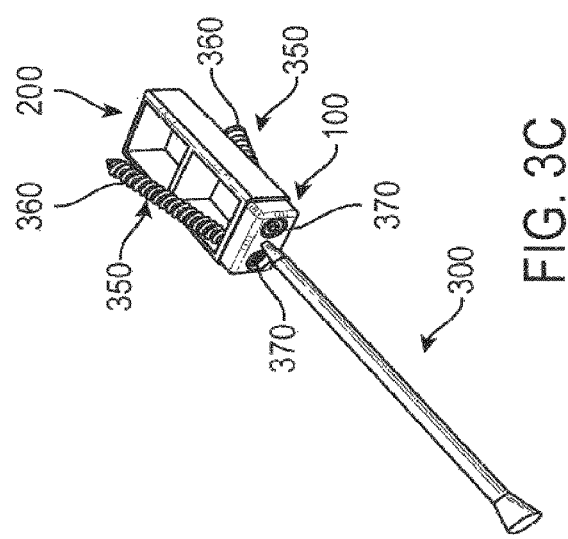

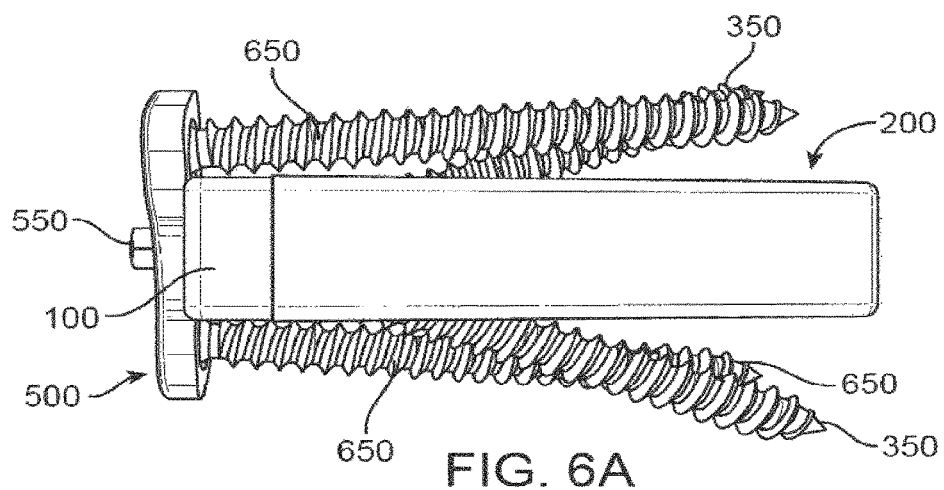
FIG. 6A
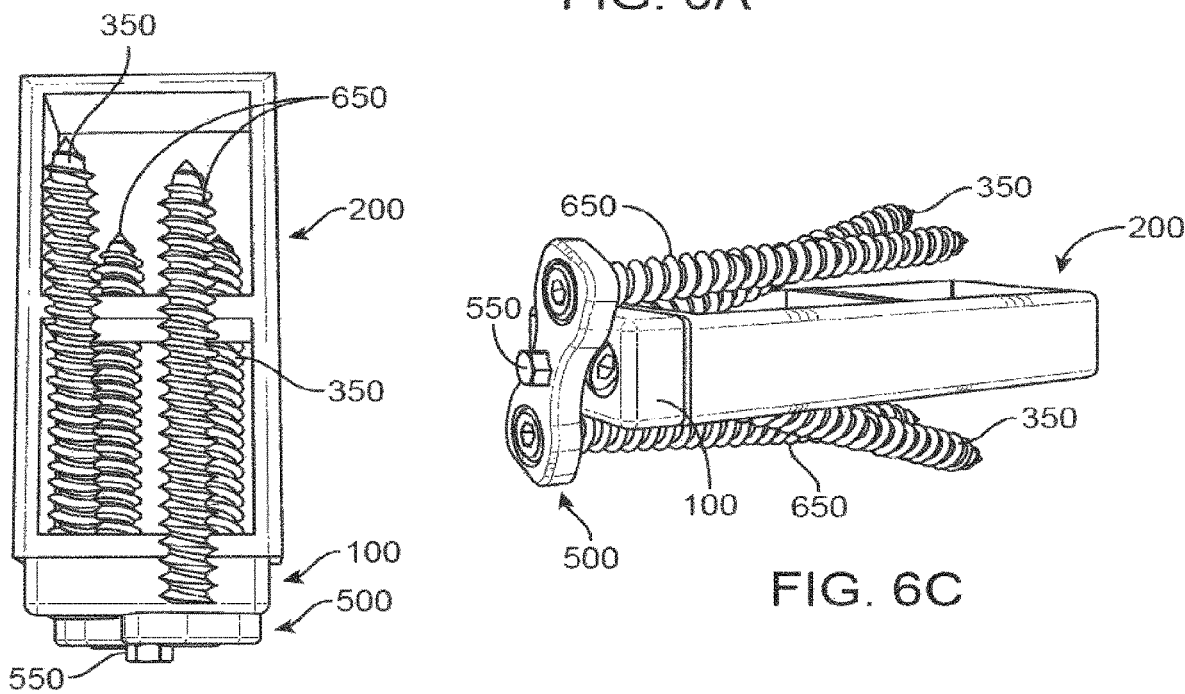
FIG. 6B
FIG. 6C
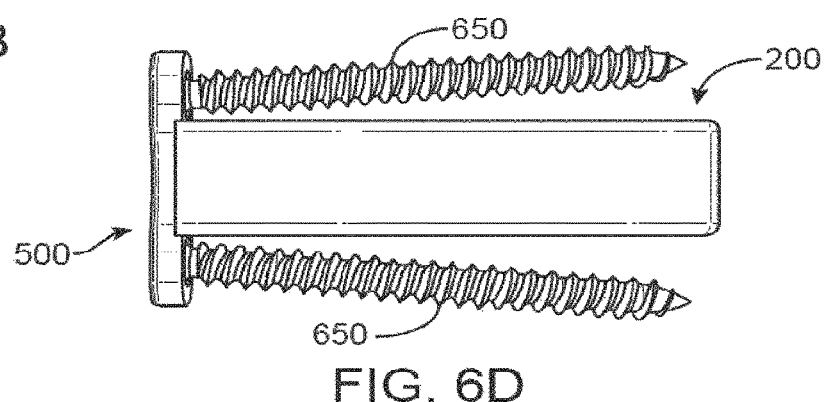
FIG. 6D

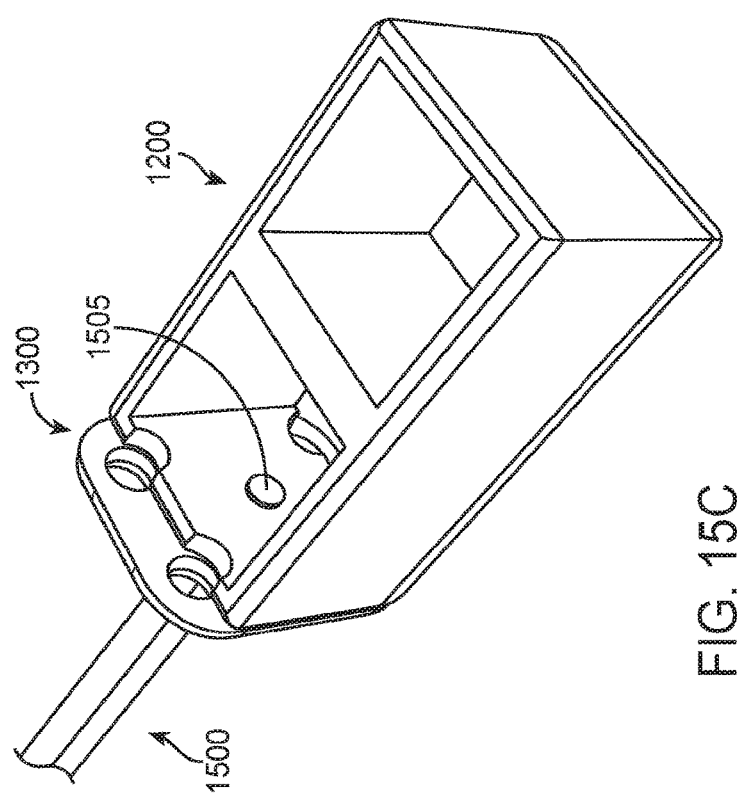
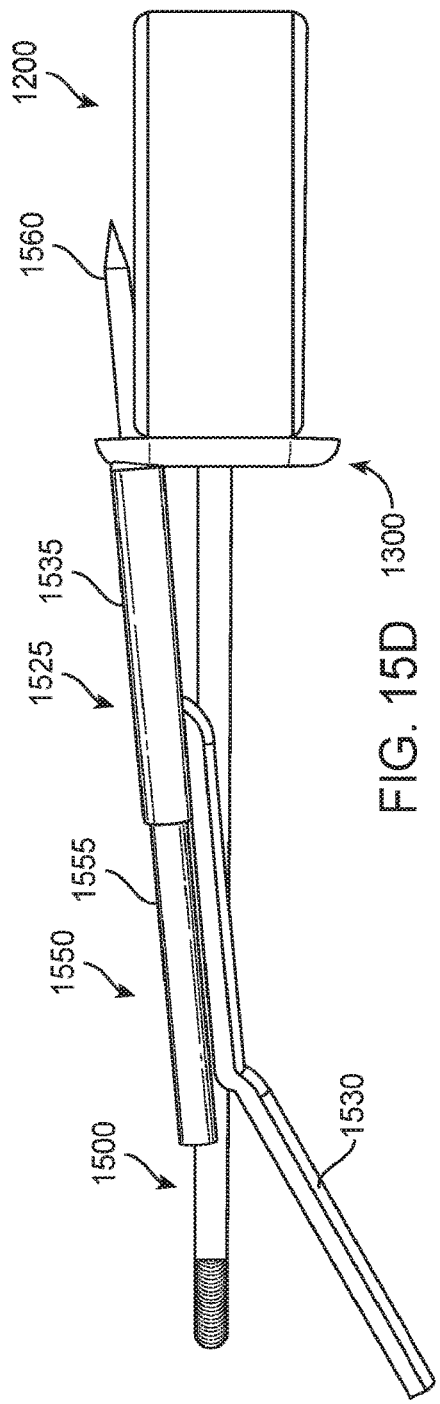
FIG. 15C
FIG. 15D

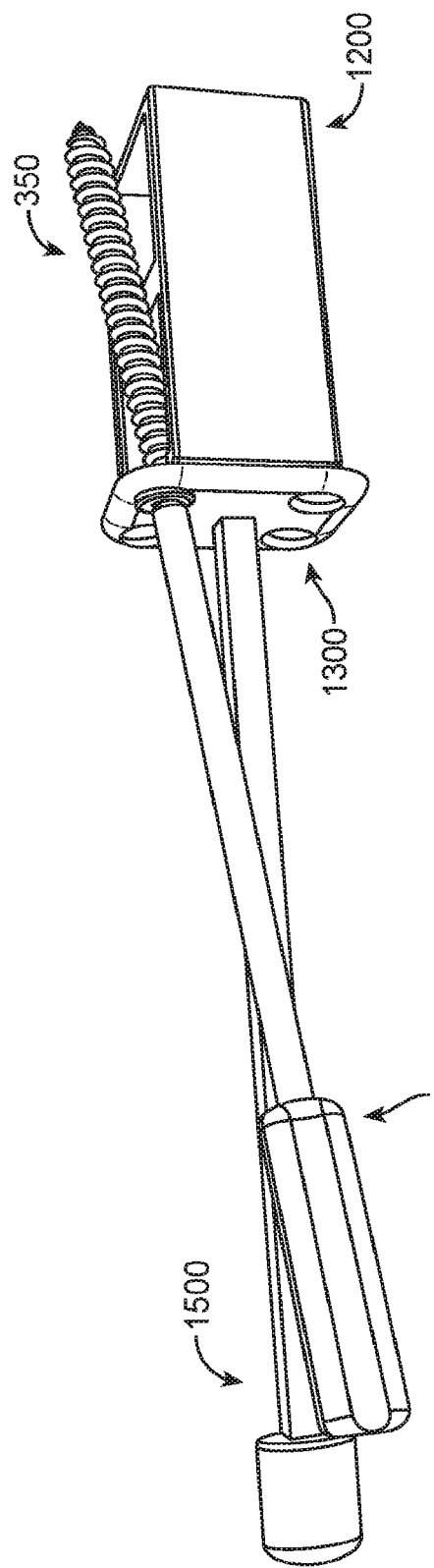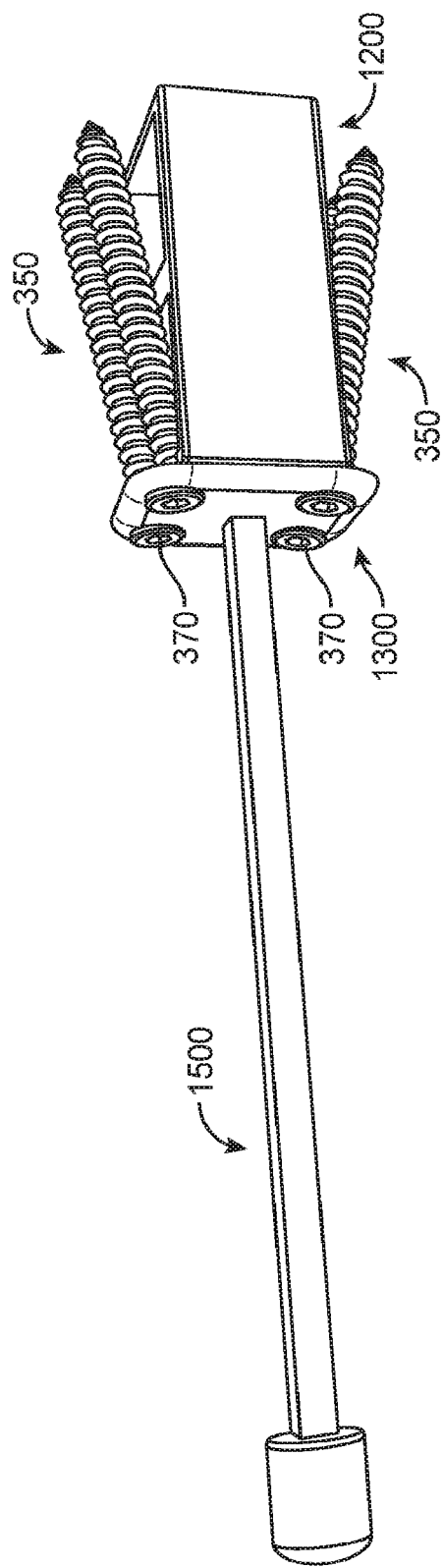

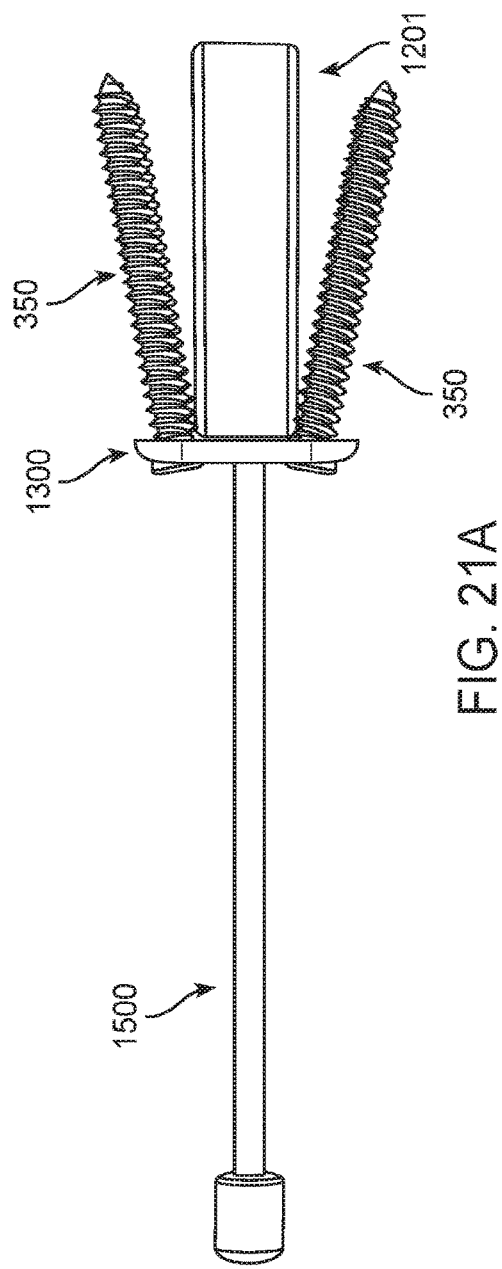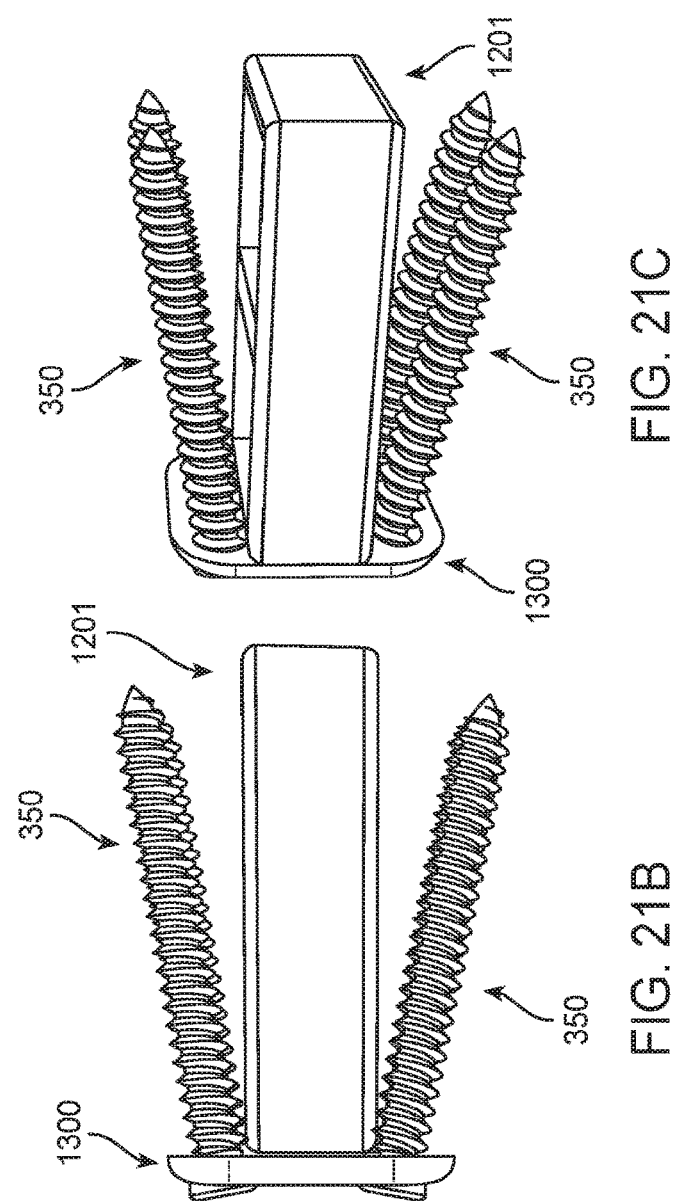

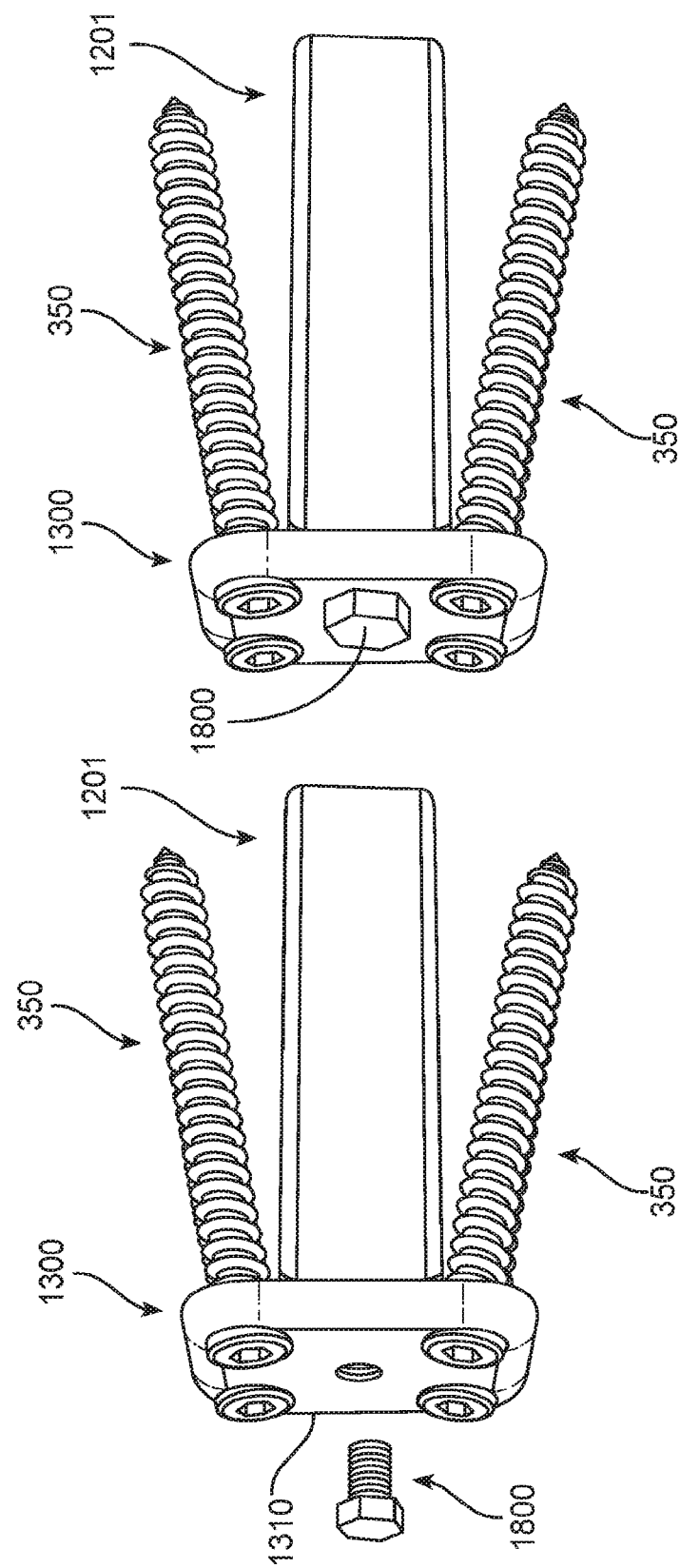

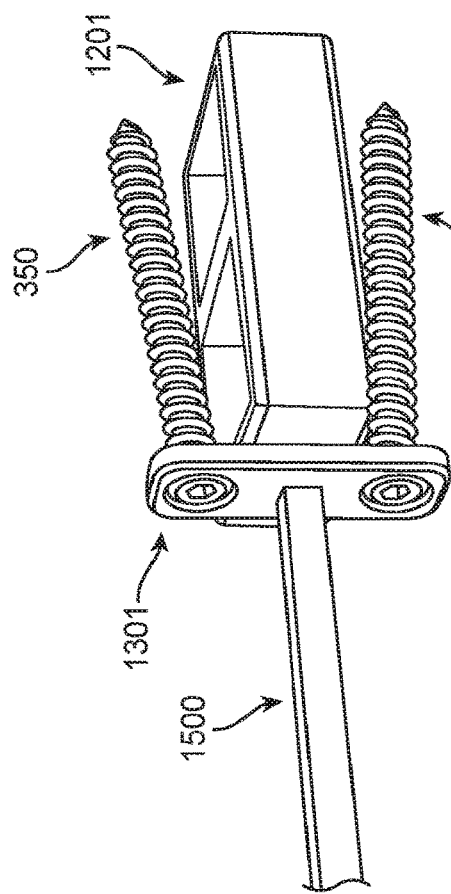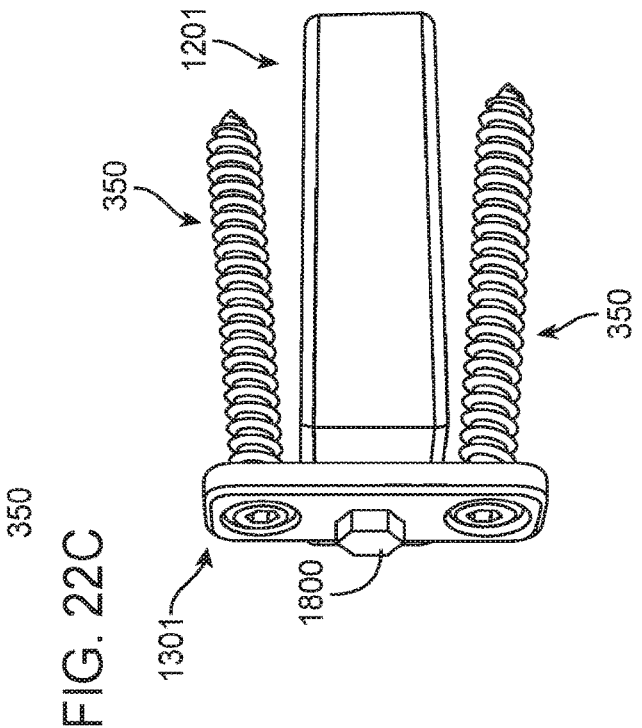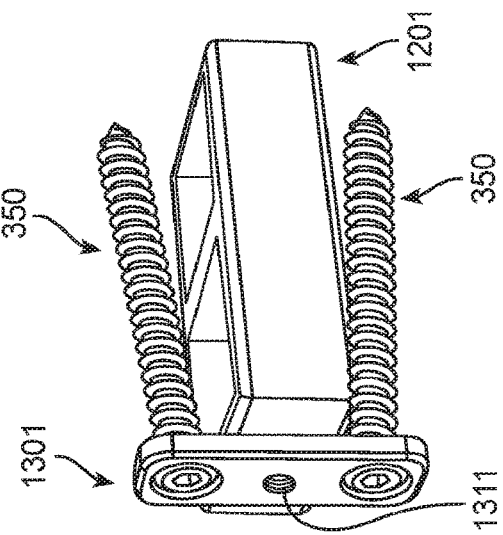

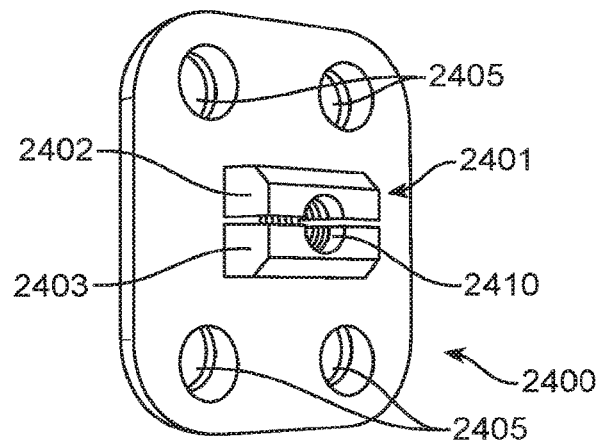
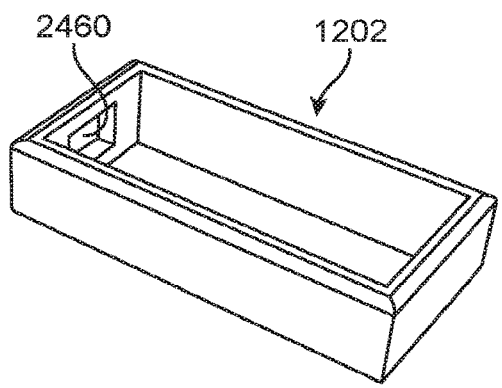
FIG. 24A  FIG. 24B
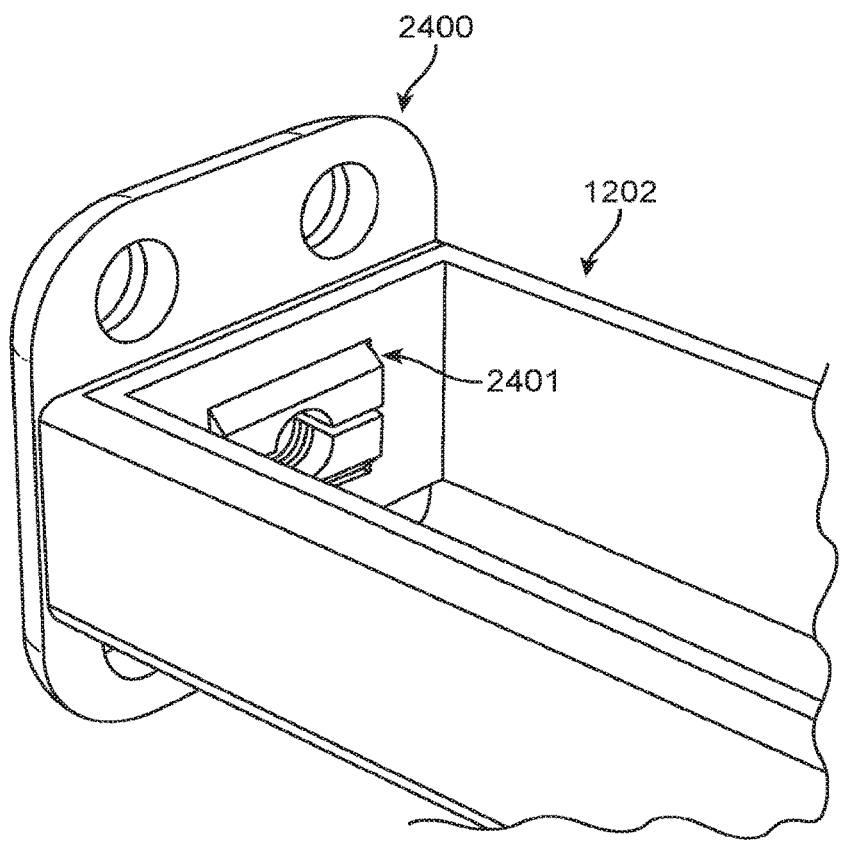
FIG. 24C

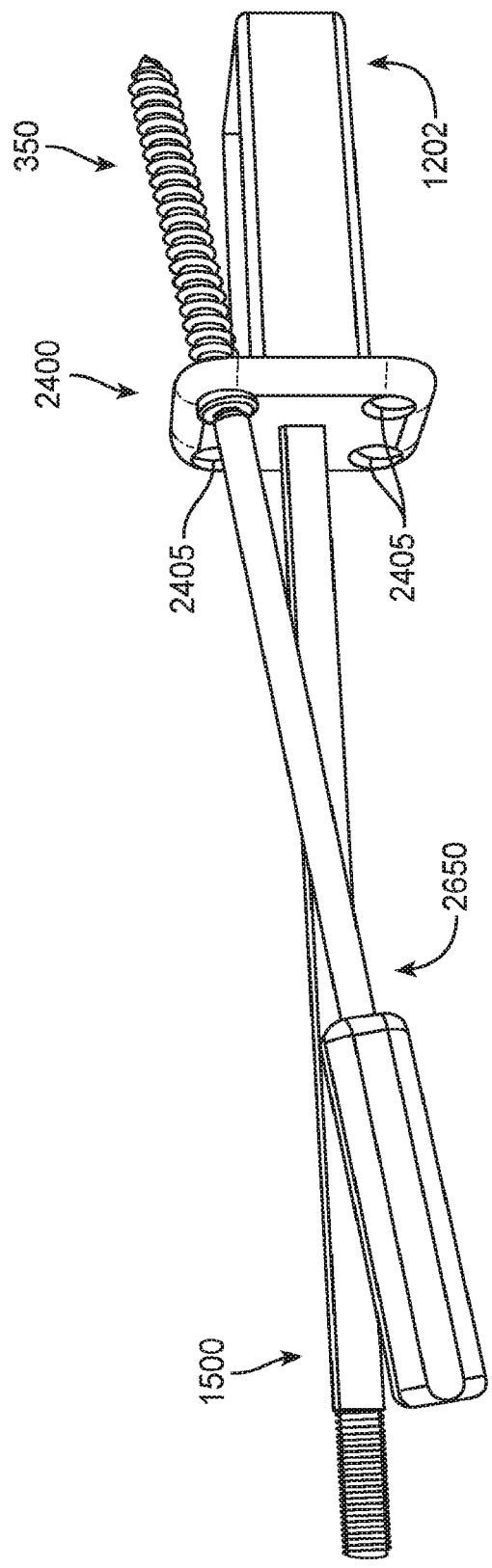
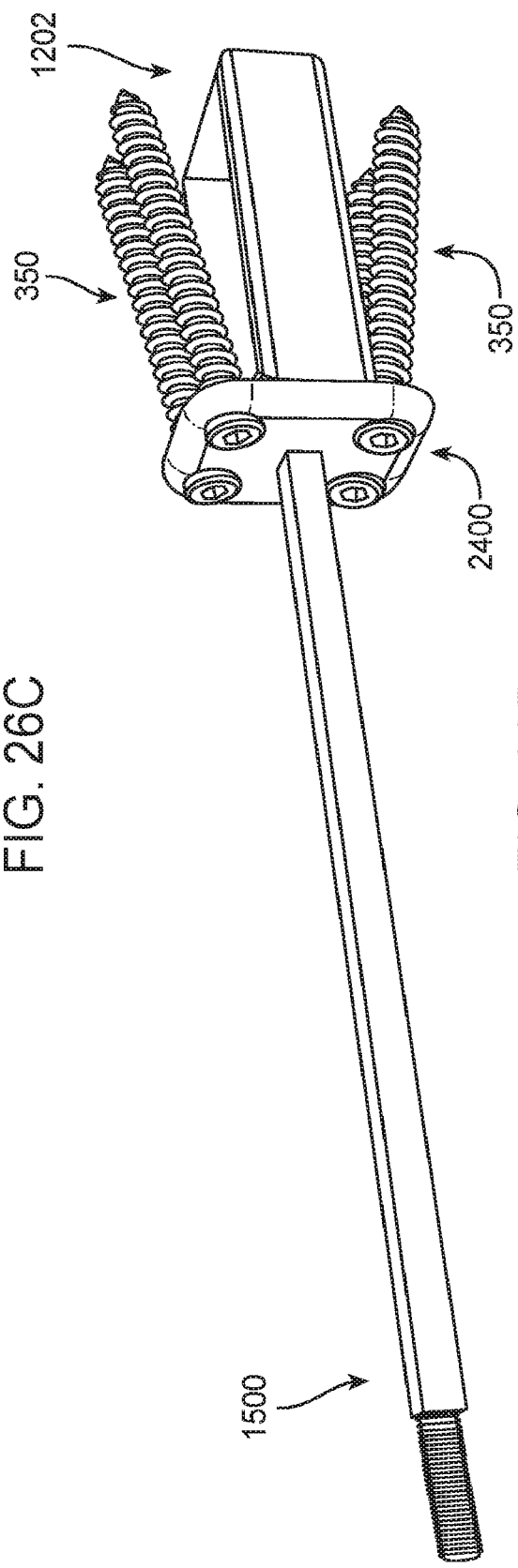
FIG. 26C
FIG. 26D

LATERAL BLOCK PLATE

CROSS-REFERENCE TO RELATED APPLICATIONS

The present application is a continuation application of U.S. patent application Ser. No. 15/994,139 filed on May 31, 2018, which is a continuation-in-part application of U.S. patent application Ser. No. 15/280,684 filed on Sep. 29, 2016, which claims the priority benefit of U.S. Provisional App. No. 62/235,643 filed on Oct. 1, 2015, the entire disclosures of which are incorporated herein by reference.

BACKGROUND

Lumbar spine fusion, or arthrodesis, is a surgical procedure that is performed to fuse two or more vertebrae together. During the procedure, a surgeon places a bone graft or other biological and/or scaffold material that is intended to promote new bone growth between two or more vertebrae. One form of fusion involves removing the majority of the intervertebral disk and replacing the disk with a structural cage that holds bone graft or other material. The spine segments being fused may be stabilized with spinal instrumentation such as a plate and screws. This type of fusion can be performed through a direct lateral or anterolateral retroperitoneal surgical approach. Spinal fusion surgery can be used to relieve nerve generated pain, and to treat ailments such as lumbar degenerative disk disease, spinal stenosis, lumbar spondylolisthesis, and scoliosis.

SUMMARY

An illustrative spine stabilization and fusion system includes a lateral cage and a lateral plate. The lateral cage is configured to be placed between an upper vertebra and a lower vertebra, and a face of the lateral cage includes an opening. The lateral plate includes one or more holes extending from a lateral face of the lateral plate to a medial face of the lateral plate. The one or more holes are configured to receive fasteners. The lateral plate further includes a protrusion formed on the medial face of the lateral plate, where the protrusion is configured to fit within the opening in the face of the lateral cage.

Another illustrative spine stabilization and fusion system includes a lateral cage and a lateral block plate. The lateral cage is configured to be placed between an upper vertebra and a lower vertebra, and a face of the lateral cage includes one or more first holes configured to receive fasteners and a first shaft bore configured to receive a shaft. The lateral block plate includes one or more second holes extending from a lateral face of the lateral block plate to a medial face of the lateral block plate and configured to receive the fasteners. The one or more second holes are configured to align with the one or more first holes of the lateral cage. The lateral block plate also includes a second shaft bore configured to receive the shaft, where the second shaft bore is configured to align with the first shaft bore of the lateral cage.

A method for spine stabilization and fusion includes placing a lateral cage into a disk space between an upper vertebra and a lower vertebra. A face of the lateral cage includes one or more first holes configured to receive fasteners and a first shaft bore configured to receive a shaft. The method also includes placing a lateral block plate adjacent to the lateral cage. The lateral block plate includes one or more second holes extending from a lateral face of the lateral block plate to a medial face of the lateral block plate and configured to receive the fasteners. The lateral block plate also includes a second shaft bore configured to receive the shaft. The method further includes placing the fasteners through the one or more second holes of the lateral block plate, through the one or more first holes of the lateral cage, and into endplates of the upper vertebra and the lower vertebra.

Another illustrative spine stabilization and fusion system includes a lateral cage configured for placement between an upper vertebra and a lower vertebra. A face of the lateral cage includes an opening. The system also includes a lateral plate that includes one or more holes extending from a lateral face of the lateral plate to a medial face of the lateral plate. The one or more holes are configured to receive one or more fasteners. The lateral plate also includes a protrusion formed on the medial face of the lateral plate, where the protrusion is configured to mate with the opening in the face of the lateral cage.

An illustrative method of forming a spine stabilization and fusion system includes forming a lateral cage that is configured to fit between an upper vertebra and a lower vertebra. The lateral cage is also formed such that a face of the lateral cage includes an opening. The method also includes forming a lateral plate, where forming the lateral plate includes forming a protrusion on a medial face of the lateral plate. The protrusion mates with the opening in the face of the lateral cage. Forming the lateral plate also includes forming one or more holes that extend from a lateral face of the lateral plate to a medial face of the lateral plate. The one or more holes are configured to receive one or more fasteners that extend into at least one of the upper vertebra and the lower vertebra.

The foregoing is a summary of the disclosure and thus by necessity contains simplifications, generalizations, and omissions of detail. Consequently, those skilled in the art will appreciate that the summary is illustrative only and is not intended to be in any way limiting. Other aspects, features, and advantages of the devices and/or processes described herein, as defined by the claims, will become apparent in the detailed description set forth herein and taken in conjunction with the accompanying drawings.

BRIEF DESCRIPTION OF THE DRAWINGS

FIGS. 1A-1C depict a lateral block plate in accordance with an illustrative embodiment.

FIG. 3A depicts an insertion handle, a lateral block plate, and a lateral cage in a disassembled configuration in accordance with an illustrative embodiment.

FIG. 3B depicts an insertion handle, a lateral block plate, and a lateral cage in an assembled configuration in accordance with an illustrative embodiment.

FIG. 3C depicts an insertion handle, a lateral block plate, and a lateral cage in an assembled configuration, with screws placed through and engaging the lateral block plate and passing freely through a wall of the lateral cage, in accordance with an illustrative embodiment.

FIG. 5B shows a lateral plate in a straight configuration, whereas FIG. 5C shows a lateral plate in an angled configuration.

FIGS. 6A-6C depict a front view, a top view, and an angled view, respectively, of a lateral block plate and screws adjacent to a lateral cage, as well as a lateral plate that is attached to a lateral block plate, with screws now placed through and engaging the lateral plate, in accordance with an illustrative embodiment.

FIG. 6D depicts a front view of a lateral cage with a lateral plate, without the lateral block plate, with screws engaging the lateral plate, in accordance with an illustrative embodiment.

FIGS. 15B-15C depict an inserter, a lateral plate, and a lateral cage in an assembled configuration in accordance with illustrative embodiments.

FIG. 15D depicts an inserter, a lateral plate, and a lateral cage in an assembled configuration, now with a drill bit guide, and a drill bit or awl used to establish the screw pathway through the plate into the vertebral body, in accordance with an illustrative embodiment.

FIG. 16A depicts an inserter, a lateral plate, and a lateral cage in an assembled configuration, with a screwdriver attached to a screw placed through a hole in the lateral plate and engaging the lateral plate and passing freely through a bore in the wall of the lateral cage, in accordance with an illustrative embodiment.

FIGS. 16B-16D depict an inserter, a lateral plate, and a lateral cage in an assembled configuration, with screws placed through holes in the lateral plate and engaging the lateral plate and passing freely through bores in the wall of the lateral cage, in accordance with illustrative embodiments.

FIG. 21A depicts an inserter, a lateral plate, and a lateral cage in an assembled configuration, with screws placed through holes in the lateral plate and engaging the lateral plate and passing cephalad and caudal to the walls of the lateral cage, in accordance with an illustrative embodiment.

FIGS. 21B-21C depict a lateral plate and a lateral cage with screws engaging the lateral plate and passing cephalad and caudal to the walls of the lateral cage, with the inserter removed, in accordance with illustrative embodiments.

FIG. 21D depicts a lateral plate and a lateral cage with screws engaging the lateral plate and passing cephalad and caudal to the walls of the lateral cage, with a bolt that connects the plate to the cage in a disassembled configuration, in accordance with an illustrative embodiment.

FIG. 21E depicts a lateral plate and a lateral cage with screws engaging the lateral plate and passing cephalad and caudal to the walls of the lateral cage, with a bolt connecting the plate to the cage in an assembled configuration, in accordance with an illustrative embodiment.

FIG. 22C depicts an inserter, a lateral plate, and a lateral cage in an assembled configuration, with screws placed through and engaging the lateral plate and passing cephalad and caudal to the walls of the lateral cage, in accordance with an illustrative embodiment.

FIG. 22D depicts a lateral plate and a lateral cage with screws engaging the lateral plate and passing cephalad and caudal to the walls of the lateral cage, in accordance with an illustrative embodiment.

FIG. 22E depicts a lateral plate and a lateral cage with screws engaging the lateral plate and passing cephalad and caudal to the walls of the lateral cage, with a bolt connecting the plate to the cage in an assembled configuration, in accordance with an illustrative embodiment.

FIG. 24A depicts an alternative embodiment of a lateral plate that engages a lateral cage via a medially-directed protrusion in accordance with an illustrative embodiment.

FIG. 24B depicts the alternative embodiment of a lateral or anterolateral cage that contains a hole that receives the medially-directed protusion feature of the alternative embodiment of the lateral plate cage in accordance with an illustrative embodiment.

FIG. 24C depicts the alternative embodiment of a lateral plate that engages a lateral cage via a medially-directed protrusion and the alternative embodiment of a lateral or anterolateral cage in an assembled configuration, in accordance with an illustrative embodiment.

FIG. 26C depicts an inserter, the alternative embodiment of a lateral plate that engages a lateral cage via a medially-directed protuberance, and a lateral cage, in an assembled configuration, in accordance with an illustrative embodiment. A screwdriver and screw are depicted, with the screwdriver used to place a screw through a hole in the lateral plate, with the screw thus anchoring the plate to a vertebral body (not shown), in accordance with an illustrative embodiment.

FIG. 26D depicts an inserter, the alternative embodiment of a lateral plate that engages a lateral cage via a medially-directed protuberance, and a lateral cage, in an assembled configuration, in accordance with illustrative embodiments. Four screws have been placed through the lateral plate, with the screws anchoring the plate to a vertebral body (not shown), in accordance with an illustrative embodiment.

DETAILED DESCRIPTION

Figure 2:
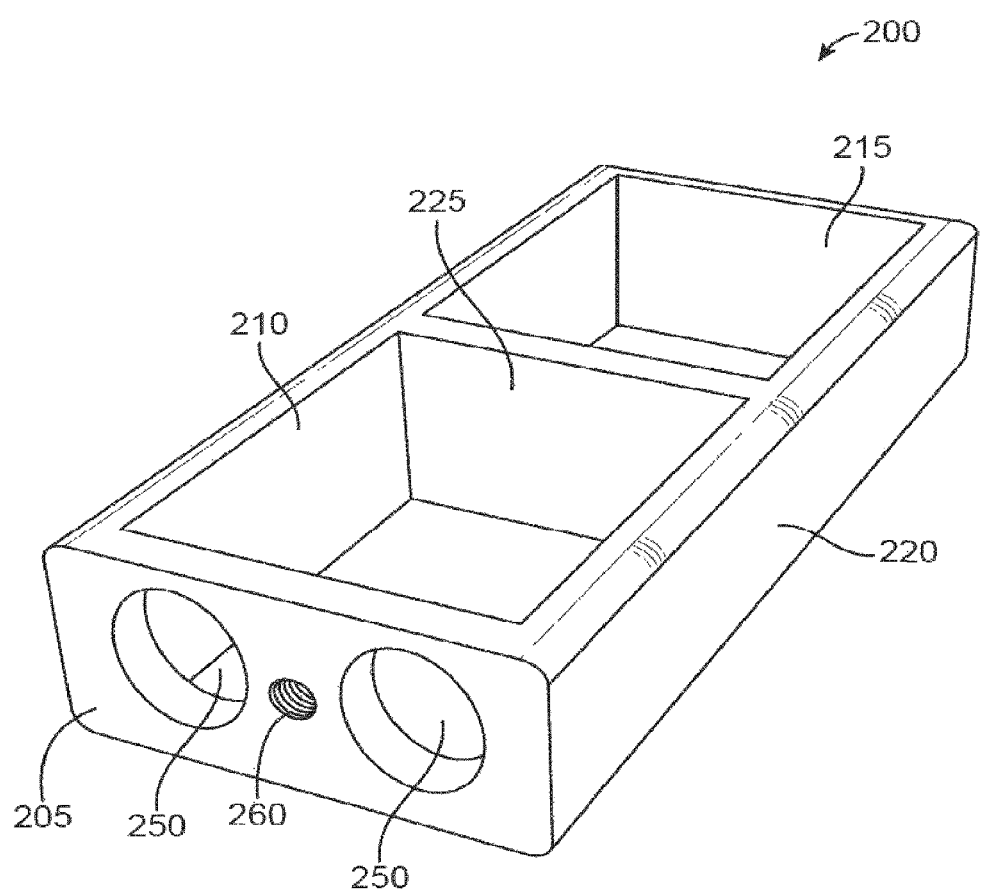
FIG. 2 depicts a lateral cage in accordance with an illustrative embodiment.

The following detailed description is of the best currently contemplated modes of carrying out exemplary embodiments of the subject matter described herein. The description is not to be taken in a limiting sense, but is made merely for the purpose of illustrating the general principles of the described subject matter, since the scope of the subject matter is best defined by the appended claims.

Spinal fusion procedures can be performed via several different approaches, including the lateral retroperitoneal approach or anterolateral retroperitoneal approach. Regardless of the approach used, traditional interbody spinal fusion procedures involve removal and replacement of an intervertebral disk with a cage that is used to provide structural support to the patient in place of the removed disk. The cage usually holds bone graft or other material that promotes a bony fusion, and typically fills some or all of the space that was previously occupied by the removed disk. The cage may be held in place and stabilized by a plate that is mounted outside of the disk space in a vertical position that is substantially perpendicular to both the disk space and the cage. The plate is secured by screws bored into the lateral sides of vertebral bodies above and below the disk space. As such, in traditional procedures, the plate is mounted to the sides of the vertebrae and sits outside the disk space with the screws penetrating the lateral vertebral body cortex, as opposed to sitting partially or completely within the disk space with the screws penetrating the endplates of the vertebrae.

Such spinal fusion techniques are prone to several problems due in part to the position in which the plate is mounted to the vertebral bodies. The psoas muscle and lumbar nerve plexus both run along the lateral sides of the vertebral bodies in the lumbar portion of the spine, making it difficult for the surgeon to properly place the vertical plate without interfering with one or both of the psoas muscle and the lumbar nerve complex. It can be difficult to hold the plate in position on the vertebral body while drilling the screw holes, as the force of the drill guide and the action of the drill on the hard vertebral bone have a tendency to cause the plate to migrate cephalad or caudal during drilling. Additionally, even when the surgeon is able to successfully place the plate, conventional plates may be prominent and can cause irritation to the psoas muscle and/or the lumbar nerve plexus. Another issue is the presence of pedicle screws in the vertebral body below or caudal to the fusion in cases where a patient has had a previous instrumented spinal fusion and now has developed adjacent segment deterioration above or cephalad to the previous fusion. In this situation it can be difficult to place a screw through a plate because the new screw trajectory often overlaps with the existing screw, and the surgeon is forced to place a longer plate than desired in order to allow for new screw placement below or cephalad to the existing screws. In view of these problems, the inventor has designed a new system that utilizes a cage in conjunction with a plate that may be positioned entirely or predominantly within the disk space. Additionally, the new system uses a plate or plates that are initially attached to the cage, which holds the plate or plates firmly in position so there is no plate movement during drilling, and then the plate or plates are detached from the cage to allow for separate biomechanical forces on the cages and plate or plates during patient activity.

Broadly, the embodiments described herein provide a spinal fusion plate that may be placed within the intervertebral space along with a cage in lateral and anterolateral spinal fusion procedures. Another lateral plate can be attached to the intervertebral plate, or can be used primarily, to provide additional options of achieving spinal stability. The spinal plates described herein solve the problems of traditional systems with plate placement and plate prominence and screw placement above a previous instrumented fusion because it can sit within the disk space, rather than outside the disk space. The system also solves the problem of plate migration during drilling because the plate or plates are initially attached to the lateral cage during the drilling and screw placement process.

FIG. 1A depicts a lateral or side view of a lateral block plate 100, in accordance with an illustrative embodiment. It is called a lateral block plate because in at least one embodiment it is shaped like a rectangular block. The lateral block plate 100 may be provided in different heights, such as in 1 millimeter (mm) increments starting at approximately 5 mm up to about 20 mm, depending on the thickness of the cage and the vertical dimensions of the intervertebral space to be filled. The lateral block plate 100 may have the same height anteriorly and posteriorly, or it can be configured to be taller anteriorly than posteriorly, thus reproducing or restoring a patient's lumbar lordosis. The plate width (i.e., the distance between the most lateral aspect of the plate and the most medial aspect of the plate) is selected to be between about 3-8 mm, preferably on the order of 5 mm. The lateral block plate length (i.e., the distance between the most posterior aspect of the plate and the most anterior aspect of the plate) can depend on the width of the cage, the width of the vertebrae to be fused, and/or the number of screw holes (e.g., 2, 3, or 4) to be used to secure the lateral block plate, and may be between about 15 mm-25 mm, preferably on the order of 20 mm. In alternative embodiments, different dimensions may be used for the height, width, and/or length of the lateral block plate. The lateral block plate 100 can be made with various materials, including titanium, titanium alloy, polyether ether ketone (PEEK), or a carbon fiber/PEEK combination. These are all existing materials that are commonly used for the manufacture of implanted medical devices. The lateral block plate is manufactured using existing manufacturing methods and standards that are currently used in the manufacture of medical implants. It should be understood, of course, that the foregoing relates to exemplary embodiments and that modifications may be made without departing from the spirit and scope of the invention as set forth in the claims.

Holes 105 and 110 accommodate screws or fasteners that pass through the lateral block plate 100 to secure it to bone. In an alternative embodiment, a lateral block plate may include more than two holes to accommodate screws or fasteners. In an illustrative embodiment, hole 105 is angled upwards between 10 and 25 degrees and hole 110 is angled downwards between 10 and 25 degrees. In alternative embodiments, different angles may be used for the holes 105 and 110. Holes 105 and 110 are tapered to allow for passage of a threaded screw shaft (shown later) through the plate with screw head engagement of the plate without the screw head being prominent. Hole 120 is threaded and accommodates an insertion handle or a bolt to attach a lateral plate (shown later) to a lateral block plate 100. In an alternative embodiment, hole 120 may not be threaded, but may be designed to accommodate a fastener that will attach to a lateral plate (shown later).

FIG. 1B depicts a back side view of a lateral surface of a lateral block plate 100, in accordance with an illustrative embodiment. Holes 105 and 110 accommodate screws or fasteners that pass through the lateral block plate to secure it to bone. Hole 105 is angled upwards between 10 and 25 degrees and hole 110 is angled downwards between 10 and 25 degrees. Hole 120 is threaded and accommodates an insertion handle or a bolt to attach a lateral plate to the lateral block plate. In an alternative embodiment, hole 120 may not be threaded, but may be designed to accommodate a fastener that will attach to a lateral plate (shown later). FIG. 1C depicts an angled view of a lateral block plate 100, in accordance with an illustrative embodiment. Holes 105 and 110 accommodate screws or fasteners that pass through the lateral block plate to secure it to bone. Hole 105 is angled upwards between 10 and 25 degrees and hole 110 is angled downwards between 10 and 25 degrees. Hole 120 is threaded and accommodates an insertion handle or a bolt to attach a lateral plate to the lateral block plate. In an alternative embodiment, hole 120 may not be threaded, but may be designed to accommodate a fastener that will attach to a lateral plate (shown later).

FIG. 2 depicts an angled view of a structural fusion cage 200, also called a lateral cage 200, that is designed to be inserted into the intervertebral space after a discectomy is performed via a retroperitoneal direct lateral or anterolateral approach, in accordance with an illustrative embodiment. A lateral cage may be comprised of walls 205, 210, 215, 220, and 225, or in an alternative embodiment, may be compromised of more or fewer walls. Wall 215 is the leading edge of the lateral cage 200, in that it is inserted first into the disk space, and faces laterally, opposite the surgical wound. Wall 205 is opposite wall 215 and faces lateral towards the surgical wound and is the only visible part of the cage to the surgeon once it is inserted in the disk space. As an example, if cage 200 was inserted via a right-sided direct lateral surgical approach, wall 215 would be the leading edge of insertion and would therefore face the left side of the patient's body, and wall 205 would face the right side of the patient's body, and would be visible from the surgical wound. While the dimensions of the cage may vary, it is estimated that the height will vary between approximately 6 mm and 20 mm, the length (the distance from wall 205 to wall 215, inclusive) will vary between approximately 35 mm and 60 mm, and the width (the distance from wall 210 to 220, inclusive) will vary between approximately 15 mm and 25 mm. Hole 260 is threaded and accommodates an insertion handle or a bolt to attach a lateral plate (shown later) to the lateral block plate. In an alternative embodiment, hole 260 may not be threaded, but may be designed to accommodate a fastener that will attach to a lateral plate (shown later). Holes 250 are designed to allow free passage of screws or fasteners that will be placed through a lateral block plate 100 to secure a lateral block plate 100 to a vertebral body or bodies. In an alternative embodiment, holes 250 may be located eccentrically in a cephalad or caudal direction in wall 205, such that holes 250 are completely open in a cephalad or caudal direction, to allow for free passage of screws or fasteners.

FIG. 3A depicts a disassembled angled view of the lateral cage 200, the lateral block plate 100, and an insertion handle 300, in accordance with an illustrative embodiment. Insertion handle 300 has a threaded leading end 305 that threads into lateral block plate 100 through threaded hole 120 and through lateral cage 200 through threaded hole 260. Insertion handle 300 has a shaft portion 310 of variable length and a back end 315 of variable configuration. Alternative embodiments of insertion handle 300 could have a variety of mechanisms to connect to lateral block plate 100 and lateral cage 200 rather than through a threaded terminal end 305 and threaded holes 120 and 260.

FIG. 3B depicts an assembled angled view of a lateral cage 200, a lateral block plate 100, and an insertion handle 300, in accordance with an illustrative embodiment. The lateral block plate 100 is securely held to lateral cage 200 through their connection to insertion handle 300, and can now be inserted into an intervertebral disk space as part of the fusion operation. Once inserted into the intervertebral disk space, screws 350 with a threaded shaft portion 360 and head portion 370 can be placed through lateral block plate 100 and lateral cage 200 to engage the vertebral bodies above and below the lateral cage 200, as depicted in FIG. 3C. The screw threaded shaft portion 360 will pass freely through the holes 105 and 110 (not shown here, shown in FIGS. 1A-1C) in the lateral block plate 100 and through the holes 250 (not shown) in the lateral cage 200, whereas the screw head portion 370 when fully inserted will engage the lateral block plate 100 and securely hold the lateral block plate 100 in place in the intervertebral space (shown later). In an alternative embodiment, fasteners other than screws 350 may be used to secure the lateral block plate 100 and the lateral cage 200 to the vertebral bodies.

Figure 4B:
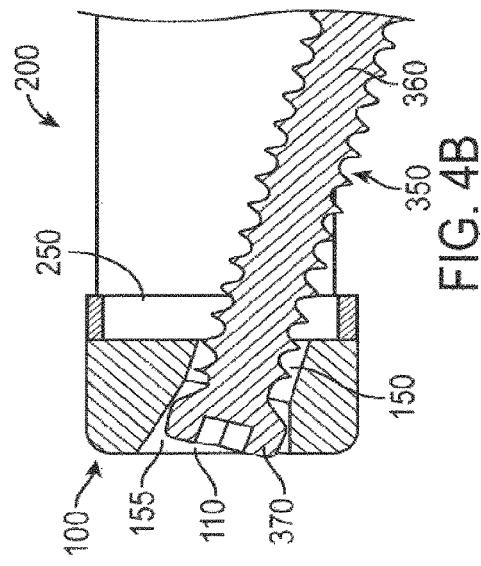
FIG. 4B is a frontal cross sectional view of a lateral block plate and a lateral cage with screws placed through a lateral cage and passing freely through a side wall of the lateral cage, with a screw head engaging the lateral block plate, in accordance with an illustrative embodiment.
Figure 4D:
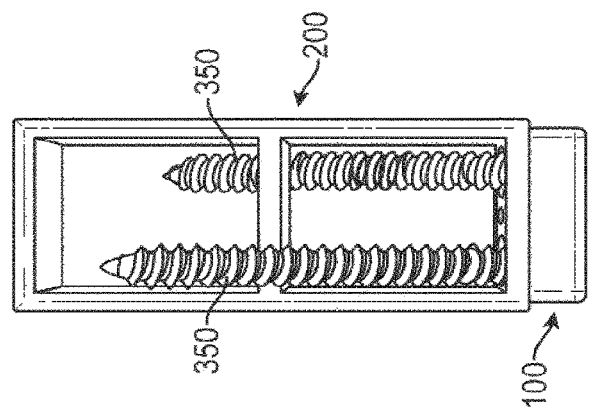
FIGS. 4C and 4D are angled and top views, respectively, of a lateral block plate and screws adjacent to a lateral cage as depicted in FIG. 4A.
Figure 4A:
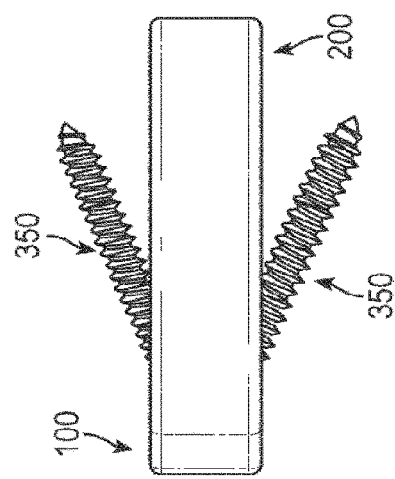
FIG. 4A depicts a front view of a lateral block plate and a lateral cage with screws placed through and engaging the lateral block plate and passing freely through a side wall of the lateral cage, in accordance with an illustrative embodiment.

FIG. 4A depicts a front view of the lateral block plate 100 and the lateral cage 200 with screws 350 placed through and engaging the lateral block plate 100 and passing freely through a side wall of the lateral cage 200, in accordance with an illustrative embodiment. Screws 350 are inserted into the vertebral bodies above and below the disk space being fused. Screws 350 are approximately 4 mm to 6 mm in diameter and between 20 mm and 60 mm in length. Provided the lateral block plate 100 is seated entirely or partially within the disk space, screws 350 enter the endplates of the vertebral bodies above and below the disk space being fused and are anchored in the cancellous vertebral body bone. If the lateral block plate is positioned more lateral, screws 350 may enter the lateral cortex of the vertebral bodies above and below the disk space being fused. The screw pathways may be established with a drill or an awl prior to insertion of screws 350. The rigid connection of the lateral block plate to the lateral cage via the insertion handle (not shown) prevents cage migration during screw pathway drilling and screw placement. In an alternative embodiment, fasteners other than screws may be used to secure a lateral block plate 100 to a vertebral body. Insertion handle 300 (not shown) has been removed after screw insertion.

Figure 4C:
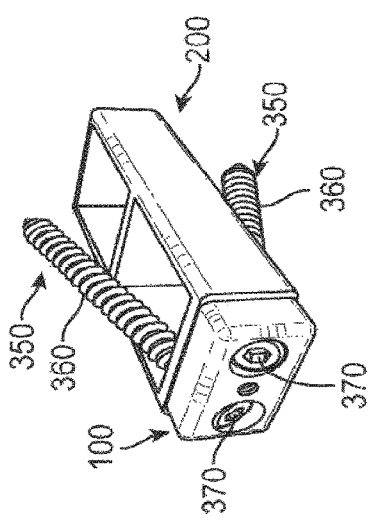

FIG. 4B is a frontal cross sectional view of a lateral block plate 100 and a lateral cage 200 with screw 350 placed through hole 110 in lateral block plate 100 and passing freely through hole 250 in a side wall of lateral cage 200, in accordance with an illustrative embodiment. Screw 350 is comprised of a threaded shaft portion 360 and a head portion 370. Hole 110 is tapered and has a larger diameter portion 155 that accommodates head portion 370, allowing the head portion 370 to seat fully or nearly-fully within lateral block plate 100 once inserted; and hole 110 has a smaller diameter portion 150 that is slightly larger than and allows free passage of threaded shaft portion 360 but is smaller than head portion 370. When screw 350 is inserted fully, head portion 370 tightly presses up against the smaller diameter portion 150 of hole 110, this securing the lateral block plate 100 to bone. FIG. 4C is an angled view of a lateral block plate 100 and screws 350 with screw heads 370 and threaded screw shafts 360, with the lateral block plate 100 adjacent to a lateral cage 200 as depicted in FIG. 4A and FIG. 4B, in accordance with an illustrative embodiment. FIG. 4D is top view of a lateral block plate 100 and screws 350 adjacent to a lateral cage 200 as depicted in FIGS. 4A and 4B, in accordance with an illustrative embodiment.

Figure 5B:
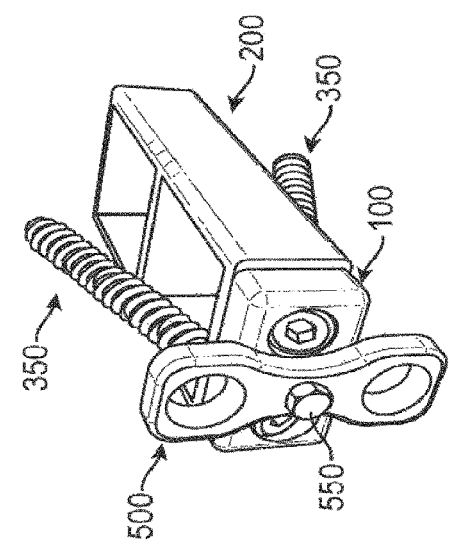
FIG. 5B depicts an angled view of a lateral block plate and screws adjacent to a lateral cage, as well as a lateral plate that is attached to the lateral block plate with a bolt, in accordance with an illustrative embodiment.
Figure 5A:
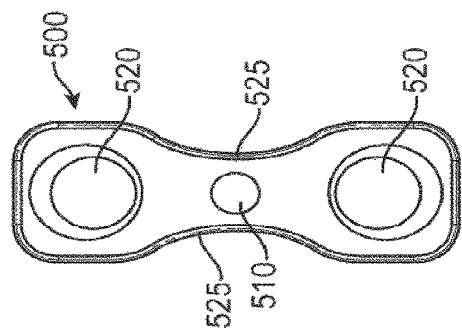
FIG. 5A depicts a side view of a lateral plate in accordance with an illustrative embodiment.

FIG. 5A depicts a side view of a lateral plate 500 with a tapered waist 525 and with a central hole 510 and eccentric holes 520, in accordance with an illustrative embodiment. Holes 520 allow for bone screws or fasteners to be placed for securing the lateral plate to bone. Central hole 510 allows for passage of a threaded bolt (550 shown in FIG. 5B) to connect the lateral plate 500 to a lateral block plate, or to allow for an insertion handle (shown in FIGS. 3A-3B) to engage a lateral plate 500, a lateral block plate 100, and a lateral cage 200 (shown in FIG. 5B) such that they can be inserted as a single unit prior to screw placement. Another option is for the surgeon to engage a lateral plate 500 with an insertion handle in order to hold it rigidly in place during screw pathway drilling and screw placement. In an alternative embodiment, a lateral plate 500 may not have a tapered waist and so may be shaped in a more rectangular manner and may include 3, 4, or more holes to accommodate bone screws or fasteners, and may be secured to a lateral block plate by a mechanism other than a bolt. The lateral plate 500 can be made with various materials, including titanium, titanium alloy, polyether ether ketone (PEEK), or a carbon fiber/PEEK combination. These are all existing materials that are commonly used for the manufacture of implanted medical devices. The lateral plate is manufactured using existing manufacturing methods and standards that are currently used in the manufacture of medical implants. It should be understood, of course, that the foregoing relates to exemplary embodiments and that modifications may be made without departing from the spirit and scope of the invention as set forth in the claims.

Figure 5D:
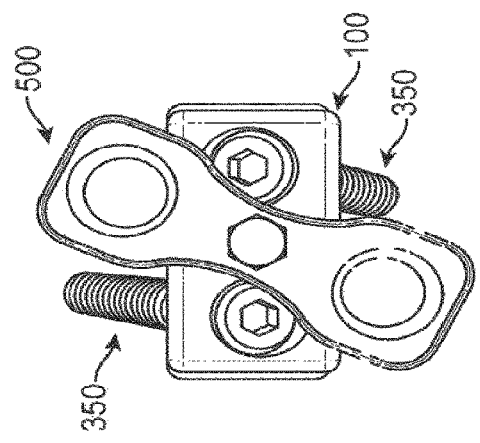
FIGS. 5C and 5D depict a side view of a lateral block plate and screws adjacent to a lateral cage, as well as a lateral plate that is attached to the lateral block plate, in accordance with an illustrative embodiment.
Figure 5C:
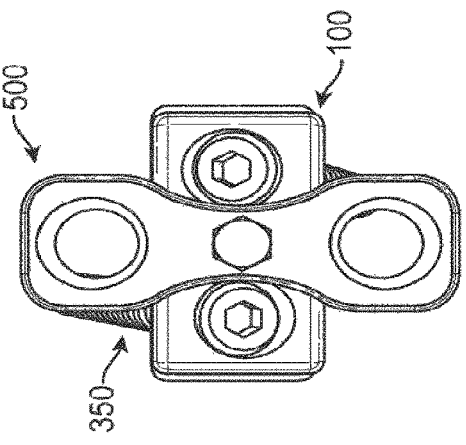

FIG. 5B depicts an angled view of the lateral block plate 100 and screws 350 adjacent to the lateral cage 200 as well as a lateral plate 500 that is attached to the lateral block plate 100 via bolt 550, in accordance with an illustrative embodiment. Bolt 550 is an optional feature that can be passed through central hole 510 as depicted in FIG. 5A, and would be placed after removal of the insertion handle (not shown) per the surgeon's discretion. Bolt 550, if used, would mate the lateral plate 500 to the lateral block plate 100 but would not mate to the lateral cage 200. FIGS. 5C and 5D depict a side view of the lateral block plate 100 and screws 350 adjacent to the lateral cage 200, as well as the lateral plate 500 that is attached to the lateral block plate 100 via bolt 550, in accordance with illustrative embodiments. FIG. 5C shows a side view of the lateral plate 500 in a straight configuration, whereas FIG. 5D shows a side view of the lateral plate 500 in a rotated configuration. The lateral plate 500 can be placed and rotated at any angle with respect to lateral block plate 100, provided the screw pathway does not overlap with the face of the lateral block plate. When the lateral plate 500 is positioned straight as in FIG. 5C, if the plate is designed with a tapered waist as depicted in FIGS. 5A and 5C, the screws 350 can be placed or accessed with the lateral plate 500 in place. The lateral plate 500 could then be rotated as depicted in FIG. 5D. When the lateral plate 500 is positioned rotated as in FIG. 5D, if the plate is designed with a tapered waist as depicted in FIG. 5A, the screws 350 are held in a locked position in that they are prevented from backing out due to the overlapping of plate 500 with the screw heads of screws 350.

FIG. 6A depicts a front view of the lateral block plate 100 with screws 350 adjacent to the lateral cage 200, as well as the lateral plate 500 that is attached to the lateral block plate 100 via bolt 550, with screws 650 now passing through and engaging the lateral plate 500, in accordance with an illustrative embodiment. Screws 650 have the same general configuration as screws 350, with a threaded shaft 360 as depicted in FIG. 4B and a screw head 370 that engages a plate as depicted in FIGS. 4B and 4C. Though similar in configuration, screws 650 are separately identified from screws 350 in this description to distinguish them from screws 350. The primary difference between screws 650 and screws 350 is that screws 350 pass through and engage via the screw head the lateral block plate 100 whereas screws 650 pass through and engage via the screw head the lateral plate 500. Hence in this description, the fundamental difference between the screw 350 and the screw 650 is not necessarily the physical dimensions of the screw, but the plate with which they are associated. Screws 350 are associated with the lateral block plate 100 and screws 650 are associated with the lateral plate 500. Screws 350 and screws 650 may have different dimensions depending on surgeon preference. FIG. 6B depicts a top view and FIG. 6C depicts an angled view of the lateral block plate 100 with screws 350 adjacent to the lateral cage 200, as well as the lateral plate 500 that is attached to the lateral block plate 100 via bolt 550, with screws 650 now passing through and engaging the lateral plate 500, in accordance with illustrative embodiments.

FIG. 6D depicts a front view of the lateral plate 500 adjacent to the lateral cage 200 with screws 650 passing through and engaging the lateral plate 500, in accordance with an illustrative embodiment. In an alternative embodiment, lateral plate 500 could be designed to accommodate more than two screws 650, the most common configuration likely being a total of four screws. In the configuration depicted in FIG. 6D, the surgeon has elected to not use a lateral block plate 100 as seen in FIGS. 6A-6C. The lateral plate 500 is initially secured to the lateral cage 200 via an insertion handle (not shown) in a manner similar to the assembly steps depicted in FIGS. 3A-3C, except in the method used as depicted in FIG. 6D the insertion handle engages the lateral plate 500 and the lateral cage 200, rather than engaging the lateral block plate 100 and the lateral cage 200 as depicted in FIGS. 3A-3C. Once the lateral cage 200 is inserted into the intervertebral space as part of the spinal fusion and the lateral plate 500 rests against the lateral aspects of the vertebral bodies above and below the disk space, the lateral plate 500 is held rigidly in position by virtue of the firm connection of the insertion handle (not shown) to the lateral plate 500 and the lateral cage 200, and the screw holes can be drilled. The advantage to this configuration is the rigid connection of the lateral plate 500 to the lateral cage 200, which due to the lateral cage being firmly seated within the disk space and with further control imparted by the insertion handle, prevents any movement or migration of the plate during screw pathway drilling and screw insertion. In one embodiment, a drill guide can be designed to mate with the insertion handle and rest against the plate, allowing for ease of drilling for the screws. Once screws 650 are placed into the vertebral bodies, the insertion handle (not shown) is removed, thereby completely disengaging a lateral plate 500 from the lateral cage 200, allowing the lateral plate 500 and the lateral cage 200 to be subject to separate biomechanical forces as the spinal column is loaded during patient activity.

Figure 7A:
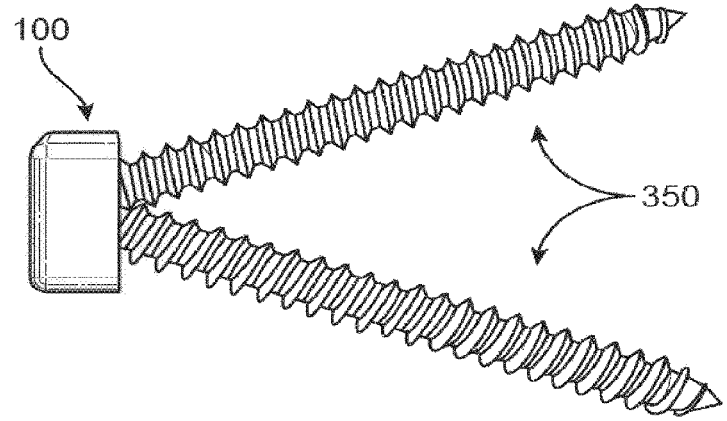
FIGS. 7A-7C depict a front view and two angled views showing the lateral sides of the of a lateral block plate with screws, in accordance with an illustrative embodiment.
Figure 7B:
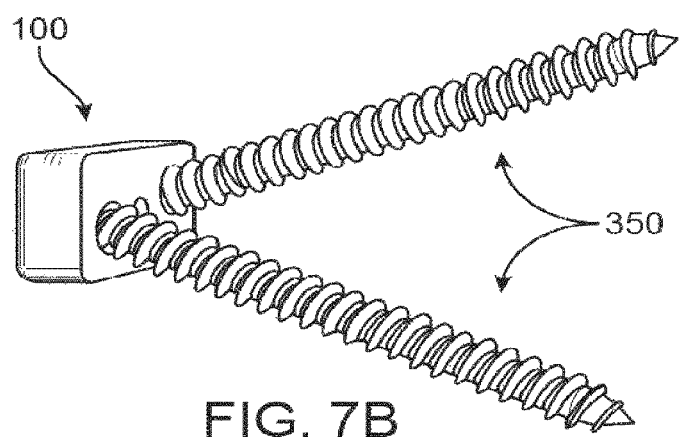
Figure 7C:
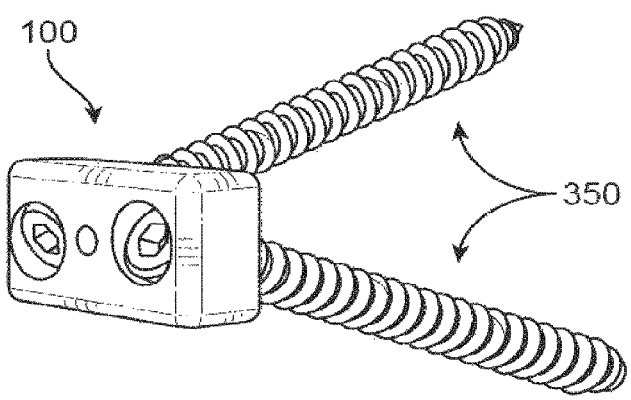

FIG. 7A depicts a front view of the lateral block plate 100 with screws 350, in accordance with an illustrative embodiment. FIGS. 7B and 7C depict angled views of the lateral block plate 100 with screws 350, in accordance with illustrative embodiments. Lateral block plate 100 in FIGS. 7A-7C is depicted without the lateral cage 200 or lateral plate 500 as seen in FIGS. 6A-6C.

Figure 8A:
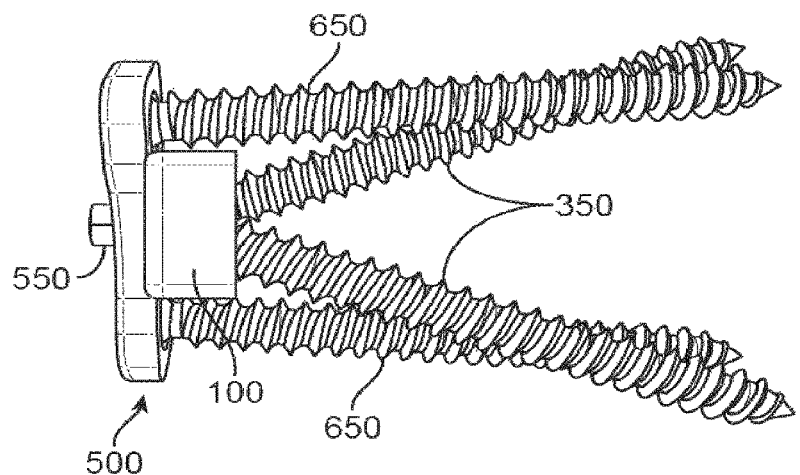
FIGS. 8A-8C depict a front view and two angled views showing the lateral sides of a lateral plate attached to a lateral block plate with screws engaging both plates, in accordance with an illustrative embodiment.
Figure 8B:
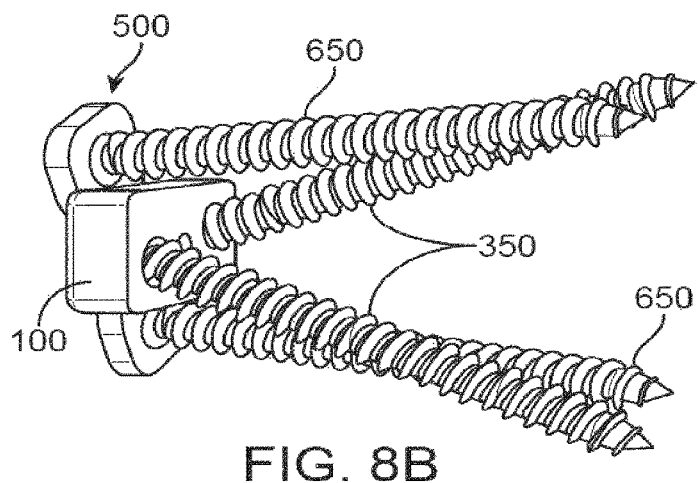
Figure 8C:
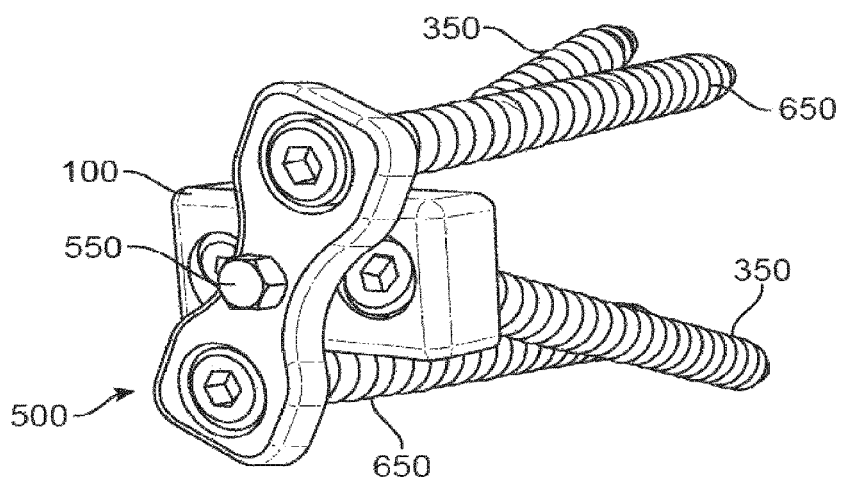

FIG. 8A depicts a front view of the lateral plate 500 attached to the lateral block plate 100 via bolt 550 with screws 650 placed through and engaging the lateral plate 500 and screws 350 placed through and engaging the lateral block plate 100, in accordance with an illustrative embodiment. FIGS. 8B and 8C depict angled views of the lateral plate 500 attached to the lateral block plate 100 via bolt 550 (not shown in FIG. 8B) with screws 650 placed through and engaging lateral plate 500 and screws 350 placed through and engaging lateral block plate 100, in accordance with illustrative embodiments. Lateral block plate 100 and lateral plate 500 in FIGS. 8A-8C are depicted without the lateral cage 200 as seen in FIGS. 6A-6C.

Figure 9:
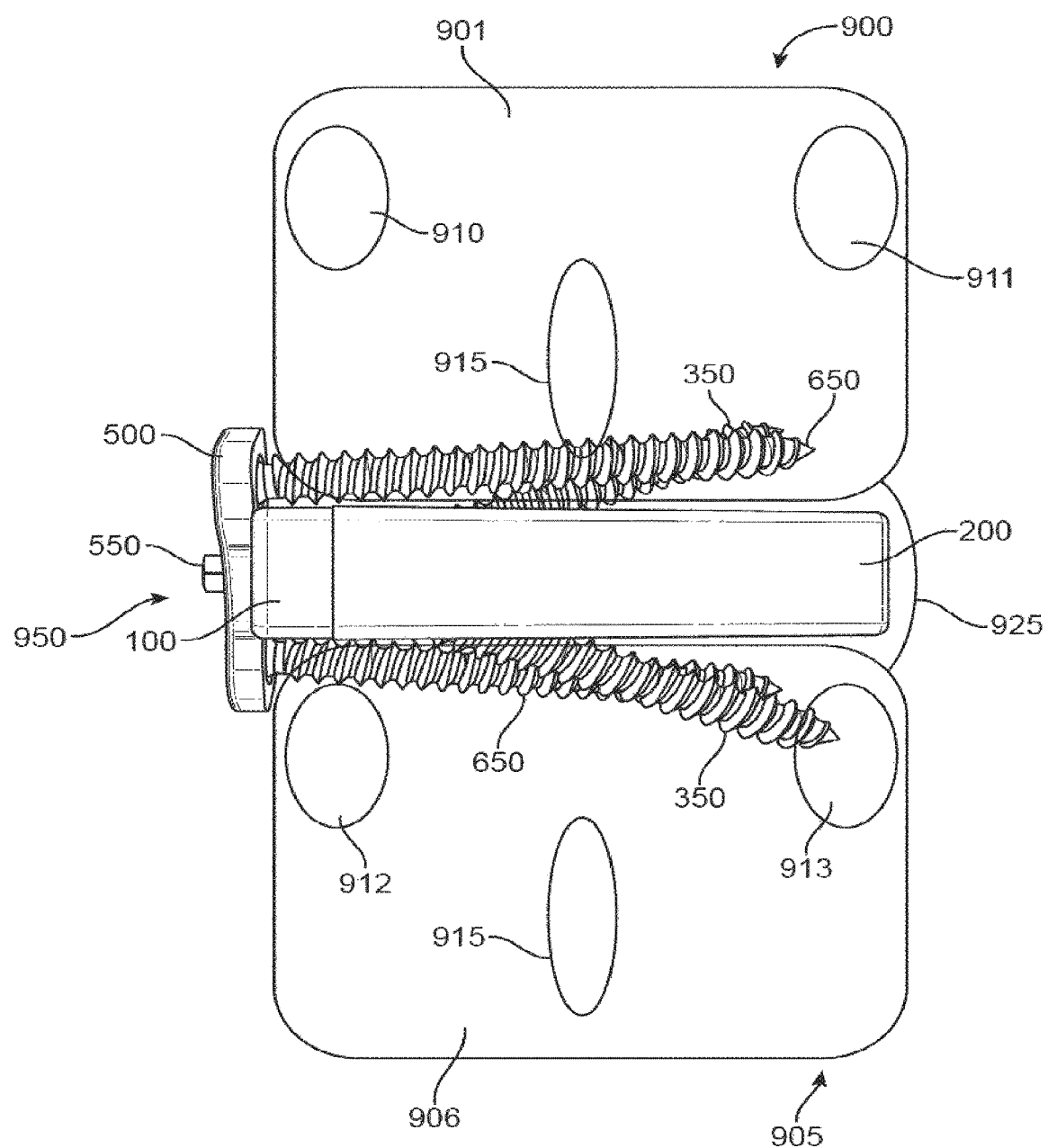
FIG. 9 depicts a front view of a spine segment with a vertebral body above and below a disk space, with the disk space occupied by the lateral block plate and screws adjacent to a lateral cage, as well as a lateral plate and screws, with the screws secured to the vertebral bodies, in accordance with an illustrative embodiment.

FIG. 9 depicts a front view of the lateral block plate 100 with associated screws 350 and the lateral plate 500 with associated screws 650 adjacent to the lateral cage 200 (950 collectively, as shown in FIG. 6A) after insertion into disk space 925 between vertebrae 900 and 905, in accordance with an illustrative embodiment. Vertebrae 900 is above or cephalad to the disk space and includes vertebral body 901 and pedicles 910 and 911 and spinous process 915. Vertebrae 905 is below or caudal to the disk space and includes vertebral body 906 and pedicles 912 and 913 and spinous process 915. The screw 350 inserted into vertebral body 906 passes above or cephalad to pedicle 912, so will pass above or cephalad to a pedicle screw (not shown) that would occupy pedicle 912 from a previous instrumented spinal fusion. The length of screw 350 can be selected to stop short of pedicle 913 if it is occupied with a pedicle screw (not shown) from a previous instrumented spinal fusion. The screw 650 may also be placed in a manner as to avoid a screw occupying pedicle 912.

Figure 10A:
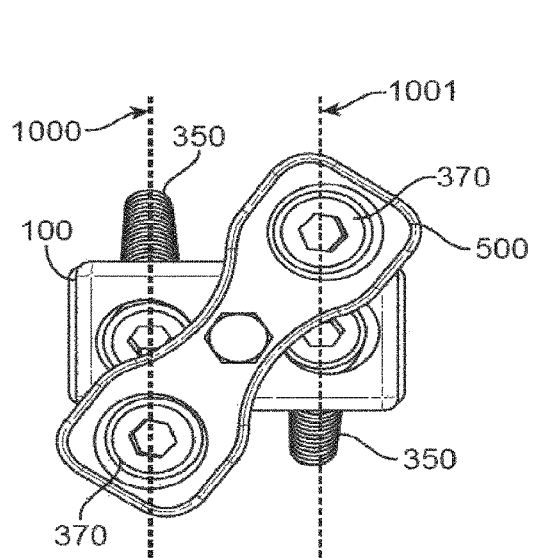
FIGS. 10A and 10B depict a side view and a top view, respectively, of a lateral block plate and a lateral plate and screws adjacent to a lateral cage, with lines drawn to indicate cross sectional planes depicted in FIGS. 10C and 10D, in accordance with an illustrative embodiment.
Figure 10B:
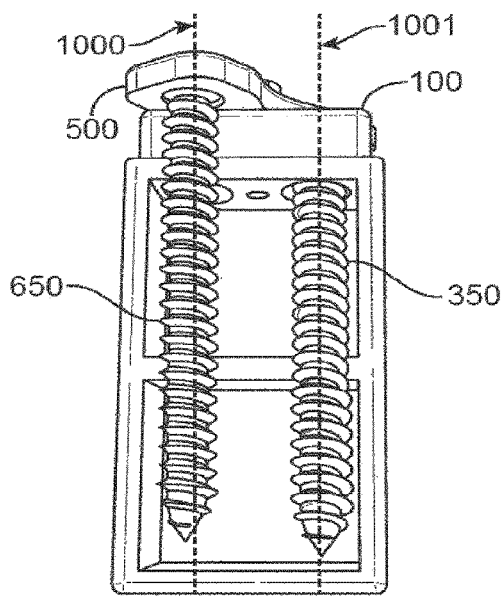
Figure 10C:
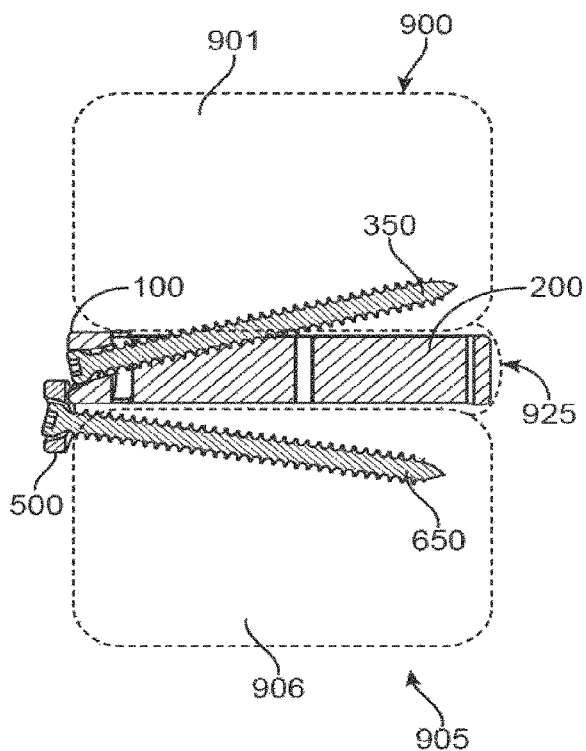
Figure 10D:
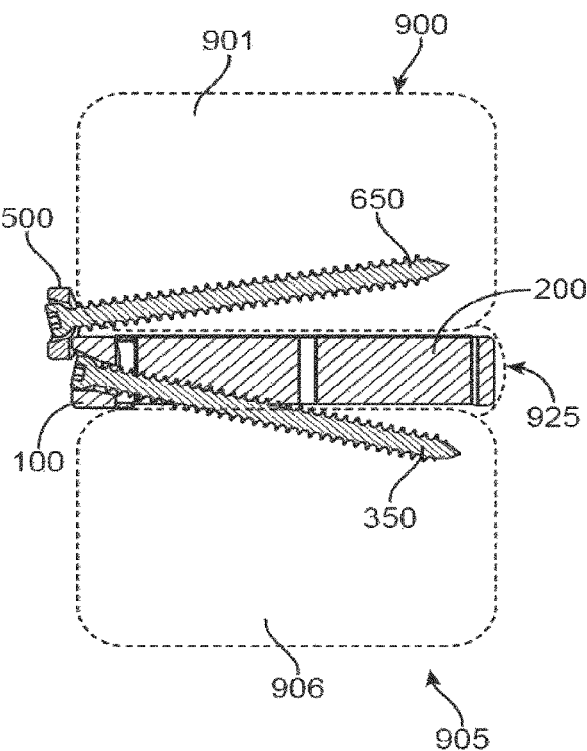

FIG. 10A depicts a side view of the lateral block plate 100 and lateral plate 500 and screws 350, and screw heads 370 of screws 650 (screws 650 not visible due to the angle of view), with lines 1000 and 1001 drawn to indicate cross sectional planes depicted in FIGS. 10C and 10CD respectively, in accordance with illustrative embodiments. FIG. 10B depicts a top view of the lateral block plate 100 with associated screw 350 and the lateral plate 500 with associated screw 650, with lines 1000 and 1001 drawn to indicate cross sectional planes depicted in FIGS. 10C and 10CD respectively, in accordance with illustrative embodiments. In FIG. 10B, screws 650 and 350 overlap, so only a single screw of each 350 and 650 are visible, though there are four screws present as depicted in FIG. 10A. FIG. 10C depicts a cross sectional image through plane 1000 (as shown in FIGS. 10A and 10B) of the lateral cage 200 inserted in a disk space 925 between a vertebrae 900 and a vertebrae 905, with the lateral block plate 100 and the lateral plate 500, in accordance with an illustrative embodiment. The lateral block plate 100 can sit entirely or partially within the disk space 925, or can be positioned outside and lateral to the disk space 925, whereas the lateral plate 500 is always positioned entirely outside a disk space 925. The screw 350 passes through the lateral block plate 100 and lateral cage 200 and is inserted into a vertebral body 901, with the screw head of a screw 350 engaging the lateral block plate 100, thus securing the lateral block plate 100 firmly to the vertebral body 901. The screw 650 passes through the lateral plate 500 and is inserted into the vertebral body 906, with the screw head of the screw 650 engaging the lateral plate 500, thus securing the lateral plate 500 firmly to the vertebral body 906. FIG. 10D depicts a cross sectional image through plane 1001 (as shown in FIGS. 10A and 10B) of the lateral cage 200 inserted in the disk space 925 between the vertebrae 900 and the vertebrae 905, with the lateral block plate 100 and the lateral plate 500, in accordance with an illustrative embodiment. The screw 350 passes through the lateral block plate 100 and the lateral cage 200 and is inserted into the vertebral body 906, with the screw head of the screw 350 engaging the lateral block plate 100, thus securing the lateral block plate 100 firmly to the vertebral body 906. The screw 650 passes through the lateral plate 500 and is inserted into the vertebral body 901, with the screw head of the screw 650 engaging the lateral plate 500, thus securing the lateral plate 500 firmly to the vertebral body 901.

Figure 11:
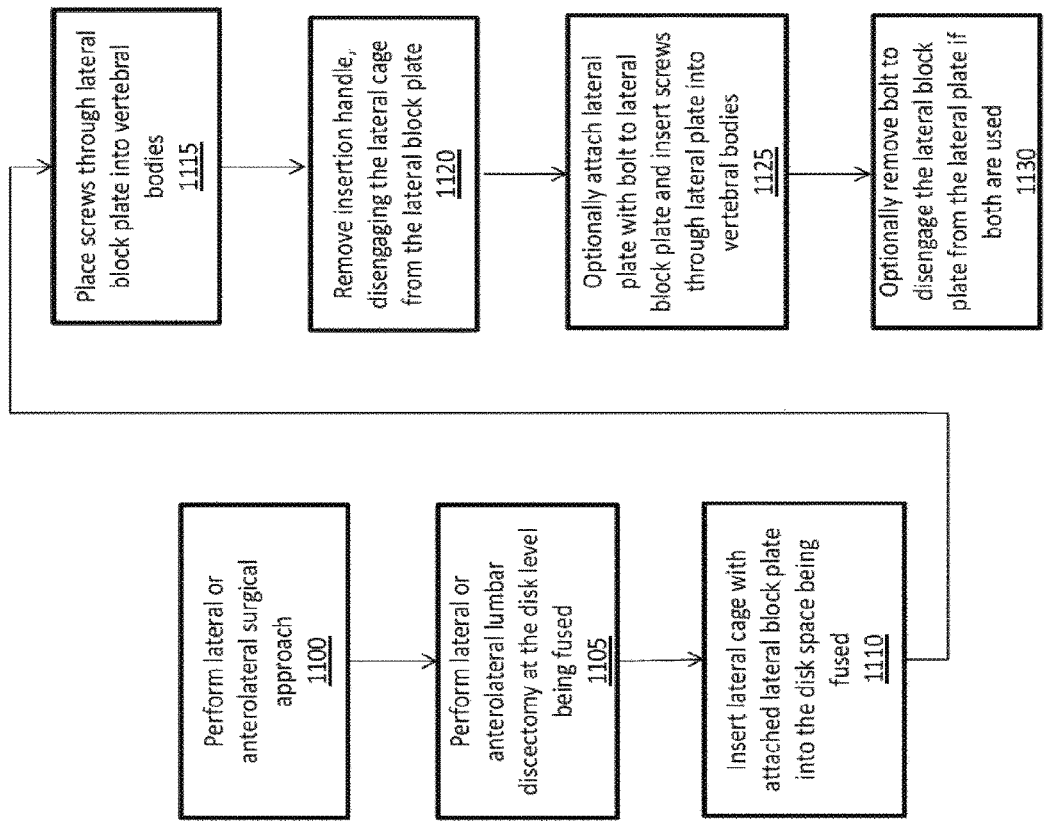
FIG. 11 is a flow diagram depicting a process for performing a lumbar spine fusion with a lateral block plate and/or a lateral plate in accordance with an illustrative embodiment.

FIG. 11 is a flow diagram depicting a process for performing a lumbar spine fusion in accordance with an illustrative embodiment. In alternative embodiments, fewer, additional, and/or different operations may be performed. Additionally, the use of a flow diagram is not meant to be limiting with respect to the order of operations performed.

In an operation 1100, the surgeon makes an incision and performs a retroperitoneal anterolateral or direct lateral approach to access the disk space to be fused in a manner well known to those skilled in the art.

In an operation 1105, the surgeon performs a lateral or anterolateral lumbar discectomy in a manner well known to those skilled in the art, in preparation for performing a fusion.

In an operation 1110, a lateral cage is attached to a lateral block plate via an insertion handle and is inserted into the disk space being fused. In illustrative embodiments, the disassembled lateral cage and lateral block plate and insertion handle are described with reference to FIG. 3A, and the assembled lateral cage and lateral block plate and insertion handle are described with reference to FIG. 3B.

In an operation 1115, the surgeon drills screw holes and places screws through the lateral block plate into the vertebral bodies above and below the disk space being fused. In an illustrative embodiment, the lateral block plate with screws are described with reference to FIG. 3C.

In an operation 1120, the surgeon removes the insertion handle, thus disengaging the lateral block plate from the lateral cage. This could be the conclusion of the fusion operation, or optionally depending on surgeon discretion in an operation 1125, the surgeon may now attach a lateral plate to the lateral block plate with a bolt. This holds the lateral plate rigidly in place to prevent plate migration during subsequent drilling of the screw holes and screw placement. Alternatively the surgeon could use an insertion handle to hold the lateral plate rigidly in place during screw pathway drilling. In an illustrative embodiment, the lateral block plate with screws through and engaging the lateral block plate, as well as the adjacent unattached lateral cage, are described with reference to FIGS. 5B-5D. Screws can now be placed through the lateral plate into the vertebral bodies above and below the disk level to be fused. In an illustrative embodiment, the lateral block plate with screws through and engaging the lateral block plate, and the lateral plate with screws through and engaging the lateral plate, as well as the adjacent unattached lateral cage, are described with reference to FIGS. 6A-6C and FIG. 9.

In an operation 1130, if the surgeon has used both the lateral block plate and the lateral plate and they are attached via a bolt, the surgeon may choose to remove the bolt connecting the lateral block plate to the lateral plate, allowing the lateral block plate with associated screws and the lateral plate with associated screws to be exposed to separate biomechanical forces. The choice of leaving the bolt in place or removing it is based on the clinical circumstances and is up to the discretion of the surgeon. Once the lateral cage, lateral block plate and/or lateral plate, and screws are fully inserted, the surgeon then completes the operation by closing the wound in a manner well known to those skilled in the art.

As described herein, anterolateral or lateral fusion operations performed with a lateral cage may be structurally supported by using an anterolateral or lateral plate. Plate migration while drilling screw pathways and placing screws into adjacent vertebral bodies is a common problem when the plate is not an integral part of the cage. As discussed above, to prevent this problem, several of the proposed embodiments involve a system that uses a plate or plates that are initially attached to the cage, which holds the plate or plates firmly in position so there is no plate movement during drilling. The plate or plates can then be optionally detached from the cage to allow for separate biomechanical forces on the cage(s) and plate(s) during patient activity. Additional embodiments described herein provide a spinal fusion plate that may be placed adjacent to the intervertebral space along with a cage in lateral and anterolateral spinal fusion procedures. The system provides further embodiments of solutions to the problem of plate migration during drilling and screw placement because the plate is initially and reversibly attached to the cage during the drilling and screw placement process.

Figure 12A:
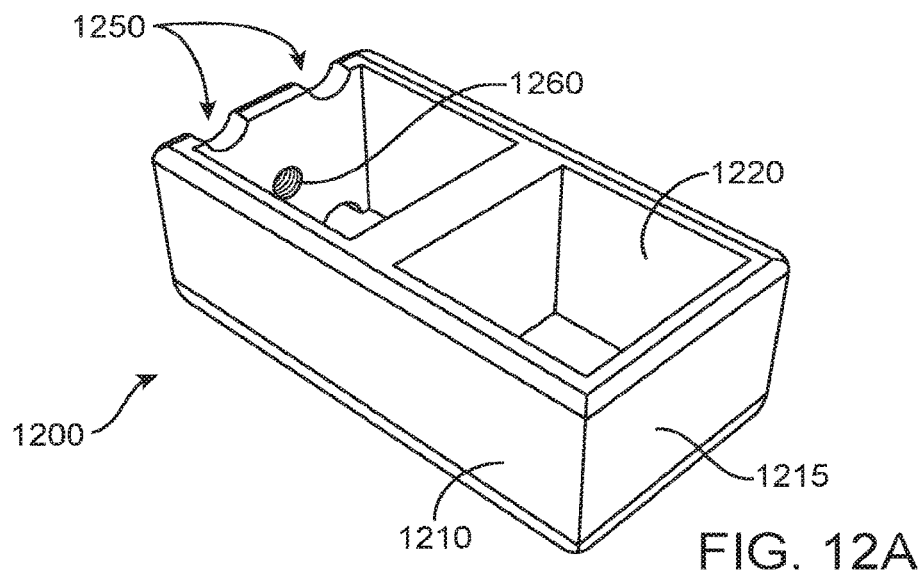
FIG. 12A depicts an angled top view.
Figure 12B:
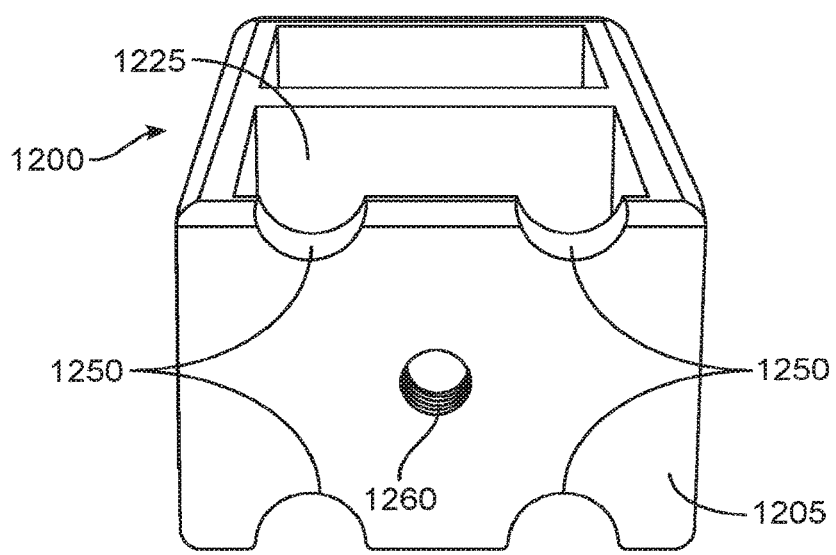
FIG. 12B depicts an angled side view.
Figure 12C:
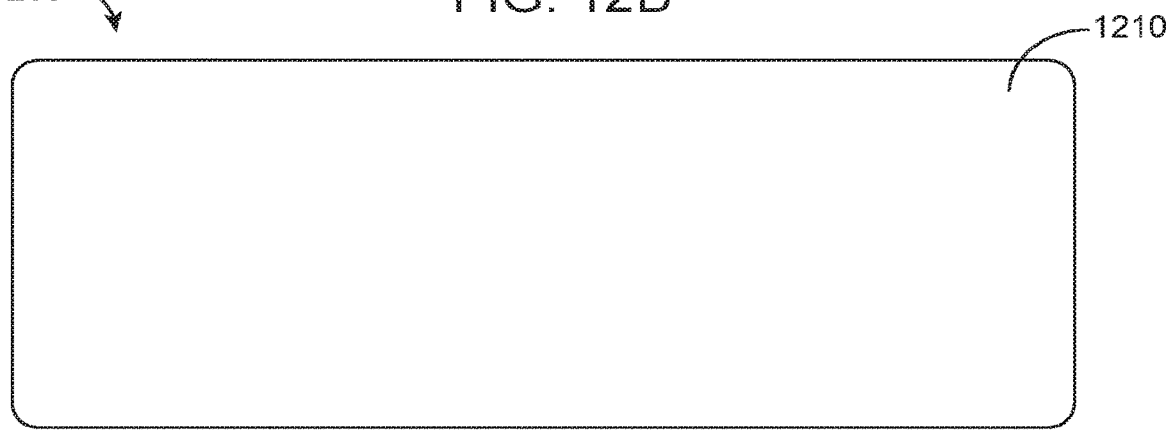
FIG. 12C depicts a front or anterior view of an anterolateral or lateral cage in accordance with an illustrative embodiment.

FIG. 12A depicts an angled top view, FIG. 12B depicts an angled side view, and FIG. 12C depicts a front or anterior view of an anterolateral or lateral cage 1200, in accordance with an illustrative embodiment. Partial holes or bores 1250 are designed to allow free passage of screws or fasteners that will be placed through holes in a lateral plate to secure a lateral plate to a vertebral body or bodies. The partial holes (or partial bores) 1250 can be formed in upper and lower edges of a face of the lateral cage 1200, and can have a semi-circular shape. A lateral cage can include walls 1205, 1210, 1215, 1220, and 1225, or in an alternative embodiment, may include more or fewer walls. Wall 1215 is the leading edge of the cage 1200, in that it is inserted first into the disk space during a surgery, and faces laterally, opposite the surgical wound. Wall 1205 is opposite wall 1215 and faces laterally towards the surgical wound and is the only readily visible part of the cage to the surgeon once it is inserted into the disk space. As an example, if cage 1200 was inserted via a right-sided direct lateral surgical approach, wall 1215 would be the leading edge of insertion and would therefore face the left side of the patient's body, and wall 1205 would face the right side of the patient's body, and would be visible from the surgical wound. Hole 1260 is threaded and accommodates an inserter or a bolt to attach a lateral plate (shown later) to the lateral cage. In an alternative embodiment, hole 1260 may not be threaded, but may be designed to accommodate a fastener that will attach to a lateral plate (shown later).

Figure 13A:
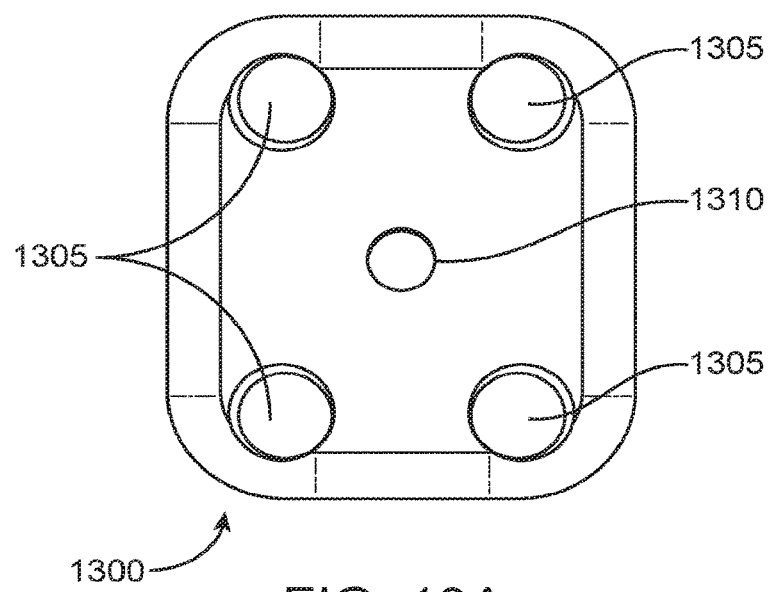
FIG. 13A depicts a lateral side view.
Figure 13B:
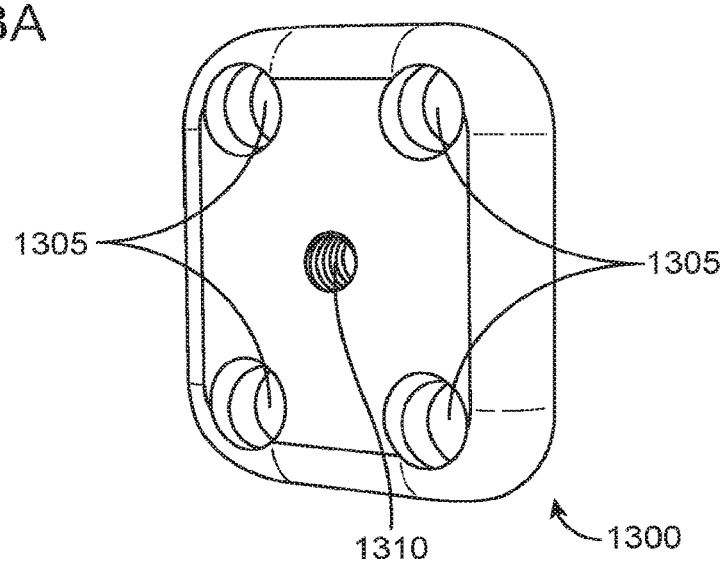
FIG. 13B depicts an angled lateral side view.
Figure 13C:
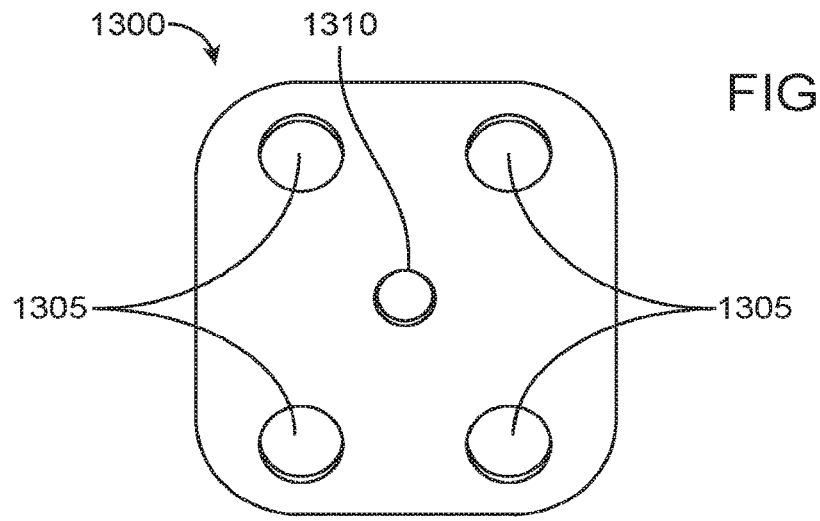
FIG. 13C depicts a medial side view of a lateral plate in accordance with an illustrative embodiment.

FIG. 13A depicts a lateral side view, FIG. 13B depicts an angled lateral side view, and FIG. 13C depicts a medial side view of a lateral plate 1300, in accordance with an illustrative embodiment. In this embodiment, plate 1300 contains four holes 1305 that can accommodate screws or fasteners (not shown), although alternative plate embodiments may contain more or fewer screw holes. These holes 1305 may be henceforth referred to as plate screw holes 1305 or plate holes 1305, although they may accommodate fasteners other than screws. In this embodiment, plate 1300 contains a threaded hole 1310 that receives an inserter (not shown here, see FIG. 15A), though alternative embodiments may contain a different mechanism of attachment of the inserter to the plate. In alternative embodiments, hole 1310 may not be threaded.

Figure 14A:
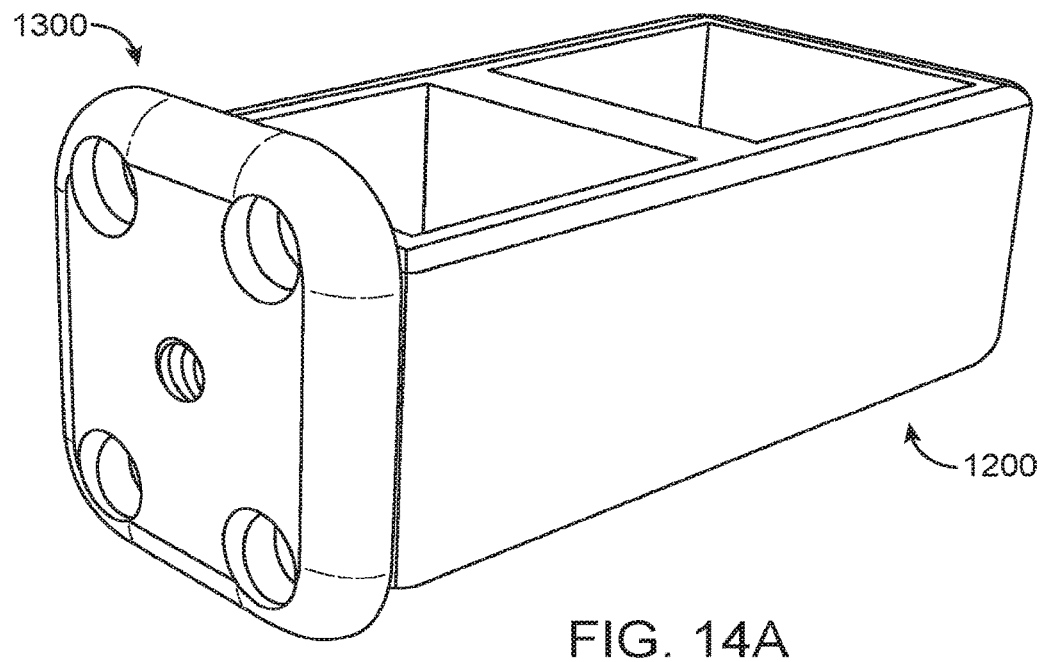
FIG. 14A depicts an angled lateral view of a lateral plate adjacent to a lateral cage in accordance with an illustrative embodiment.

FIG. 14A depicts an angled lateral view of lateral plate 1300 adjacent to lateral cage 1200, in anticipation of being coupled with an inserter (not shown here, see FIG. 15A), in accordance with an illustrative embodiment.

Figure 14B:
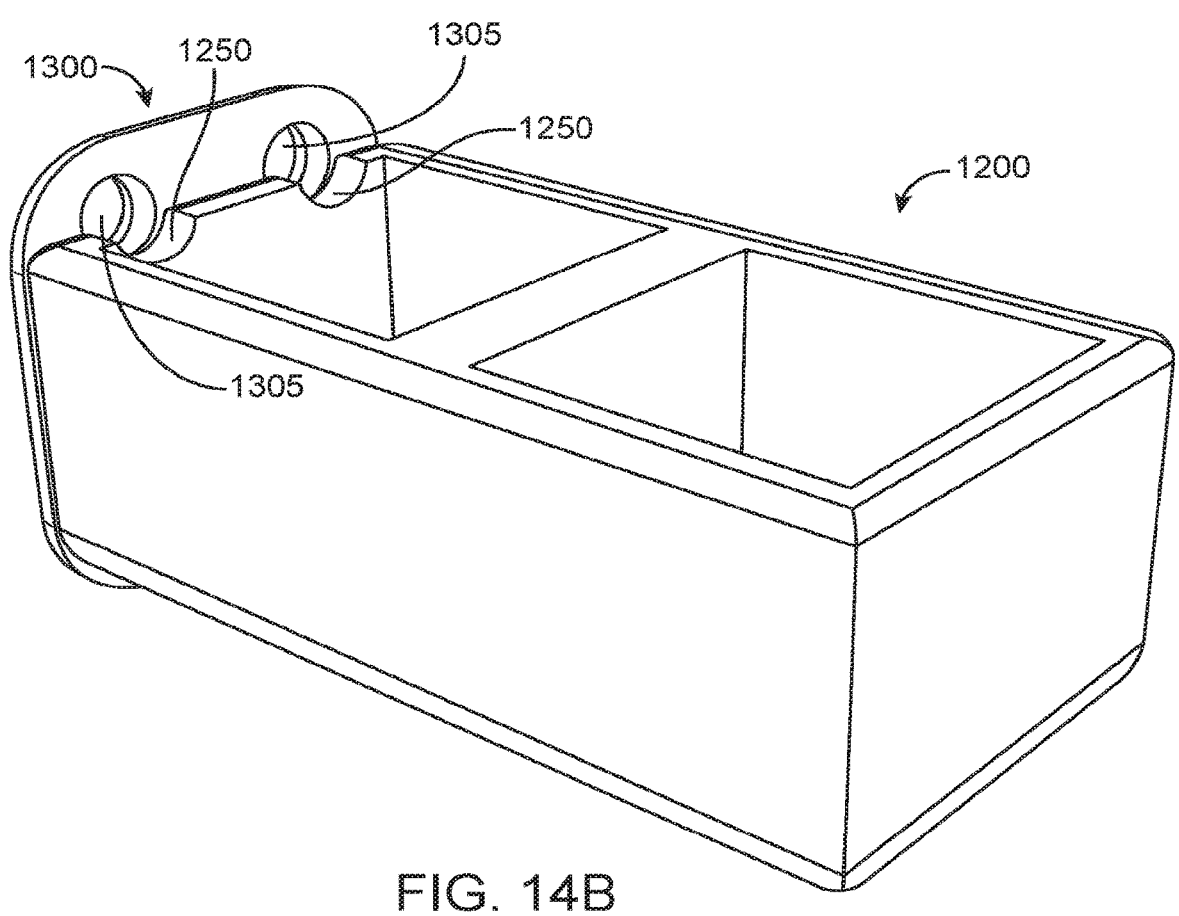
FIG. 14B depicts an angled medial view of the lateral plate adjacent to the lateral cage in accordance with an illustrative embodiment.

FIG. 14B depicts an angled medial view of lateral plate 1300 adjacent to lateral cage 1200, in anticipation of being coupled with an inserter (not shown here, see FIG. 15A), in accordance with an illustrative embodiment. Plate screw holes 1305 line up with partial cage holes or bores 1250, such that a screw or fastener (not shown) placed through lateral plate holes 1305 will pass through the partial cage holes or bores 1250 without engaging lateral cage 1200.

Figure 15A:
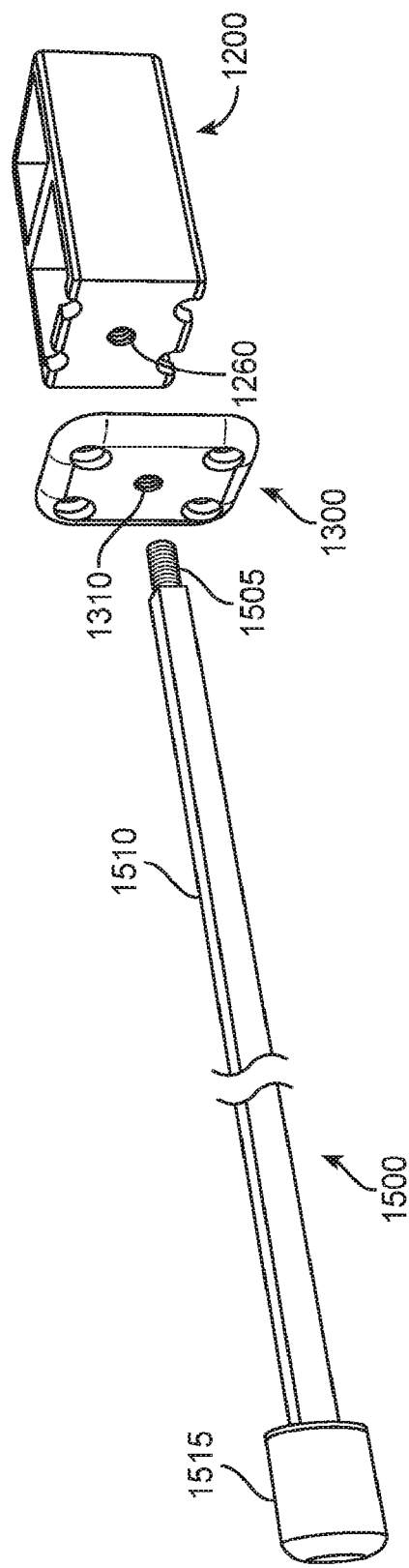
FIG. 15A depicts an inserter, a lateral plate, and a lateral cage in a disassembled configuration in accordance with an illustrative embodiment.

FIG. 15A depicts an angled view of an inserter 1500, lateral plate 1300, and lateral cage 1200 in a disassembled configuration, in accordance with an illustrative embodiment. The Inserter 1500 may be comprised of a threaded terminal end 1505 that will engage lateral plate 1300 and/or lateral cage 1200, a shaft 1510 of variable length, shape, and configuration, and an inserter handle 1515 of variable length, shape, and configuration. Plate 1300 may contain a threaded hole 1310 that receives terminal end 1505 of inserter 1500, though alternative embodiments may contain a different mechanism of attachment of the inserter to the plate. In alternative embodiments, hole 1310 may not be threaded. Lateral cage hole 1260 may be threaded and accepts the threaded terminal end 1505 of inserter 1500 in order to temporarily and reversibly attach lateral plate 1300 to lateral cage 1200 while screws or fasteners (shown later) are placed through plate screw holes into a vertebral body (shown later). Once inserter 1500 is removed, it may be replaced by a connecting bolt (shown later) to attach lateral plate 1300 to lateral cage 1200. In an alternative embodiment, hole 1260 may not be threaded, but may be designed to accommodate a fastener that will attach to the lateral plate.

Figure 15B:
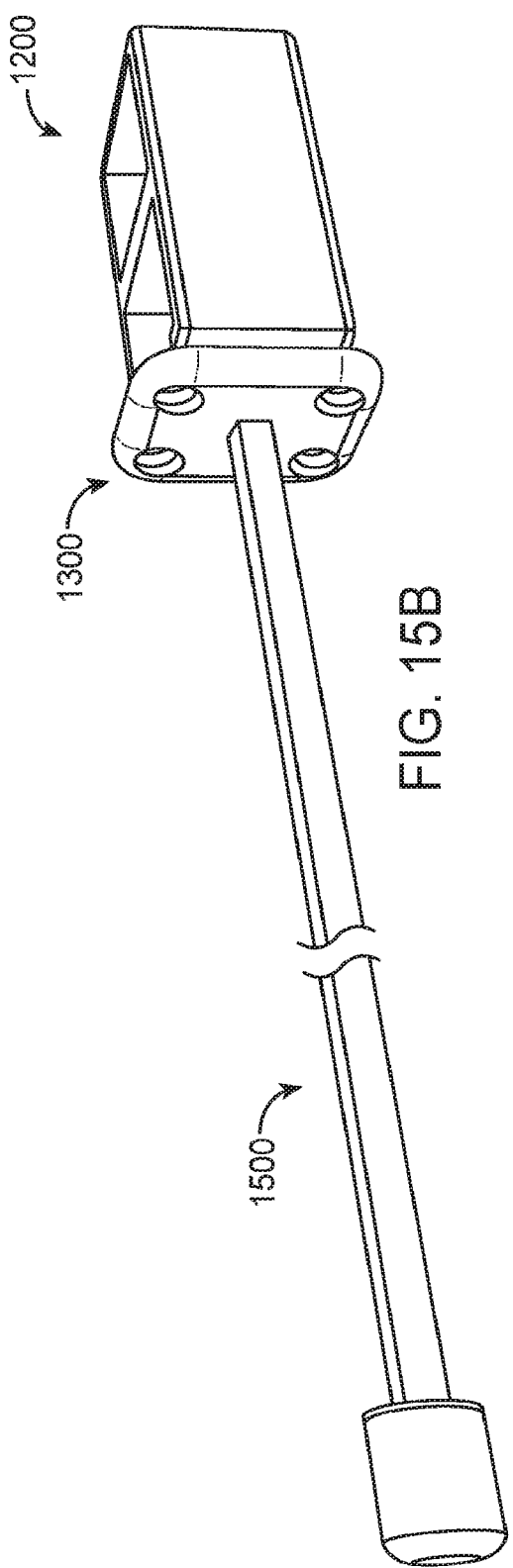

FIG. 15B depicts an angled view of inserter 1500, lateral plate 1300, and lateral cage 1200 in an assembled configuration, in accordance with an illustrative embodiment. Inserter 1500 reversibly anchors lateral plate 1300 to lateral cage 1200, which prevents lateral plate 1300 movement while drill bit or awl 1525 (see FIG. 15D) establishes a screw or fastener pathway in a vertebral body and during screw or fastener insertion into a vertebral body through plate holes (shown later).

FIG. 15C depicts a top angled view of inserter 1500, lateral plate 1300, and lateral cage 1200 in an assembled configuration, in accordance with an illustrative embodiment. Threaded terminal end 1505 of inserter 1500 is shown engaging lateral cage 1200. As threaded terminal end 1505 is screwed into threaded hole 1260 (from FIGS. 12A and 12B) of lateral cage 1200, and the medially-facing wall of lateral plate 1300 is pressed tightly against the laterally-facing wall of lateral cage 1200, anchoring lateral plate 1300 to lateral cage 1200. Depending on whether or not lateral plate hole 1310 (from FIGS. 13A-13C and FIG. 15A) is threaded, threaded terminal end 1505 of inserter 1500 may or may not thread into lateral plate hole 1310, but either way, lateral plate 1300 can be temporarily and reversibly anchored to lateral cage 1200 by inserter 1500.

FIG. 15D depicts a front or anterior view of inserter 1500, lateral plate 1300, lateral cage 1200, a drill bit or awl 1550, and drill bit guide or awl guide 1525 in an assembled configuration, in accordance with an illustrative embodiment. Inserter 1500 anchors lateral plate 1300 to lateral cage 1200, which prevents lateral plate 1300 movement while drill bit or awl 1525 establishes a screw or fastener pathway in a vertebral body (not shown) and during screw or fastener insertion into a vertebral body through plate holes (shown later). In one embodiment, drill bit or awl guide 1525 may include a handle 1530 and a cannulated terminal end 1535 that has a leading end that fits into a screw hole 1305 in lateral plate 1300 (from FIGS. 13A-13C and FIG. 14B). The drill bit or awl guide 1525 accepts and guides drill or awl 1550 through the screw hole into the vertebral body. In one embodiment, drill bit or awl 1550 may include a terminal end 1560 that establishes a screw pathway into a vertebral body and a shaft 1555.

FIG. 16A depicts an angled view of inserter 1500, lateral plate 1300, and lateral cage 1200, now with a screw 350 inserted through a screw hole 1350 (see FIGS. 13A-13C and FIG. 14B) in lateral plate 1300 by screwdriver 1590 into a vertebral body (not shown), in accordance with an illustrative embodiment. Screw 350 is placed through a plate screw hole 1305 (see FIGS. 13A-13C and FIG. 14B) into a screw pathway in a vertebra that was established by drill bit or awl 1550 (from FIG. 15D). Inserter 1500 reversibly anchors lateral plate 1300 to lateral cage 1200, which prevents lateral plate 1300 movement while screw or fastener pathways are established and screws 350 are placed into a vertebra.

FIG. 16B depicts an angled view of inserter 1500, lateral plate 1300, lateral cage 1200, and screws 350 inserted through plate 1300 into a vertebral body, in accordance with an illustrative embodiment. Screw heads 370 engage plate 1300, firmly pressing lateral plate 1300 to the outer cortex of a vertebra as the screws are fully inserted and tightened in the vertebra.

Figure 16C:
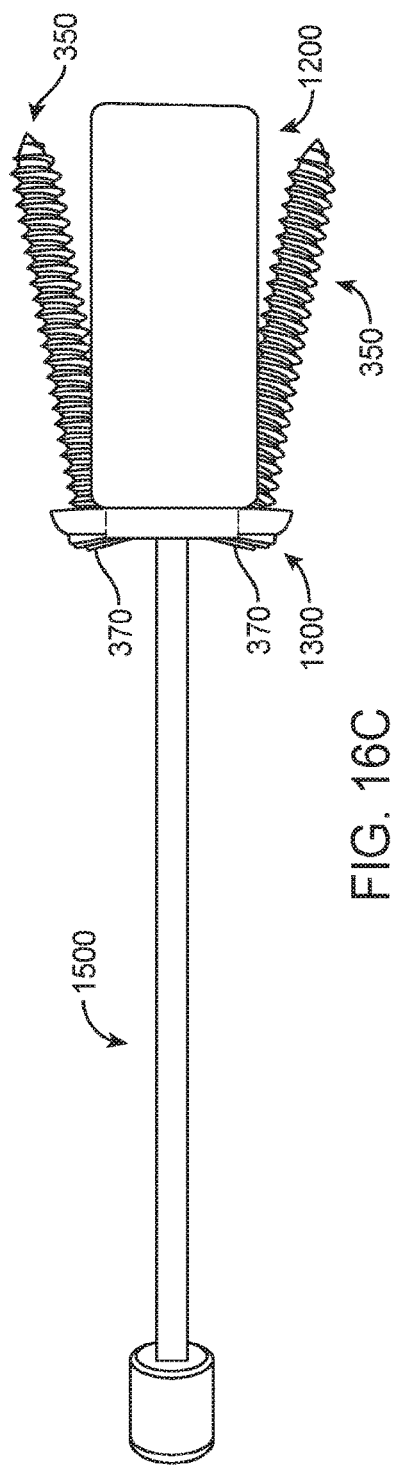

FIG. 16C depicts a front or anterior view of inserter 1500, lateral plate 1300, lateral cage 1200, and screws 350 inserted through plate holes 1305 (see FIGS. 13A-13C and FIG. 14B) in plate 1300 into a vertebral body, in accordance with an illustrative embodiment. Screw heads 370 engage plate 1300, firmly pressing lateral plate 1300 to the outer cortex of a vertebra as the screws are fully inserted and tightened in the vertebra.

Figure 16D:
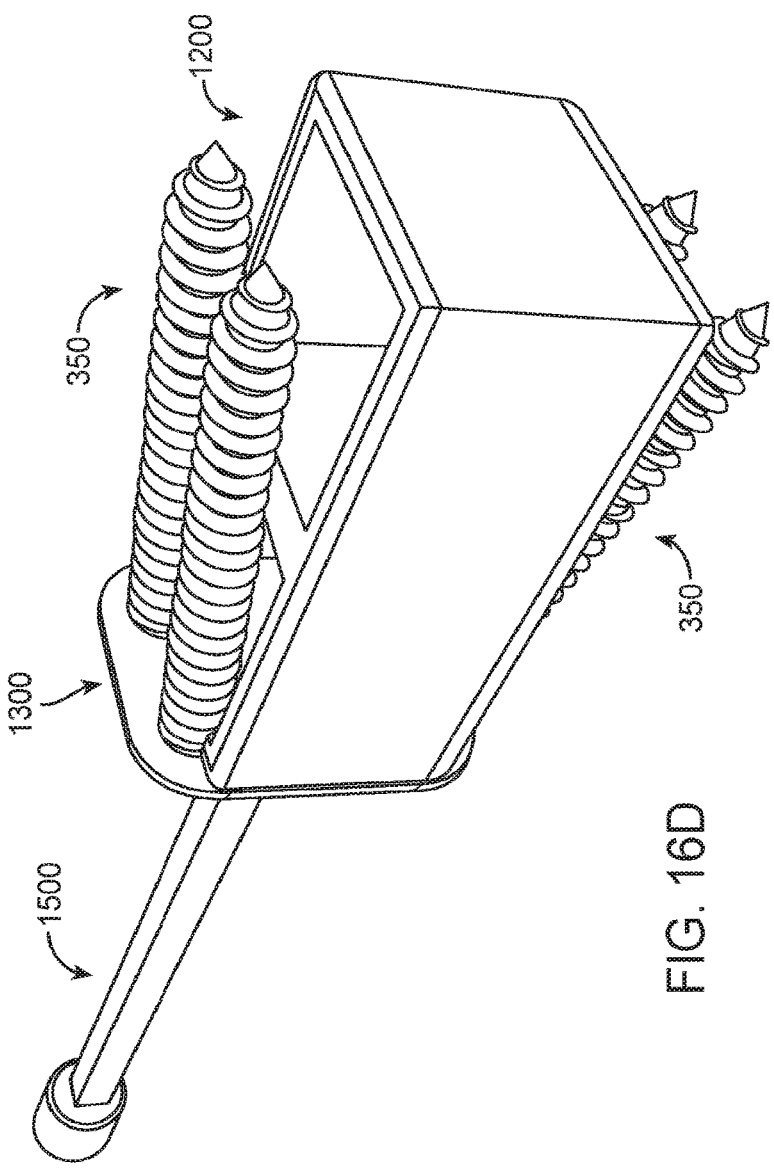

FIG. 16D depicts an angled top view of inserter 1500, lateral plate 1300, lateral cage 1200, and screws 350 inserted through plate 1300 into a vertebral body, in accordance with an illustrative embodiment. Screw heads 370 (see FIGS. 16A-16C) engage plate 1300, firmly pressing lateral plate 1300 to the outer cortex of a vertebra (not shown) as the screws are fully inserted and tightened in the vertebra. Plate screw holes 1305 (see FIGS. 13A-13C and FIG. 14B) line up with partial cage holes or bores 1250 (see FIG. 14B), such that a screw 350 placed through lateral plate 1300 will pass through the cage holes or bores 1250 (see FIG. 14B) without engaging lateral cage 1200.

Figure 17A:
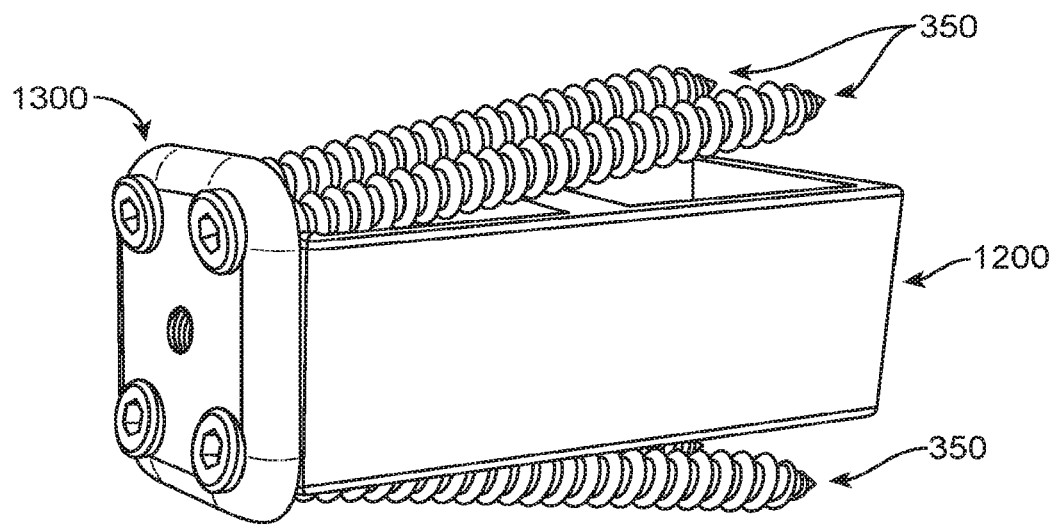
FIGS. 17A-17C depict a lateral plate and a lateral cage with screws engaging the lateral plate and passing freely through bores in the wall of the lateral cage, with the inserter removed, in accordance with illustrative embodiments.
Figure 17B:
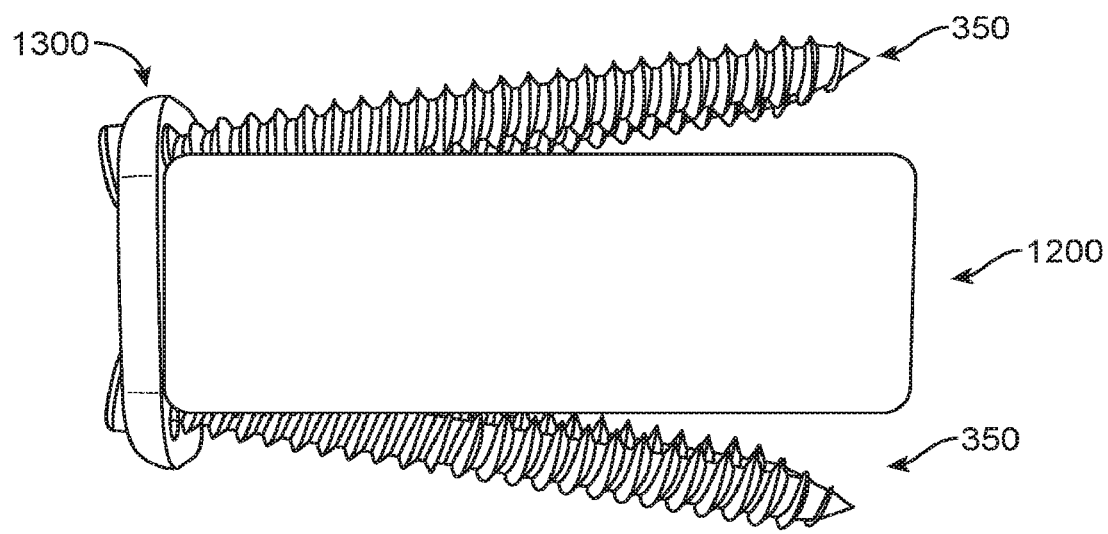

FIG. 17A depicts an angled view and FIG. 17B depicts a front or anterior view of lateral plate 1300, lateral cage 1200, and screws 350 inserted through screw holes 1305 (see FIGS. 13A-13C and FIG. 14B) in lateral plate 1300 into vertebral bodies (not shown) cephalad and caudal to lateral cage 1200, in accordance with an illustrative embodiment. Inserter 1500 (from FIGS. 15A-15D) has been removed, decoupling lateral plate 1300 from lateral cage 1200. In this embodiment, lateral plate 1300 is not anchored to lateral cage 1200, thus allowing lateral plate 1300 and lateral cage 1200 to experience independent biomechanical forces as a patient moves. In alternative embodiments (see FIG. 18B), lateral plate 1300 may be anchored to lateral cage 1200 via a bolt 1800 or other connecting mechanism, in which case lateral plate 1300 and lateral cage 1200 are subject to and experience the same biomechanical forces as a patient moves.

Figure 17C:
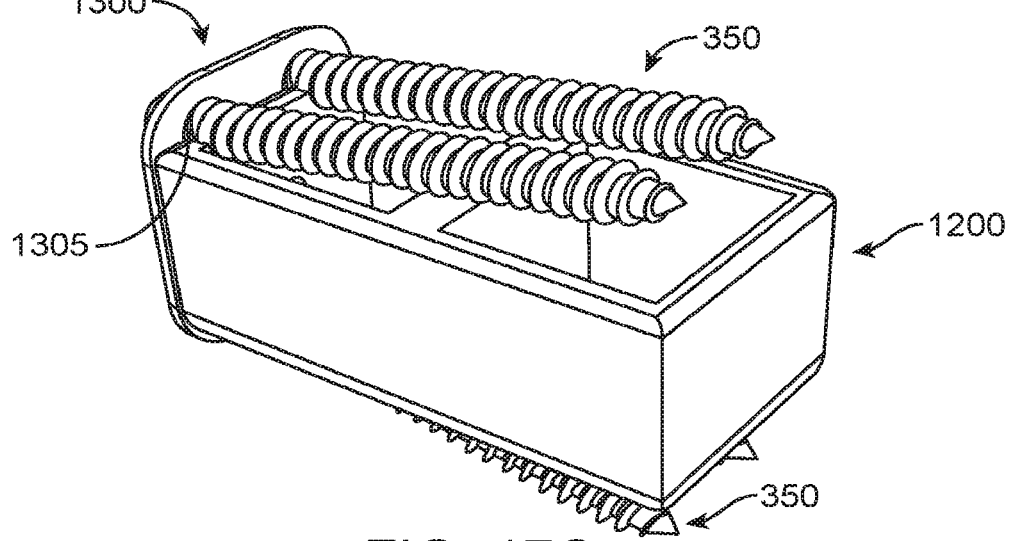

FIG. 17C depicts an angled top view of lateral plate 1300, lateral cage 1200, and screws 350 inserted through screw holes 1305 (see FIGS. 13A-13C and FIG. 14B) in plate 1300 into vertebral bodies cephalad and caudal to lateral cage 1200, in accordance with an illustrative embodiment. The inserter 1500 (from FIGS. 15A-15D) has been removed, decoupling lateral plate 1300 from lateral cage 1200. Plate screw holes 1305 (see FIGS. 13A-13C and FIG. 14B) line up with cage holes or bores 1250 (see FIG. 14B), such that a screw 350 placed through lateral plate 1300 will pass through the partial cage holes or bores 1250 (see FIG. 14B) without engaging lateral cage 1200.

Figure 18A:
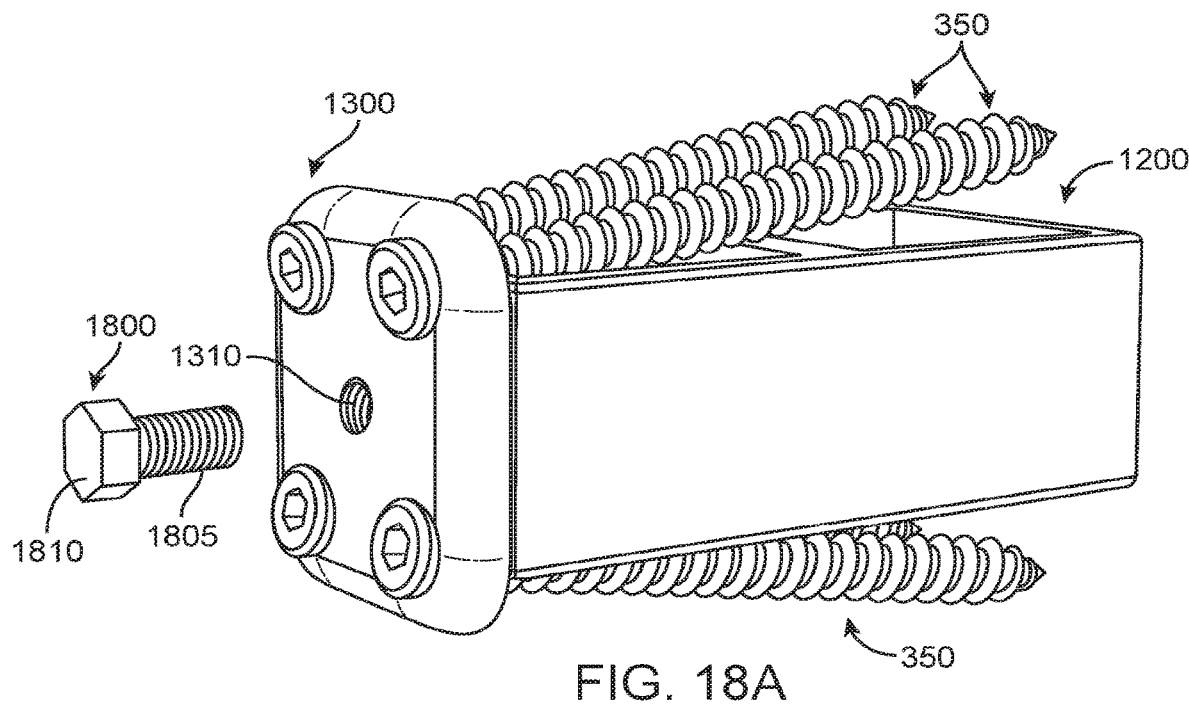
FIG. 18A depicts a lateral plate and a lateral cage with screws engaging the lateral plate and passing freely through bores in the wall of the lateral cage, with a bolt that connects the plate to the cage in a disassembled configuration, in accordance with an illustrative embodiment.

FIG. 18A depicts an angled view of lateral plate 1300 with plate hole 1310, lateral cage 1200, screws 350 inserted through screw holes 1305 (see FIGS. 13A-13C and FIG. 14B) in plate 1300 into vertebral bodies (not shown) cephalad and caudal to lateral cage 1200, and a connecting bolt 1800 in a disassembled configuration, in accordance with an illustrative embodiment. In one embodiment, connecting bolt 1800 may be comprised of a threaded shaft 1805 and a head 1810.

Figure 18B:
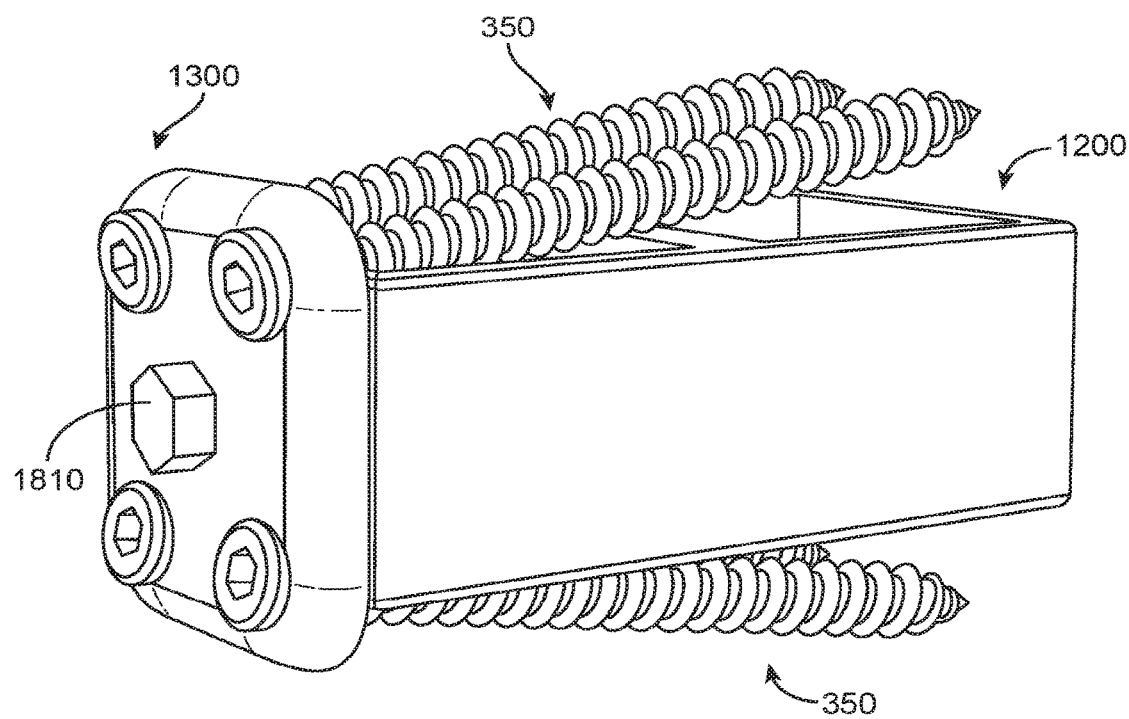
FIG. 18B depicts a lateral plate and a lateral cage with screws engaging the lateral plate and passing freely through bores in the wall of the lateral cage, with a bolt connecting the plate to the cage in an assembled configuration, in accordance with an illustrative embodiment.

FIG. 18B depicts an angled view of lateral plate 1300, lateral cage 1200, screws 350 inserted through plate 1300 into vertebral bodies cephalad and caudal to lateral cage 1200, and a connecting bolt 1800 in an assembled configuration, in accordance with an illustrative embodiment. Connecting bolt 1800 may thread through both lateral plate hole 1310 (see FIG. 18A) and lateral cage hole 1260 (from FIGS. 12A-12B), thus anchoring lateral plate 1300 to lateral cage 1200; or if lateral plate hole 1310 is not threaded, connecting bolt 1800 may pass through lateral plate hole 1310 and thread into lateral cage hole 1260 (from FIGS. 12A-12B) and press the medially-facing wall of lateral plate 1300 firmly to the laterally-facing wall of lateral cage 1200, thus anchoring lateral plate 1300 to lateral cage 1200. When lateral plate 1300 is connected to lateral cage 1200 by connecting bolt 1800 or other connecting mechanism, lateral plate 1300 and lateral cage 1200 are subject to and experience the same biomechanical forces as a patient moves.

Figure 19A:
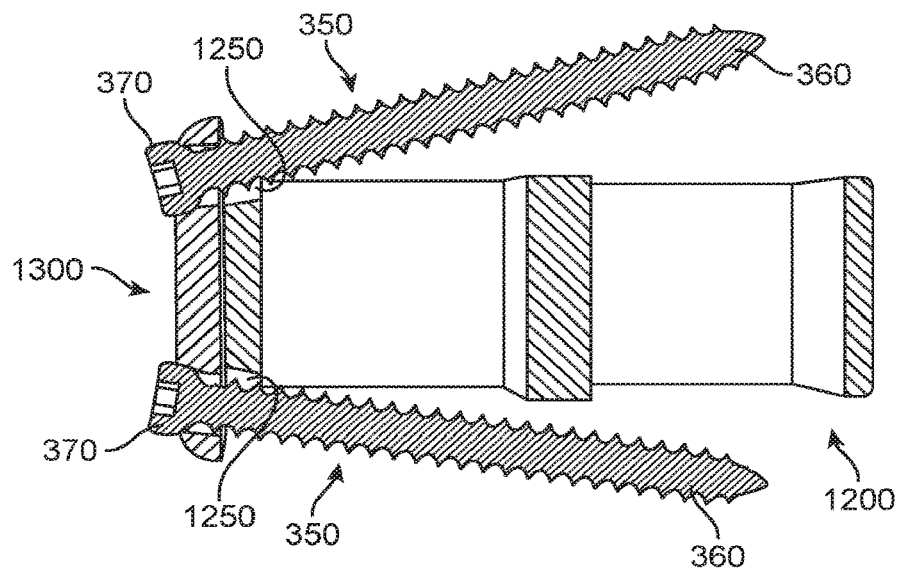
FIG. 19A depicts a cross section of a lateral plate and a lateral cage with screws engaging the lateral plate and passing freely through bores in the wall of the lateral cage, in accordance with an illustrative embodiment.

FIG. 19A depicts a front or anterior view of a cross section of lateral plate 1300 and lateral cage 1200 with screws 350 passing through lateral plate screw holes 1305 (see FIGS. 13A-13C and FIG. 14A) with screw heads 370 engaging lateral plate 1300 and screw shafts 360 passing freely through holes or bores 1250 in a wall of lateral cage 1200, in accordance with an illustrative embodiment.

Figure 19B:
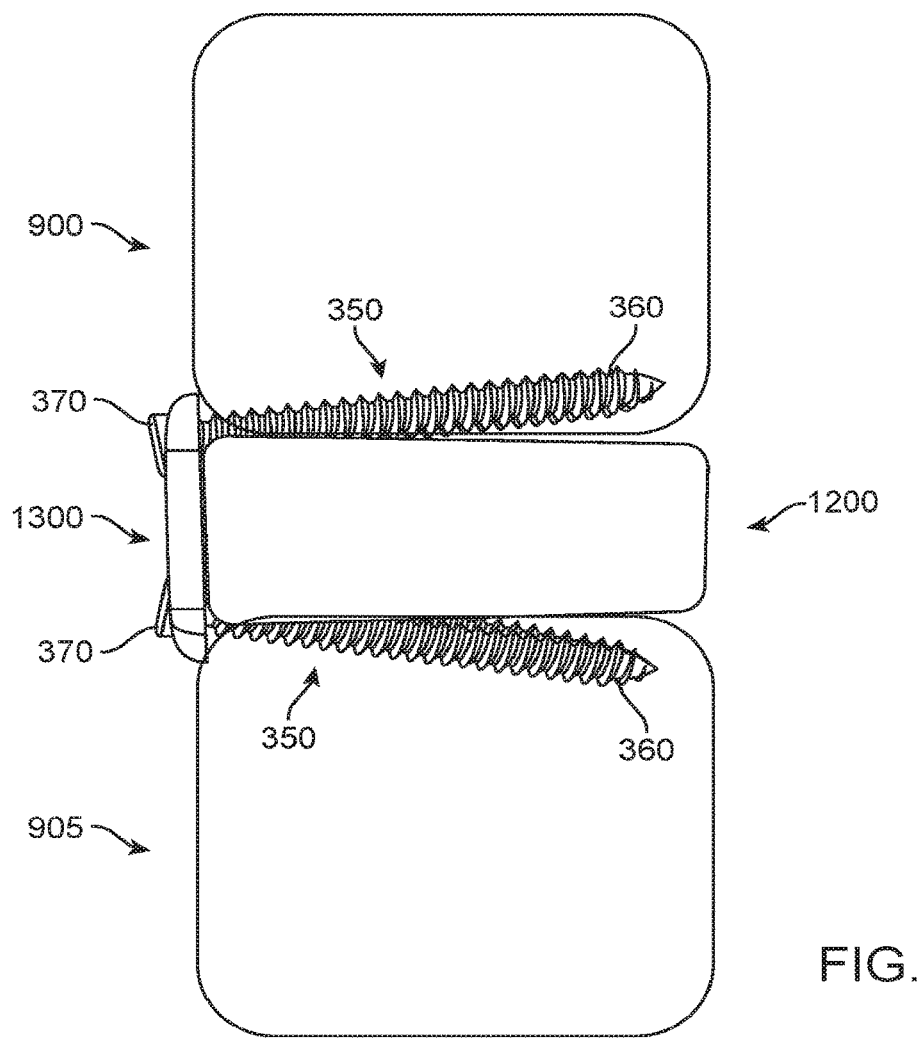
FIG. 19B depicts a lateral plate and a lateral cage with screws engaging the lateral plate and passing freely through bores in the wall of the lateral cage and anchoring in vertebral bodies cephalad and caudal to the lateral cage, in accordance with an illustrative embodiment.

FIG. 19B depicts a front or anterior view of lateral plate 1300 and lateral cage 1200 with screws 350 passing through lateral plate screw holes 1305 (see FIGS. 13A-13C and FIG. 14A) with screw heads 370 engaging lateral plate 1300 and screw shafts 360 passing freely through partial holes or bores 1250 in the wall of lateral cage 1200 (see FIG. 19A) and anchoring into cephalad vertebra 900 and caudal vertebra 905, in accordance with an illustrative embodiment. Lateral cage 1200 is inserted into the disk space between vertebra 900 and 905. Lateral plate 1300 is pressed against the outer cortex of vertebra 900 and 905 by the screws that are anchored in the vertebral bodies of vertebra 900 and 905. In this embodiment, lateral plate 1300 is not anchored to lateral cage 1200, thus allowing lateral plate 1300 and lateral cage 1200 to experience independent biomechanical forces as a patient moves. In alternative embodiments (see FIGS. 18B and 21E), lateral plate 1300 may be anchored to lateral cage 1200 via a bolt 1800 or other connecting mechanism, in which case lateral plate 1300 and lateral cage 1200 would be subject to the same biomechanical forces as a patient moves.

Figure 20A:
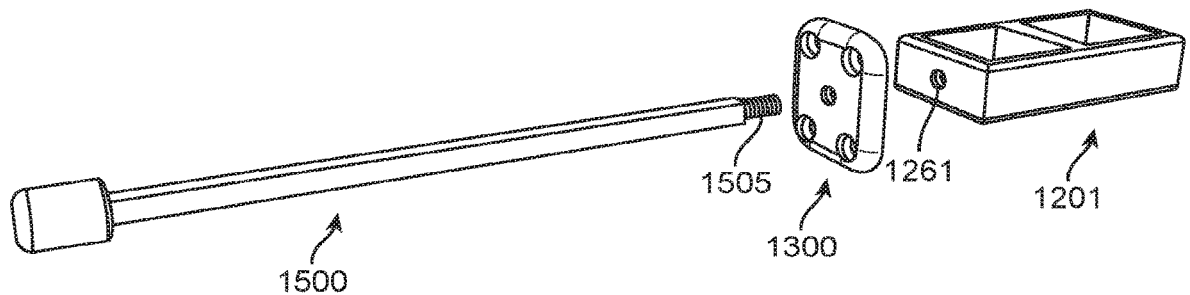
FIG. 20A depicts an inserter, a lateral plate, and a lateral cage in a disassembled configuration in accordance with an illustrative embodiment.

FIG. 20A depicts an angled lateral view of an inserter 1500, lateral plate 1300, and an alternative embodiment of a lateral cage 1201 in a disassembled configuration, in accordance with an illustrative embodiment. Lateral cage 1201 does not include partial (or complete) holes or bores in the lateral-facing wall as does cage 1200 (see FIGS. 12A-12C), but otherwise is structurally and functionally comparable. Lateral cage hole 1261 may be threaded and may accept the threaded terminal end 1505 of inserter 1500 or a bolt (shown later) to attach lateral plate 1300 to lateral cage 1201. In an alternative embodiment, hole 1261 may not be threaded, but may be designed to accommodate a fastener that will attach to a lateral plate and/or an inserter (shown later).

Figure 20B:
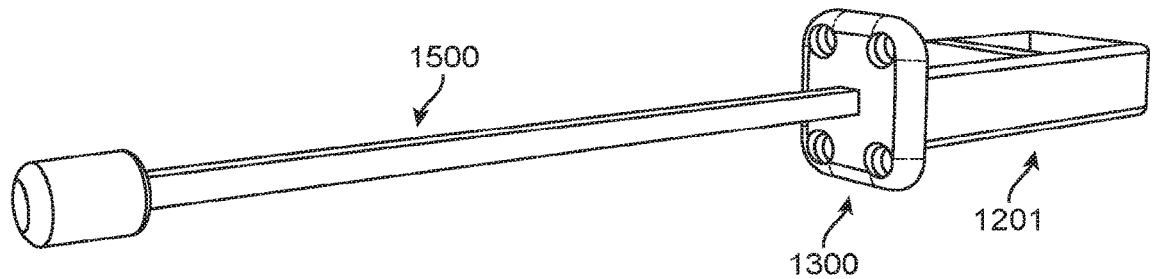
FIGS. 20B-20D depict an inserter, a lateral plate, and a lateral cage in an assembled configuration in accordance with illustrative embodiments.
Figure 20C:
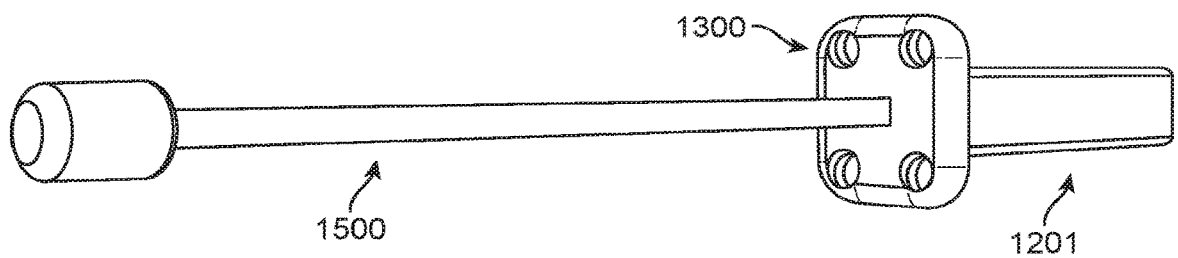
Figure 20D:
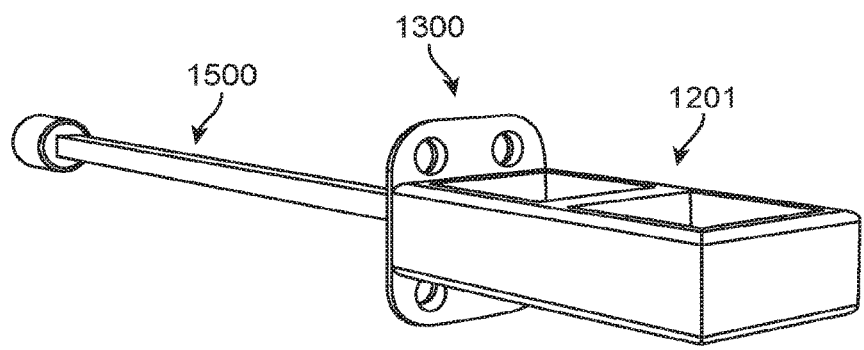

FIGS. 20B-20C depict angled lateral views and FIG. 20D depicts an angled medial view of an inserter 1500, lateral plate 1300, and lateral cage 1201 in an assembled configuration, in accordance with illustrative embodiments. Inserter 1500 reversibly anchors lateral plate 1300 to lateral cage 1201, which prevents lateral plate 1300 movement while a drill bit or awl 1525 (see FIG. 15D) establishes a screw or fastener pathway in a vertebral body (not shown) and during screw or fastener insertion into a vertebral body through holes in lateral plate 1300 (see FIGS. 16A-16B).

FIG. 21A depicts a front or anterior view of inserter 1500, lateral plate 1300, lateral cage 1201, and screws 350 inserted through plate holes 1305 (see FIGS. 13A-13C and FIG. 14A) in lateral plate 1300 into vertebral bodies (not shown) cephalad and caudal to cage 1201, in accordance with an illustrative embodiment.

FIG. 21B depicts a front or anterior view and FIG. 21C depicts an angled view of lateral plate 1300, lateral cage 1201, and screws 350 inserted through plate holes 1305 (see FIGS. 13A-13C and FIG. 14A) in lateral plate 1300 into vertebral bodies (not shown) cephalad and caudal to cage 1201, in accordance with an illustrative embodiment. Inserter 1500 (from FIG. 21A) has been removed, decoupling lateral plate 1300 from lateral cage 1201. In this embodiment, lateral plate 1300 is not anchored to lateral cage 1201, thus allowing lateral plate 1300 and lateral cage 1201 to experience independent biomechanical forces as a patient moves. In alternative embodiments (see FIG. 21E), lateral plate 1300 may be anchored to lateral cage 1200 via a bolt 1800 (see FIG. 21D) or other connecting mechanism, in which case lateral plate 1300 and lateral cage 1201 would be subject to the same biomechanical forces as a patient moves. Screws 350 pass cephalad and caudal to the most cephalad and caudal surfaces of cage 1201, without partial bores or holes in the cage as in FIG. 16D.

FIG. 21D depicts an angled view of lateral plate 1300 with lateral plate hole 1310, lateral cage 1201, screws 350 inserted through plate holes 1305 (see FIGS. 13A-13C and FIG. 14A) in lateral plate 1300 into vertebral bodies cephalad and caudal to cage 1201, and a connecting bolt 1800 in a disassembled configuration, in accordance with an illustrative embodiment.

FIG. 21E depicts an angled view of lateral plate 1300, lateral cage 1201, screws 350 inserted through plate holes 1305 (see FIGS. 13A-13C and FIG. 14A) in plate 1300 into vertebral bodies (not shown) cephalad and caudal to cage 1201, and a connecting bolt 1800 in an assembled configuration, in accordance with an illustrative embodiment. Connecting bolt 1800 may thread through both lateral plate hole 1310 (see FIG. 21D) and lateral cage hole 1261 (from FIG. 20A), thus anchoring lateral plate 1300 to lateral cage 1201; or in an alternative embodiment, if lateral plate hole 1310 is not threaded, connecting bolt 1800 may pass through lateral plate hole 1310 and thread into lateral cage hole 1261, and by virtue of the head 1810 (see FIG. 18A) of connecting bolt 1800 contacting the laterally-facing wall of lateral plate 1300 as connecting bolt 1800 is advanced into lateral plate hole 1310, presses the medially-facing wall of lateral plate 1300 firmly to the laterally-facing wall of lateral cage 1201, thus anchoring lateral plate 1300 to lateral cage 1201 via frictional forces.

Figure 22A:
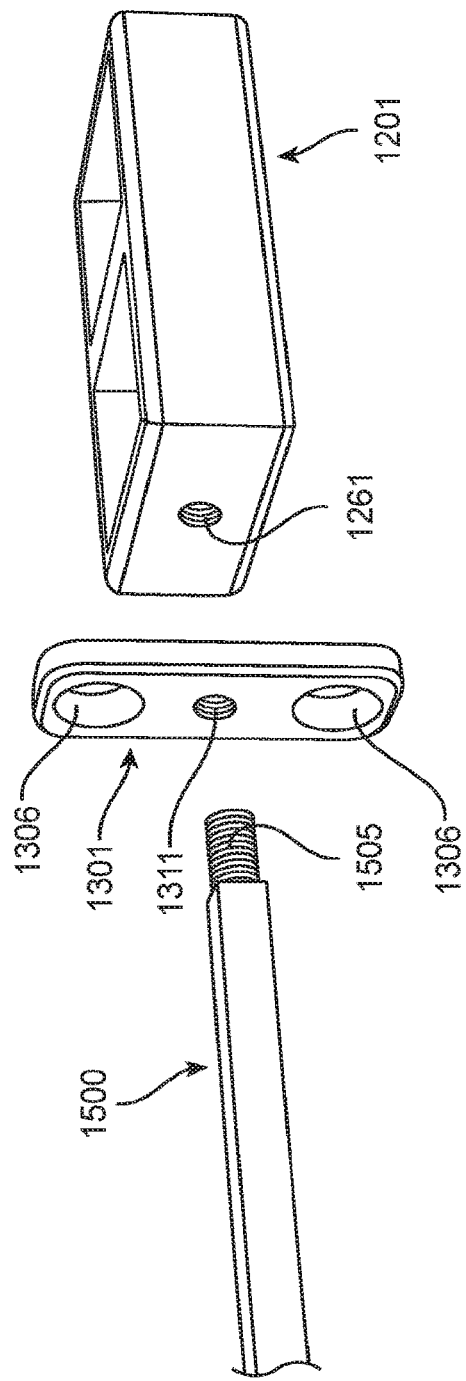
FIG. 22A depicts an inserter, a lateral plate, and a lateral cage in a disassembled configuration in accordance with an illustrative embodiment.

FIG. 22A depicts an angled view of inserter 1500, an alternative embodiment of a lateral plate 1301, and a lateral cage 1201 in a disassembled configuration, in accordance with an illustrative embodiment. Lateral plate 1301 includes a threaded hole 1311 and holes 1306 which will accept screws 350 (shown later). In an alternative embodiment, hole 1311 may not be threaded. Lateral cage threaded hole 1261 accepts the threaded terminal end 1505 of inserter 1500 or a connecting bolt (shown later) to attach lateral plate 1301 to lateral cage 1201. In an alternative embodiment, hole 1261 may not be threaded, but may be designed to accommodate a fastener that will attach to a lateral plate and/or an inserter (shown later).

Figure 22B:
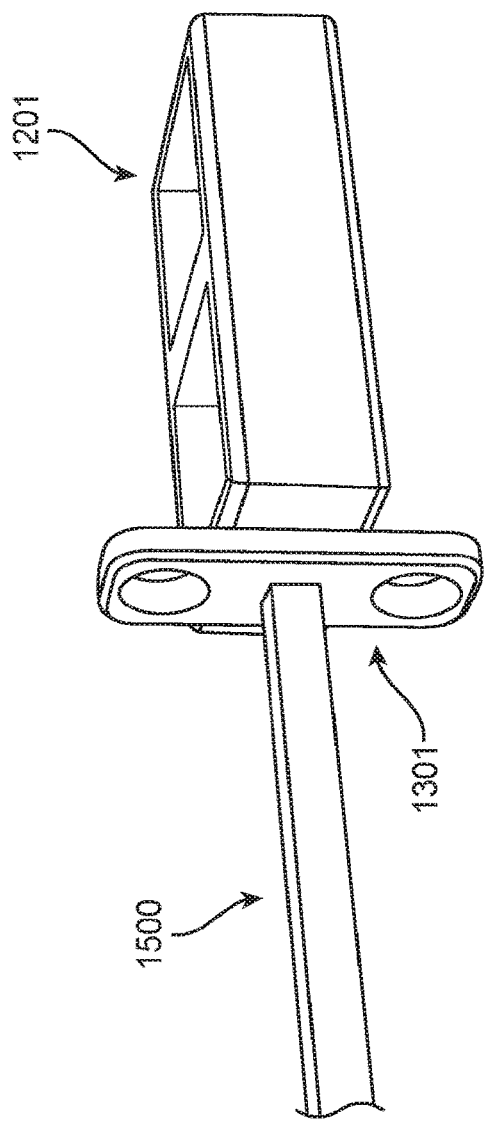
FIG. 22B depicts an inserter, a lateral plate, and a lateral cage in an assembled configuration in accordance with an illustrative embodiment.

FIG. 22B depicts an angled view of inserter 1500, lateral plate 1301, and lateral cage 1201 in an assembled configuration, in accordance with an illustrative embodiment. Inserter 1500 reversibly anchors lateral plate 1301 to lateral cage 1201, which prevents lateral plate 1301 movement while a drill bit or awl 1525 (see FIG. 15D) establishes a screw or fastener pathway in a vertebral body (not shown) and during screw or fastener insertion into a vertebral body through holes in the plate (see FIGS. 16A-16B).

FIG. 22C depicts an angled view of inserter 1500, lateral plate 1301, lateral cage 1201, and screws 350 inserted through plate holes (see FIGS. 13A-13C) in plate 1301 into vertebral bodies (not shown) cephalad and caudal to cage 1201, in accordance with an illustrative embodiment.

FIG. 22D depicts an angled view of lateral plate 1301 with plate hole 1311, lateral cage 1201, screws 350 inserted through plate 1301 into vertebral bodies (not shown) cephalad and caudal to lateral cage 1201, in accordance with an illustrative embodiment. In this embodiment, inserter 1500 has been removed, and lateral plate 1301 is not anchored to lateral cage 1201, thus allowing lateral plate 1301 and lateral cage 1201 to experience independent biomechanical forces as a patient moves. In alternative embodiments (see FIG. 22E), lateral plate 1301 may be anchored to lateral cage 1201 via a bolt 1800 or other connecting mechanism, in which case lateral plate 1301 and lateral cage 1201 would be subject to the same biomechanical forces as a patient moves.

FIG. 22E depicts an angled view of lateral plate 1301, lateral cage 1201, and screws 350 inserted through plate 1301 into vertebral bodies (not shown) cephalad and caudal to lateral cage 1201, in accordance with an illustrative embodiment. Connecting bolt 1800 is threaded through both lateral plate hole 1311 (see FIG. 22D) and lateral cage hole 1261 (see FIG. 22A), thus anchoring lateral plate 1301 to lateral cage 1201; or in an alternative embodiment, if lateral plate hole 1311 is not threaded, connecting bolt 1800 may pass through lateral plate hole 1311 and thread into lateral cage hole 1261 (see FIG. 22A), and by virtue of head 1810 (see FIG. 18A) of connecting bolt 1800 contacting the laterally-facing wall of lateral plate 1301 as connecting bolt 1800 is advanced into threaded lateral cage hole 1261, presses the medially-facing wall of lateral plate 1301 firmly to the laterally-facing wall of lateral cage 1201, thus anchoring lateral plate 1301 to lateral cage 1201 via frictional forces. When lateral plate 1301 is connected to lateral cage 1201 by connecting bolt 1800 or other connecting mechanism, lateral plate 1301 and lateral cage 1201 are subject to the same biomechanical forces as a patient moves.

Figure 23A:
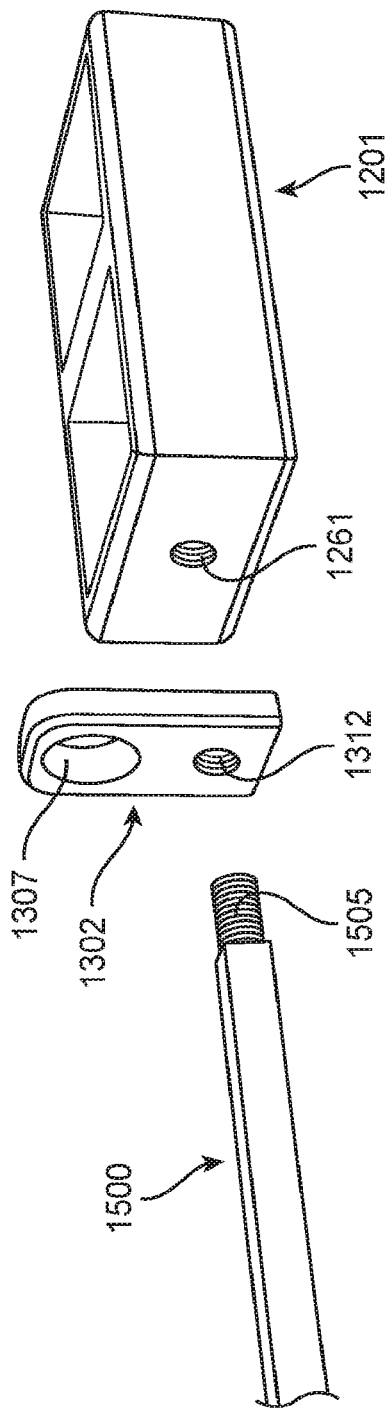
FIG. 23A depicts an inserter, a lateral plate, and a lateral cage in a disassembled configuration in accordance with an illustrative embodiment.

FIG. 23A depicts an angled view of inserter 1500, an alternative embodiment of a lateral plate 1302, and a lateral cage 1201 in a disassembled configuration, in accordance with an illustrative embodiment. Lateral plate 1302 includes a threaded hole 1312, and hole 1307 which will accept a screw 350 (shown later). In an alternative embodiment, lateral plate hole 1312 may not be threaded. Lateral cage threaded hole 1261 accepts the threaded terminal end 1505 of inserter 1500 or a bolt (shown later) to attach lateral plate 1302 to lateral cage 1201. In an alternative embodiment, hole 1261 may not be threaded, but may be designed to accommodate a fastener that will attach to a lateral plate and/or inserter (shown later).

Figure 23B:
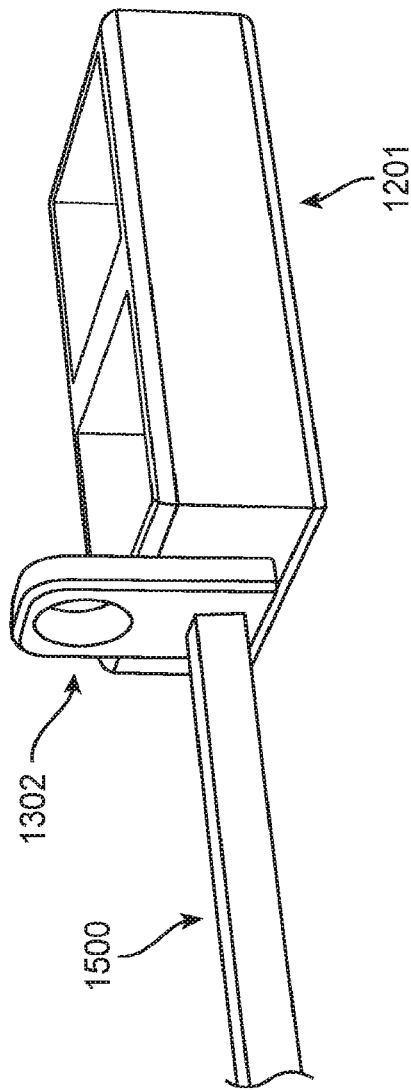
FIG. 23B depicts an inserter, a lateral plate, and a lateral cage in an assembled configuration in accordance with an illustrative embodiment.

FIG. 23B depicts an angled view of inserter 1500, lateral plate 1302, and a lateral cage 1201 in an assembled configuration, in accordance with an illustrative embodiment. Inserter 1500 reversibly anchors lateral plate 1302 to lateral cage 1201, which prevents lateral plate 1302 movement while a drill bit or awl 1525 (see FIG. 15D) establishes a screw or fastener pathway in a vertebral body (not shown) and during screw or fastener insertion into a vertebral body through plate hole 1307 (see FIG. 23A).

Figure 23C:
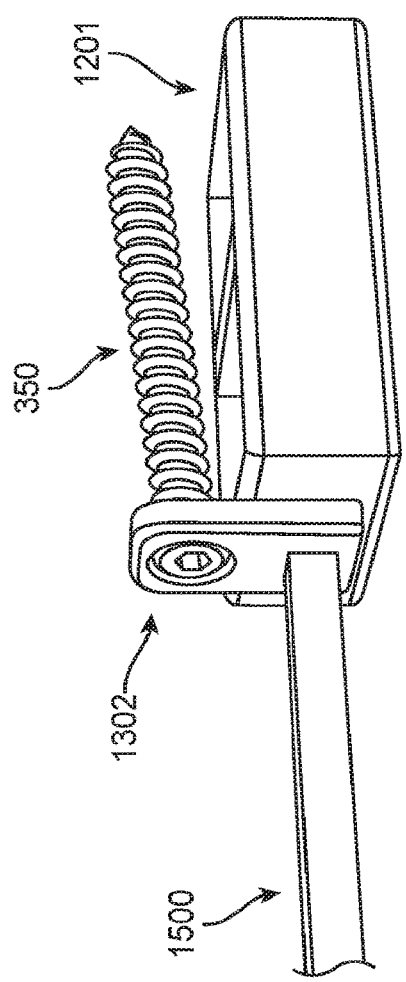
FIG. 23C depicts an inserter, a lateral plate, and a lateral cage in an assembled configuration, with screws placed through and engaging the lateral plate and passing cephalad to the lateral wall of the lateral cage, in accordance with an illustrative embodiment.

FIG. 23C depicts an angled view of inserter 1500, lateral plate 1302, lateral cage 1201, and screw 350 inserted through plate hole 1307 (from FIG. 23A) into the vertebral body (not shown) cephalad to lateral cage 1201, in accordance with an illustrative embodiment. In an alternative embodiment, lateral plate 1302 may be oriented in a manner in which screw 350 is inserted through plate hole 1307 (from FIG. 23A) in lateral plate 1302 into the vertebral body (not shown) caudal to lateral cage 1201.

Figure 23E:
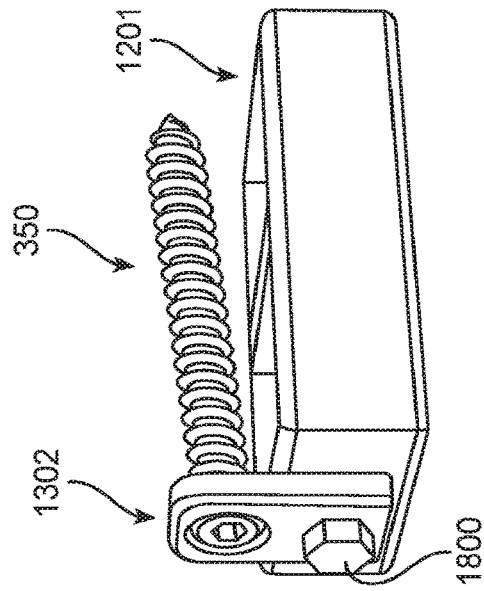
FIG. 23E depicts a lateral plate and a lateral cage with a screw engaging the lateral plate and passing cephalad to the lateral wall of the lateral cage, with a bolt connecting the plate to the cage, in accordance with an illustrative embodiment.
Figure 23D:
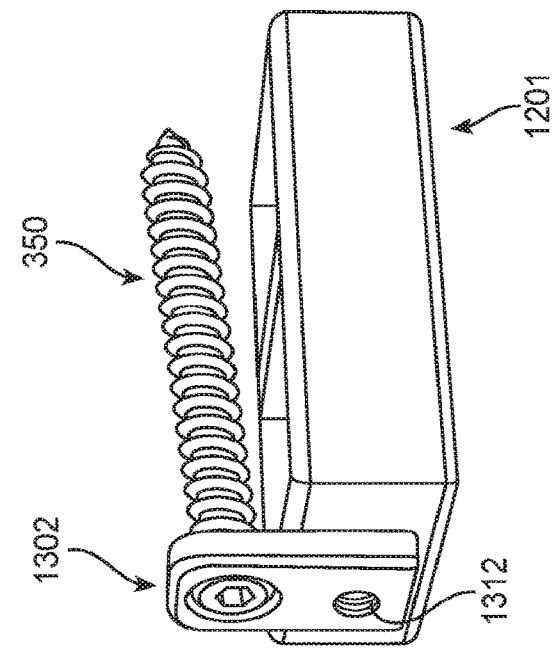
FIG. 23D depicts a lateral plate and a lateral cage with a screw engaging the lateral plate and passing cephalad to the lateral wall of the lateral cage, in accordance with an illustrative embodiment.

FIG. 23D depicts an angled view of lateral plate 1302 with plate hole 1312, lateral cage 1201, screw 350 inserted through plate hole 1307 (see FIG. 23A) into the vertebral body (not shown) cephalad (or in an alternative embodiment, caudal) to lateral cage 1201, in accordance with an illustrative embodiment. In this configuration, lateral plate 1302 is not attached to lateral cage 1201, and serves to prevent migration of lateral cage 1201, i.e., lateral plate 1302 blocks lateral cage 1201 from backing out of the interbody space in a reverse manner from which it was inserted. In this embodiment, inserter 1500 (see FIG. 23C) has been removed, and lateral plate 1302 is not anchored to lateral cage 1201, thus allowing lateral plate 1302 and lateral cage 1201 to experience independent biomechanical forces as a patient moves. In alternative embodiments (see FIG. 23E), lateral plate 1302 may be anchored to lateral cage 1201 via a bolt 1800 or other connecting mechanism, in which case lateral plate 1302 and lateral cage 1201 would be subject to the same biomechanical forces as a patient moves.

FIG. 23E depicts an angled view of lateral plate 1302, lateral cage 1201, screw 350 inserted through plate hole 1307 (see FIG. 23A) into the vertebral body (not shown) cephalad (or in an alternative embodiment, caudal) to lateral cage 1201, in accordance with an illustrative embodiment. Bolt 1800 (see FIG. 21D) has been inserted through plate hole 1312 (see FIG. 23D) and threaded into lateral cage hole 1261 (see FIG. 23A), thus securing lateral plate 1302 to lateral cage 1201. In this configuration, lateral plate 1302 is attached to lateral cage 1201, and serves to prevent migration of lateral cage 1201 in any direction. When lateral plate 1302 is connected to lateral cage 1201 by connecting bolt 1800 or other connecting mechanism, lateral plate 1302 and lateral cage 1201 are subject to the same biomechanical forces as a patient moves.

FIG. 24A depicts an angled view of the medial side of a lateral plate 2400, in accordance with an illustrative embodiment. Lateral plate 2400 is depicted with 4 screw or fastener holes 2405, but alternative embodiments may contain more or fewer screw or fastener holes. Lateral plate 2400 includes a (medially-located) protrusion 2401 that includes a top part 2402 and a bottom part 2403, forming a central hole 2410. Protrusion 2401 is rectangular in shape and, as depicted, the upper and lower edges of protrusion 2401 are chamfered. In alternative embodiments, protrusion 2401 may be a different shape such as a circle, oval, square, etc. and may include fewer or additional sides with or without chamfering. In other alternative embodiments, protrusion 2401 may include more or fewer parts, and hole 2410 may or may not be centrally located and may or may not be threaded. The protrusion 2401 can be included in any of the lateral block plates described herein, and any of the lateral cages described herein can include an opening configured to receive the protrusion 2401.

FIG. 24B depicts an angled top view of a lateral cage 1202, which includes hole 2460 designed to accommodate protrusion 2401 of lateral plate 2400 (from FIG. 24A), in accordance with an illustrative embodiment.

FIG. 24C depicts an angled top view of lateral plate 2400 and lateral cage 1202 in an assembled configuration with protrusion 2401 inserted into lateral cage hole 2460 (from FIG. 24B), in accordance with an illustrative embodiment.

Figure 25A:
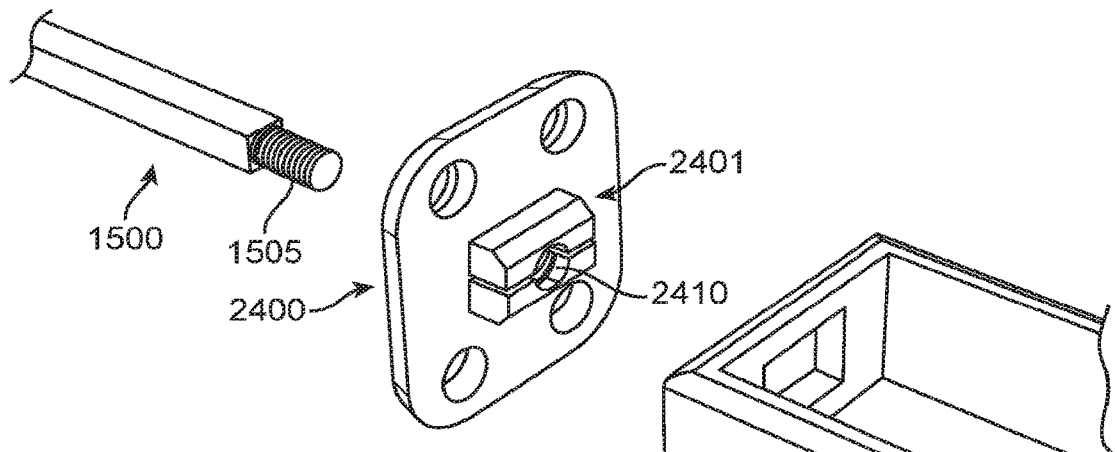
FIG. 25A depicts the alternative embodiment of a lateral plate that engages a lateral cage via a medially-directed protrusion in accordance with an illustrative embodiment.

FIG. 25A depicts an angled top medial view of inserter 1500, lateral plate 2400, and lateral cage 1202, in a disassembled configuration, in accordance with an illustrative embodiment. Threaded inserter end 1505 threads into hole 2410 in lateral plate 2400. In alternative embodiments, inserter end 1505 may not thread into hole 2410, and can instead attach via a press-fit, shape alignment (e.g., a socket connection), magnet-assisted friction fit, etc.

Figure 25B:
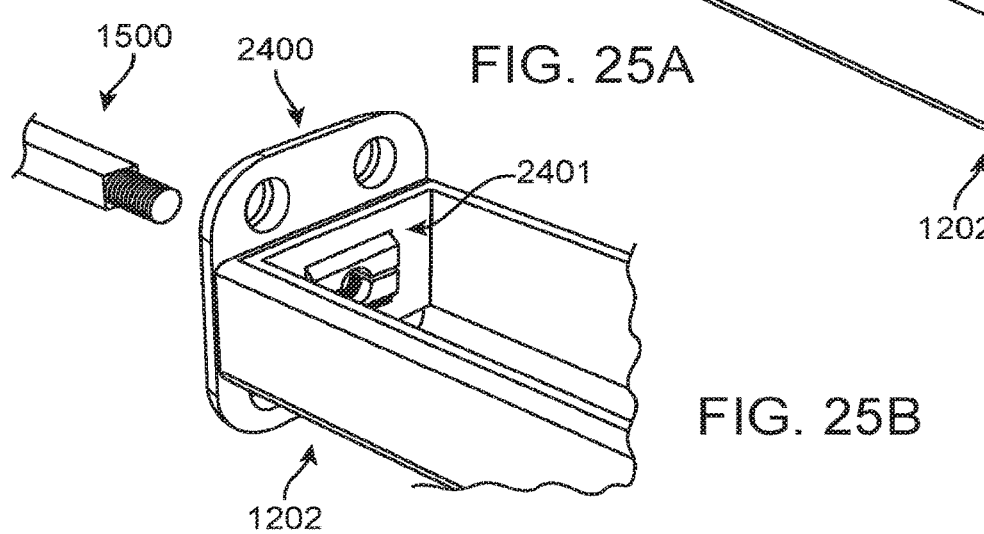
FIG. 25B depicts an inserter, the alternative embodiment of a lateral plate that engages a lateral cage via a medially-directed protrusion, and a lateral cage, in a disassembled configuration, in accordance with an illustrative embodiment.

FIG. 25B depicts an angled top medial view of inserter 1500, lateral plate 2400, and lateral cage 1202, in a partially assembled configuration, with protrusion 2401 inserted into lateral cage hole 2460 (from FIG. 24B), in accordance with an illustrative embodiment.

Figure 25C:
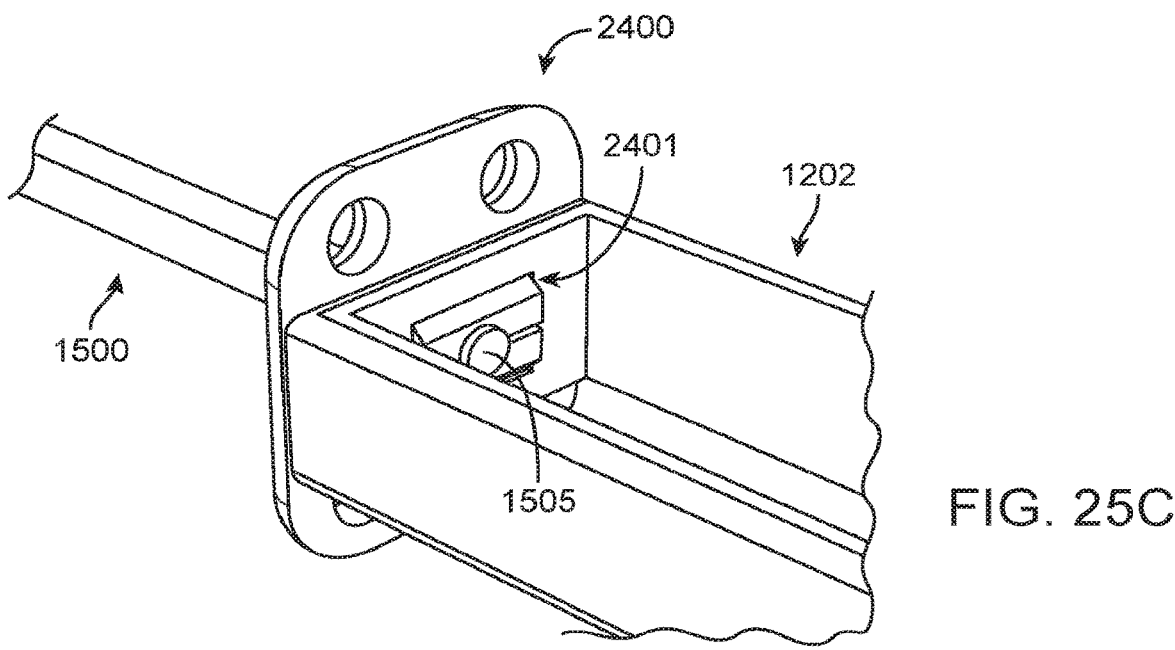
FIG. 25C depicts an inserter, the alternative embodiment of a lateral plate that engages a lateral cage via a medially-directed protrusion, and a lateral cage, in an assembled configuration, in accordance with an illustrative embodiment.

FIG. 25C depicts an angled top medial view of inserter 1500, lateral plate 2400, and lateral cage 1202, in an assembled configuration, with protrusion 2401 inserted into lateral cage hole 2460 (from FIG. 24B), in accordance with an illustrative embodiment. In this embodiment, threaded inserter end 1505 (see FIG. 25A) has been threaded into lateral plate hole 2410 (see FIG. 25A), the act of which pushes top part 2402 (from FIG. 24A) away from bottom part 2403 (from FIG. 24A) of protrusion 2401 (see FIG. 25A), which in turn presses the uppermost surface of part 2402 and the bottommost surface of 2403 against the opposing walls of lateral cage hole 2460 (see FIG. 24B), thus creating a frictional fit of lateral plate 2400 with lateral cage 1202 via protrusion 2401, reversibly coupling lateral plate 2400 with lateral cage 1202. In an alternative embodiment, protrusion 2401 could couple with cage 1202 via a mechanism other than a frictional fit. In one embodiment, top part 2402 and bottom part 2403 of protrusion 2401 can each include a ledge. As a result of expansion of protrusion 2401 due to insertion of threaded inserter end 1505 (or a fastener), the ledges can each contact a portion of the interior wall of the lateral cage 1202 that is adjacent to the lateral cage hole 2460. As such, lateral plate 2400 cannot be detached from lateral cage 1202 until threaded insert end 1505 (or fastener) is removed and protrusion 2401 contracts. Inserter 1500 reversibly anchors lateral plate 2400 to lateral cage 1202, which prevents lateral plate 2400 movement while a drill bit or awl 1525 (see FIG. 15D and FIGS. 26A-26D) establishes a screw or fastener pathway in a vertebral body (not shown) and during screw or fastener insertion into a vertebral body through plate holes 2405 (see FIG. 24A) in lateral plate 2400 (see FIGS. 16A-16B and FIGS. 26C-26D).

Figure 26A:
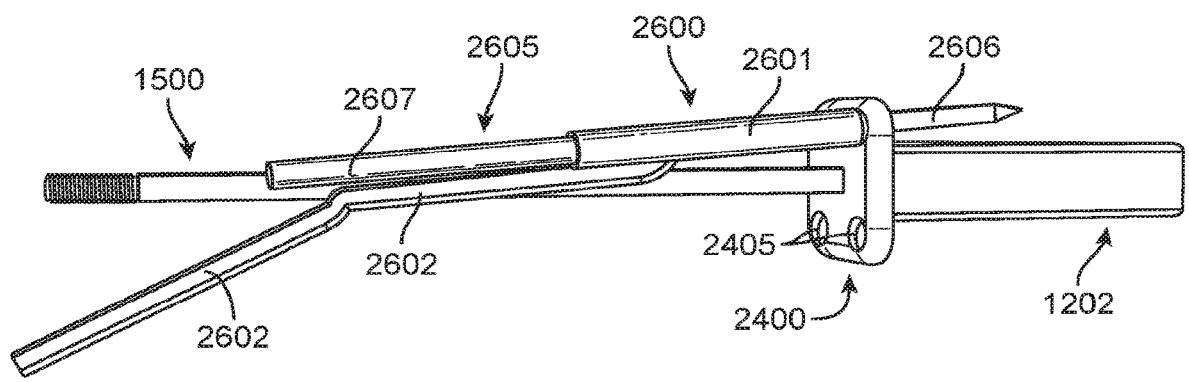
FIGS. 26A-26B depict an inserter, the alternative embodiment of a lateral plate that engages a lateral cage via a medially-directed protuberance, and a lateral cage, in an assembled configuration, in accordance with illustrative embodiments. A drill bit guide, and drill bit or awl used to establish a screw pathway through the plate into a vertebral body, are depicted, in accordance with illustrative embodiments.

FIG. 26A depicts an angled view of lateral cage 1202, lateral plate 2400, and inserter 1500, in an assembled configuration; and awl or drill guide 2600 and awl or drill bit 2605, in accordance with an illustrative embodiment. Drill guide 2600 may include a cannulated portion 2601 that engages a lateral plate hole 2405 (see FIG. 24A) and a handle 2602. Drill bit or awl 2605 may include a shaft portion 2607 and a sharp point 2606 and can establish a screw pathway (not shown) in a vertebral body (not shown). Inserter 1500 reversibly anchors lateral plate 2400 to lateral cage 1202, which prevents lateral plate 2400 movement while drill bit or awl 2605 establishes a screw or fastener pathway in a vertebral body and during screw or fastener insertion into the vertebral body through plate holes 2405 (see FIGS. 26C-26D) in lateral plate 2400.

Figure 26B:
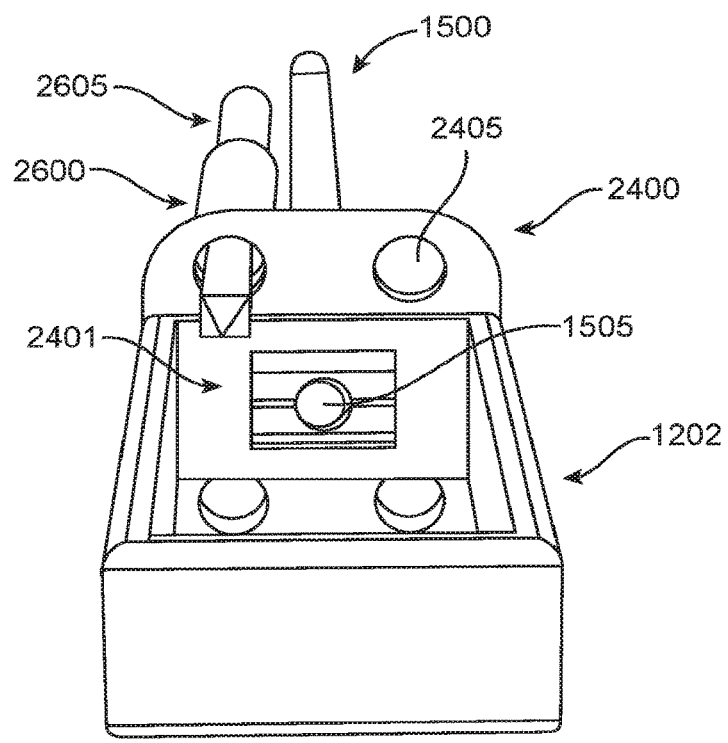

FIG. 26B depicts an angled top view of lateral cage 1202, lateral plate 2400, and inserter 1500, in an assembled configuration; and drill guide 2600 and awl or drill bit 2605, in accordance with an illustrative embodiment. Drill guide 2600 engages a screw hole 2405 and guides drill bit or awl 2605 in creating a screw pathway in a vertebral body. In this embodiment, threaded inserter end 1505 (see FIGS. 25A-25C) has been threaded into lateral plate hole 2410 (see FIGS. 25A-25C), creating an interference frictional fit of lateral plate 2400 with lateral cage 1202 via protrusion 2401, reversibly coupling lateral plate 2400 with lateral cage 1202. Inserter 1500 reversibly anchors lateral plate 2400 to lateral cage 1202, which prevents lateral plate 2400 movement while drill bit or awl 2605 establishes a screw or fastener pathway in a vertebral body and during screw or fastener insertion into the vertebral body through a plate hole or holes 2405 (see FIGS. 26C-26D) in lateral plate 2400.

FIG. 26C depicts an angled view of lateral cage 1202, lateral plate 2400, and inserter 1500, in an assembled configuration; and screwdriver 2650 inserting screw 350 into a vertebral body through a screw hole 2405 in lateral plate 2400, in accordance with an illustrative embodiment. Inserter 1500 reversibly anchors lateral plate 2400 to lateral cage 1202, which prevents lateral plate 2400 movement while drill bit or awl 2605 establishes a screw or fastener pathway in a vertebral body and during screw or fastener insertion into the vertebral body through plate hole or holes 2405 in lateral plate 2400.

FIG. 26D depicts an angled view of lateral cage 1202, lateral plate 2400, and inserter 1500, in an assembled configuration; and four screws 350 inserted through screw holes 2405 (see FIG. 26A) in lateral plate 2400 into a vertebral body, thus securing plate 2400 to the vertebral bodies (not shown) cephalad and caudal to lateral cage 1202, in accordance with an illustrative embodiment. Inserter 1500 reversibly anchors lateral plate 2400 to lateral cage 1202, which prevents lateral plate 2400 movement while drill bit or awl 2605 establishes a screw or fastener pathway in a vertebral body and during screw or fastener insertion into the vertebral body through plate holes 2405 (see FIG. 26C) in lateral plate 2400.

Figure 27A:
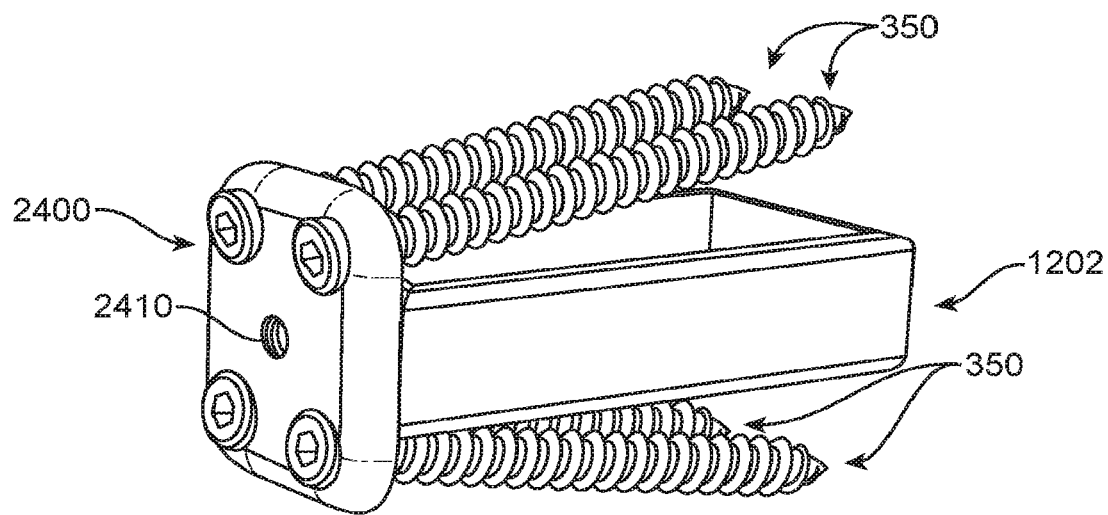
FIGS. 27A-27D depict the alternative embodiment of the lateral plate that engages a lateral cage via a medially-directed protrusion and a lateral cage, with four screws engaging the lateral plate and passing cephalad and caudal to the walls of the lateral cage, with the inserter removed, in accordance with illustrative embodiments.
Figure 27B:
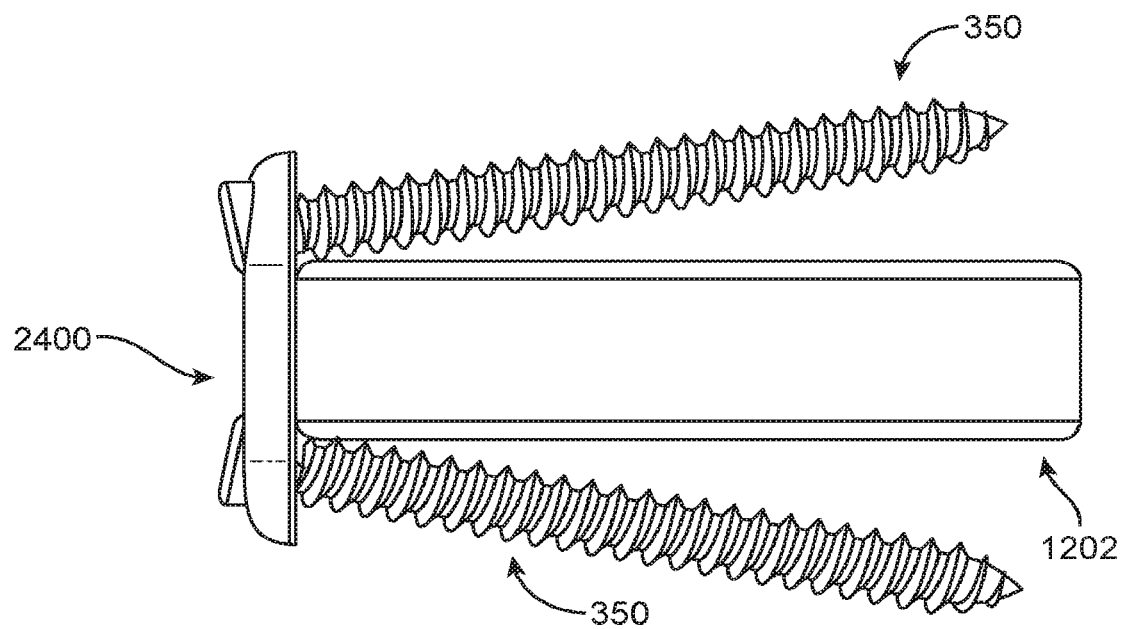
Figure 27D:
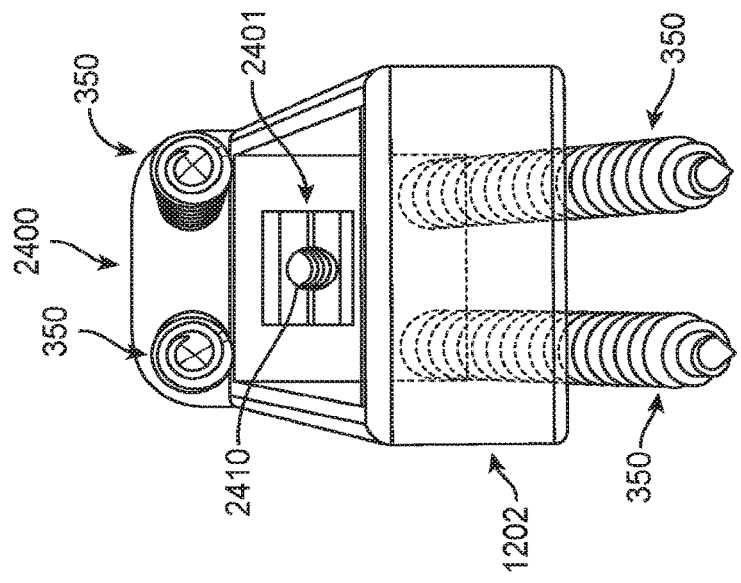
Figure 27C:
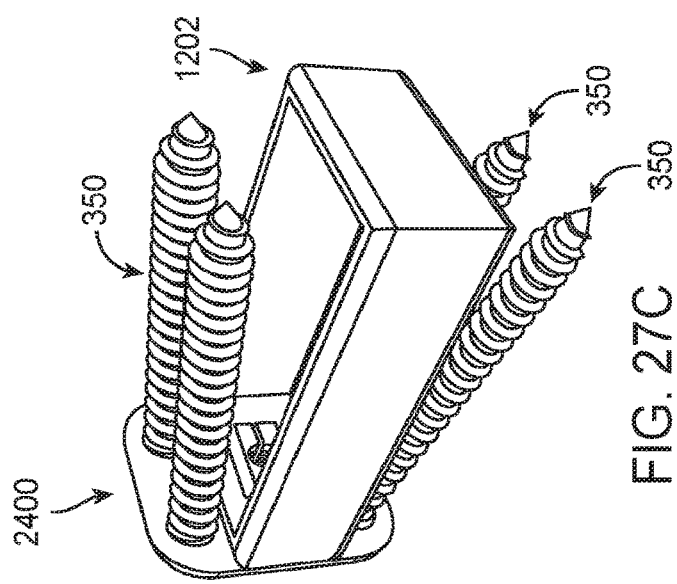

FIG. 27A depicts an angled view, FIG. 27B depicts a front or anterior view, FIG. 27C depicts an angled top view, and FIG. 27D depicts an angled medial view of lateral plate 2400, lateral cage 1202, and screws 350 inserted through screw or fastener holes 2405 (see FIG. 24A) in plate 2400 into vertebral bodies (not shown) cephalad and caudal to cage 1202, in accordance with an illustrative embodiment. In this embodiment, inserter 1500 has been removed (see FIG. 26D) and lateral plate 2400 is therefore decoupled from lateral cage 1202. Decoupling lateral plate 2400 from lateral cage 1200 allows lateral plate 2400 with associated screws 350 and lateral cage 1202 to experience independent biomechanical forces as a patient moves. In alternative embodiments (see FIG. 27E), lateral plate 2400 may be anchored to lateral cage 1202 via a connecting bolt 1800 or other connecting mechanism, in which case lateral plate 2400 and lateral cage 1202 would be subject to the same biomechanical forces as a patient moves. Screws 350 pass cephalad and caudal to the most cephalad and caudal surfaces of cage 1202, without bores or holes in the cage as in FIG. 16D. FIG. 27D depicts protrusion 2401, the medial protuberance of plate 2400, that sits within cage hole 2460 (see FIG. 24B), but without an inserter or bolt or other fastener in central plate hole 2410, and therefore protrusion 2401 does not have an interference fit with cage 1202 and therefore plate 2400 is not coupled with cage 1202.

Figure 27E:
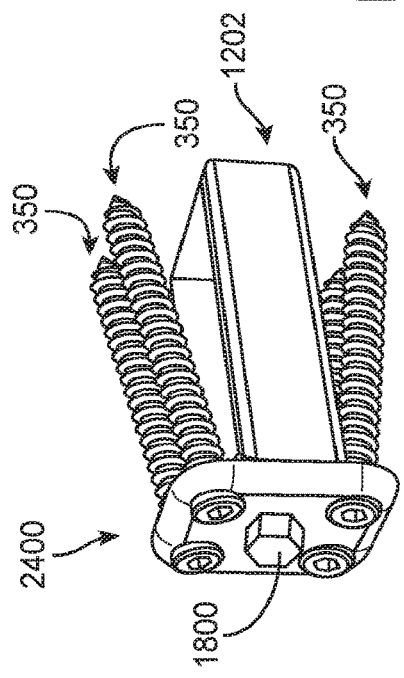
FIG. 27E depicts the alternative embodiment of the lateral plate that engages a lateral cage via a medially-directed protrusion and a lateral cage, with four screws engaging the lateral plate and passing cephalad and caudal to the walls of the lateral cage, with a bolt connecting the lateral plate to the cage in an assembled configuration, in accordance with an illustrative embodiment.

FIG. 27E depicts an angled view of lateral plate 2400, lateral cage 1202, and screws 350 inserted through holes in plate 2400 into vertebral bodies (not shown) cephalad and caudal to cage 1202, in accordance with an illustrative embodiment. Connecting bolt 1800 (see FIGS. 21D and 21E) is shown in an assembled configuration, inserted into central plate hole 2410 (see FIGS. 27A and 27D). In this embodiment, connecting bolt 1800 couples lateral plate 2400 to cage 1202 (see FIG. 25A) when threaded into lateral plate hole 2410 (see FIG. 25A), the act of which pushes top part 2402 (from FIG. 24A) away from bottom part 2403 (from FIG. 24A) of protrusion 2401 (see FIG. 25A), which in turn presses the uppermost surface of part 2402 and the bottommost surface of 2403 against the opposing surfaces of lateral cage hole 2460 (see FIG. 24B), thus creating an interference frictional fit of lateral plate 2400 with lateral cage 1202 via protrusion 2401, coupling lateral plate 2400 with lateral cage 1202. In an alternative embodiment, protrusion 2401 could couple with cage 1202 via a mechanism other than an interference fit. When lateral plate 2400 is connected to lateral cage 1202 by connecting bolt 1800 or other connecting mechanism, lateral plate 2400 and lateral cage 1202 are subject to the same biomechanical forces as a patient moves. Screws 350 pass cephalad and caudal to the most cephalad and caudal surfaces of cage 1202, without bores or holes in the cage as in FIG. 16D.

Figure 28:
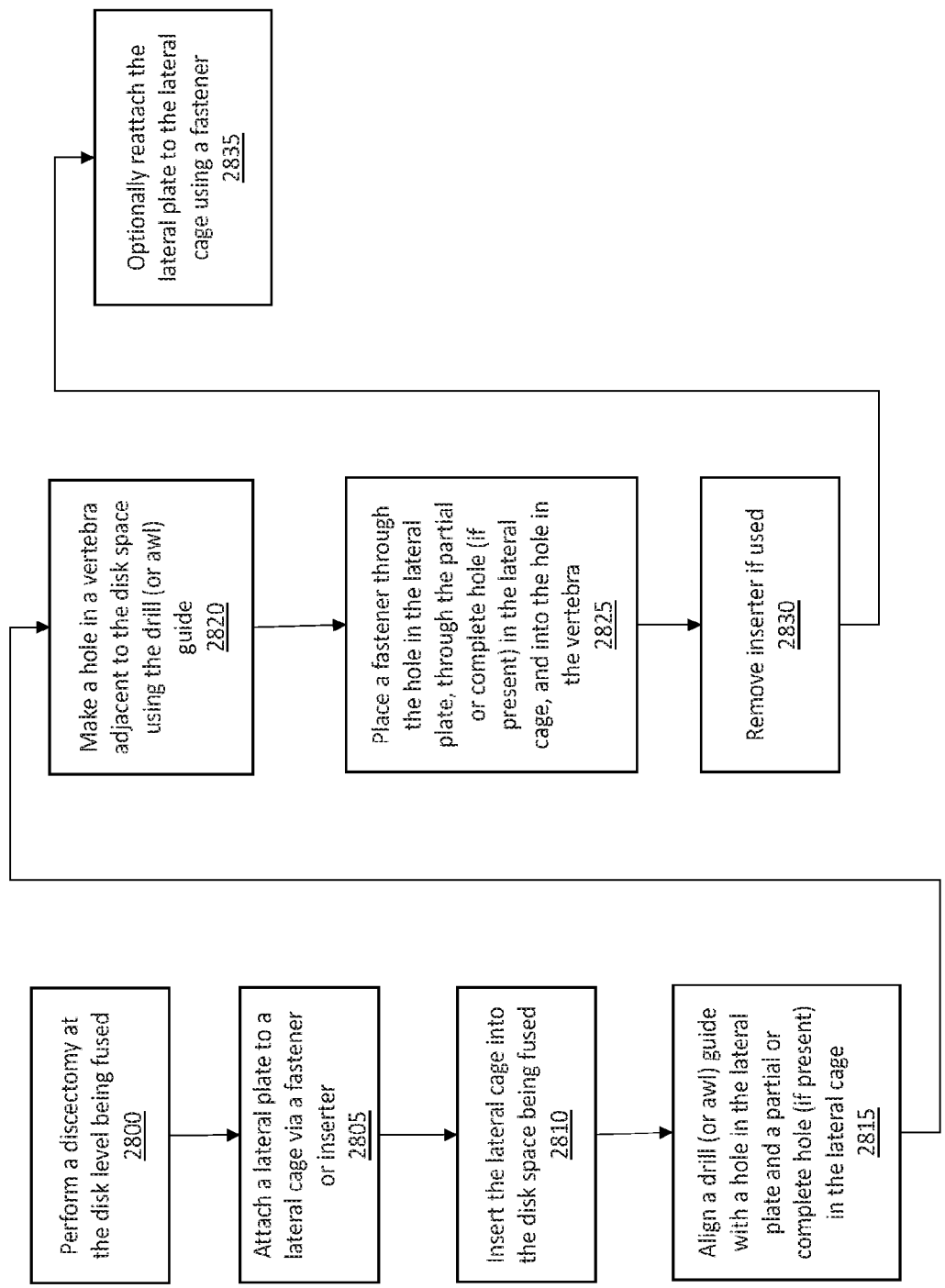
FIG. 28 is a flow diagram depicting operations performed to perform a spinal fusion procedure in accordance with an illustrative embodiment.

FIG. 28 is a flow diagram depicting operations performed to perform a spinal fusion procedure in accordance with an illustrative embodiment. In alternative embodiments, fewer, additional, and/or different operations may be performed. Additionally, use of a flow diagram is not meant to be limiting with respect to the order of operations performed. In an operation 2800, a discectomy is performed at a disk level being fused. The discectomy can be performed using any technique known in the art. In an operation 2805, a lateral plate is attached to a lateral cage through a central hole in each component. Alternatively, the hole may be off center in either or both components. The lateral plate and lateral cage can be in accordance with any of the embodiments described herein. In an illustrative embodiment, the lateral plate is attached to the lateral cage using an inserter as described herein. Alternatively, a fastener such as a screw or bolt may be used.

In an operation 2810, the lateral cage is inserted into the disk space being fused. In an alternative embodiment, the lateral cage may be inserted prior to being attached to the lateral plate. In an operation 2815, a drill (or awl) guide is aligned with a hole in the lateral plate and with a partial or complete hole (if present) in the lateral cage. In an alternative embodiment, the lateral cage may not include a partial or complete hole that aligns with the hole in the lateral plate (e.g., FIG. 20A, etc.). In an operation 2820, a hole is made in a vertebra adjacent to the disk space being fused using the drill or (awl) guide to obtain a desired angle/position of the hole. The vertebra can be above or below the disk space being fused. The hole can be made using a drill or awl as known in the art. In an operation 2825, a fastener is placed through the hole in the lateral plate, through the partial or complete hole (if present) in the lateral cage, and into the hole in the vertebra. The fastener can be a screw or bolt in an illustrative embodiment. In another illustrative embodiment, the operations 2815, 2820, and 2825 can be repeated one or more additional times such that one or more additional fasteners are used to secure the lateral plate and lateral cage to one or more vertebra.

In an operation 2830, the inserter is removed if it was used to initially attach the lateral plate to the lateral cage. In an operation 2835, the lateral plate is optionally reattached to the lateral cage using a fastener such that the two components remain attached to one another through the central (or off center) hole. Alternatively, the reattachment may not be performed such that the lateral plate and lateral cage are not attached to one another through a central (or off center) hole in each component. In another embodiment, if a fastener was initially used to attach the two components, the fastener may be removed in the operation 2830. Alternatively, if a fastener was initially used, the fastener may be left in such that the lateral plate and lateral cage remain attached to one another through the central holes.

The components described herein can be made in a variety of lengths and/or shapes to accommodate various patient anatomies and surgeon preferences. The components can be made from stainless steel, titanium, titanium-alloy, cobalt-chrome, polyether ether ketone (PEEK), a carbon fiber/PEEK combination, or any suitable material that is able to withstand the biomechanical stresses under which they will be placed.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A spine stabilization and fusion system comprising:
a lateral cage configured for placement between an upper vertebra and a lower vertebra, wherein a face of the lateral cage includes an opening; and
a lateral plate, wherein the lateral plate comprises:
one or more holes extending from a lateral face of the lateral plate to a medial face of the lateral plate, wherein the one or more holes are configured to receive one or more fasteners; and
a protrusion formed on the medial face of the lateral plate, wherein the protrusion includes a top portion, a bottom portion, and a gap that separates the top portion from the bottom portion, and wherein the opening in the face of the lateral cage receives the protrusion such that the opening in the face of the lateral cage surrounds an outer edge of the top portion of the protrusion and an outer edge of the bottom portion of the protrusion.

2. The spine stabilization and fusion system of claim 1, wherein the protrusion includes a threaded hole that extends therethrough.

3. The spine stabilization and fusion system of claim 2, wherein the threaded hole in the protrusion comprises a first threaded hole that aligns with a second threaded hole in the lateral plate, wherein the second threaded hole extends from the lateral face to the medial face of the lateral plate.

4. The spine stabilization and fusion system of claim 2, wherein a first portion of the threaded hole is formed in the top portion of the protrusion and a second portion of the threaded hole is formed in the bottom portion of the protrusion.

5. The spine stabilization and fusion system of claim 4, further comprising an inserter that has a threaded end, wherein the threaded end of the inserter is configured to thread into the threaded hole to at least temporarily secure the lateral plate to the lateral cage.

6. The spine stabilization and fusion system of claim 5, wherein the protrusion is configured to expand upon insertion of the threaded end of the inserter into the threaded hole.

7. The spine stabilization and fusion system of claim 6, wherein insertion of the threaded end of the inserter into the threaded hole forces the top portion of the protrusion and the bottom portion of the protrusion away from one another to expand the protrusion.

8. The spine stabilization and fusion system of claim 1, wherein one or more edges of the protrusion are chamfered.

9. The spine stabilization and fusion system of claim 1, wherein the face of the lateral cage further comprises one or more partial holes.

10. The spine stabilization and fusion system of claim 9, wherein each of the one or more partial holes aligns with a portion of one of the one or more holes in the lateral plate.

11. The spine stabilization and fusion system of claim 9, wherein the one or more partial holes are formed on at least one of a top edge and a bottom edge of the face of the lateral cage.

12. The spine stabilization and fusion system of claim 1, further comprising a drill guide, wherein an end of the drill guide is configured to mate with the one or more holes in the lateral plate.

13. The spine stabilization and fusion system of claim 12, wherein the end of the drill guide comprises a cannulated end that is configured to receive a drill bit.

14. A method of forming a spine stabilization and fusion system, the method comprising:
forming a lateral cage that is configured to fit between an upper vertebra and a lower vertebra, and such that a face of the lateral cage includes an opening; and
forming a lateral plate, wherein forming the lateral plate comprises:
forming a protrusion on a medial face of the lateral plate, wherein the forming the protrusion includes forming a top portion of the protrusion, forming a bottom portion, and forming a gap that separates the top portion from the bottom portion, and wherein the opening in the face of the lateral cage receives the protrusion such that the opening in the face of the lateral cage surrounds an outer edge of the top portion of the protrusion and an outer edge of the bottom portion of the protrusion; and
forming one or more holes that extend from a lateral face of the lateral plate to a medial face of the lateral plate, wherein the one or more holes are configured to receive one or more fasteners that extend into at least one of the upper vertebra and the lower vertebra.

15. The method of claim 14, further comprising placing a first threaded hole through the protrusion such that the first threaded hole aligns with a second threaded hole in the lateral plate.

16. The method of claim 15, further comprising forming an inserter that has a threaded end that is cannulated, wherein the threaded end of the inserter is configured to thread into the second threaded hole and the first threaded hole to at least temporarily secure the lateral plate to the lateral cage.

17. The method of claim 14, further comprising chamfering one or more edges of the protrusion.

18. The method of claim 14, further comprising forming one or more partial holes on at least one of a top edge and a bottom edge of the face of the lateral cage, wherein the one or more partial holes align with the one or more holes formed in the lateral plate.

\* \* \* \* \*